US011549118B2

(12) United States Patent
Rottiers et al.

(10) Patent No.: US 11,549,118 B2
(45) Date of Patent: Jan. 10, 2023

(54) GENETICALLY MODIFIED BACTERIA STABLY EXPRESSING IL-10 AND INSULIN

(71) Applicant: INTREXON ACTOBIOTICS N.V., Zwijnaarde (BE)

(72) Inventors: Pieter Rottiers, De Pinte (BE); Lothar Steidler, Lokeren (BE)

(73) Assignee: INTREXON ACTOBIOTICS NV, Zwijnaarde (BE)

( * ) Notice: Subject to any disclaimer, the term of this patent is extended or adjusted under 35 U.S.C. 154(b) by 0 days.

(21) Appl. No.: 17/092,624

(22) Filed: Nov. 9, 2020

(65) Prior Publication Data

US 2021/0180072 A1   Jun. 17, 2021

Related U.S. Application Data

(62) Division of application No. 16/329,321, filed as application No. PCT/IB2017/055287 on Sep. 2, 2017, now Pat. No. 10,858,663.

(60) Provisional application No. 62/383,079, filed on Sep. 2, 2016.

(51) Int. Cl.
| | |
|---|---|
| *C12N 15/74* | (2006.01) |
| *A61P 3/10* | (2006.01) |
| *A61K 35/744* | (2015.01) |
| *C07K 14/62* | (2006.01) |
| *A61K 39/395* | (2006.01) |
| *C07K 14/54* | (2006.01) |
| *C07K 16/28* | (2006.01) |

(52) U.S. Cl.
CPC .......... *C12N 15/746* (2013.01); *A61K 35/744* (2013.01); *A61K 39/3955* (2013.01); *A61P 3/10* (2018.01); *C07K 14/5428* (2013.01); *C07K 14/62* (2013.01); *C07K 16/2809* (2013.01); *C12N 15/74* (2013.01)

(58) Field of Classification Search
None
See application file for complete search history.

(56) References Cited

U.S. PATENT DOCUMENTS

| | | | |
|---|---|---|---|
| 4,919,918 A | 4/1990 | Cole et al. | |
| 5,223,285 A | 6/1993 | DeMichele et al. | |
| 5,470,561 A | 11/1995 | Klugkist et al. | |
| 5,695,746 A | 12/1997 | Garlick, Jr. et al. | |
| 5,700,782 A | 12/1997 | Cope et al. | |
| 5,869,118 A | 2/1999 | Morris et al. | |
| 5,972,685 A | 10/1999 | Beitz et al. | |
| 5,993,785 A | 11/1999 | Johansen et al. | |
| 6,117,417 A | 9/2000 | Wicks et al. | |
| 6,165,494 A | 12/2000 | Picciano | |
| 6,171,611 B1 | 1/2001 | Picciano | |
| 6,348,187 B1 | 2/2002 | Pan et al. | |
| 6,387,352 B1 | 5/2002 | Johansen et al. | |
| 8,524,246 B2 | 9/2013 | Rottiers et al. | |
| 8,709,398 B2 | 4/2014 | MacSharry et al. | |
| 8,759,088 B2 | 6/2014 | Steidler et al. | |
| 9,181,318 B2* | 11/2015 | Satoshi | G01N 33/502 |
| 2002/0044910 A1 | 4/2002 | Johansen et al. | |
| 2003/0152530 A1 | 8/2003 | Johansen et al. | |
| 2004/0076590 A1 | 4/2004 | Wilkins | |
| 2012/0039853 A1 | 2/2012 | Corveleyn et al. | |
| 2014/0105863 A1 | 4/2014 | Vanden-Broucke et al. | |

FOREIGN PATENT DOCUMENTS

| | | | |
|---|---|---|---|
| CN | 101605559 A | 12/2009 | |
| GB | 227835 A | 4/1925 | |
| RU | 2466185 C2 | 11/2012 | |
| WO | WO-93/17117 | 9/1993 | |
| WO | WO-96/32487 A1 | 10/1996 | |
| WO | WO-2000/18377 | 4/2000 | |
| WO | WO-2000/22909 | 4/2000 | |
| WO | WO-02/090551 | 11/2002 | |
| WO | WO-03/064607 A2 | 8/2003 | |
| WO | WO-03064607 A2 * | 8/2003 | ........... A61K 35/741 |
| WO | WO-2004056850 A2 * | 7/2004 | ......... C07K 14/5428 |
| WO | WO-2007/063075 A1 | 6/2007 | |

(Continued)

OTHER PUBLICATIONS

Supplmentary Material for Takiishi et al J Clin Invest. May 2012;122(5):1717-25.*

(Continued)

*Primary Examiner* — Oluwatosin A Ogunbiyi

(74) *Attorney, Agent, or Firm* — Banner Witcoff, Ltd.

(57) ABSTRACT

The current disclosure provides microorganisms, such as lactic acid bacteria (e.g., *Lactococcus lactis*) containing an exogenous nucleic acid encoding an IL-10 polypeptide and an exogenous nucleic acid encoding a T1D-specific antigen (e.g., a proinsulin) polypeptide, wherein both exogenous nucleic acids are integrated into the bacterial chromosome. Such microbial strains are suitable for human therapy. The disclosure further provides compositions (e.g., pharmaceutical compositions) methods of using the microorganisms and compositions, e.g., for the treatment of type 1 diabetes (T1D), including those with residual beta-cell function, e.g., recent-onset T1D. The microorganism may be administered orally, delivers the microorganism into the gastrointestinal tract, where it is released and expresses the bioactive polypeptides, The methods of the present disclosure are particularly well suited for subjects possessing residual beta-cell function, e.g., for subjects with recent-onset T1D.

17 Claims, 42 Drawing Sheets

Specification includes a Sequence Listing.

(56) References Cited

FOREIGN PATENT DOCUMENTS

| WO | WO-2012/164083 A1 | 12/2012 |
|---|---|---|
| WO | WO-2013/041673 A1 | 3/2013 |

OTHER PUBLICATIONS

Batchelor, H.K. et al., "An in vitro mucosal model for prediction of the bioadhesion of alginate solutions to the oesophagus," Int. J. Pharm., 238 (2002) 123-132.
Bisikirska et al. "TCR stimulation with modified anti-CD3 mAb expands CD8+ T cell population and induces CD8+CD25+ Tregs" J Clin Invest. Oct. 2005;115(10):2904-13.
Bisikirska et al., "Use of Anti-CD3 Monoclonal Antibody to Induce Immune Regulation in Type 1 Diabetes". Annals of the New York Academy of Sciences 2004, 1037: 1-9.
Bruschi M. L. and de Freitas O., "Oral Bioadhesive Drug Delivery Systems," Drug Development and Industrial Pharmacy, 2005 31:293-310.
Casares N. et al., A peptide inhibitor of FOXP3 impairs regulatory T cell activity and improves vaccine efficacy in mice. Journal of Immunology 2010, 185:5150-5159.
Commins SP, "Mechanisms of Oral Tolerance," Pediatr. Clin. North. Am. 2015; 62:1523-1529.
Culina S. et al., "Antigen-Based Immune Therapeutics for Type 1 Diabetes: Magic Bullets or Ordinary Blanks?," Clin. Dev. Immunol. 2011; 2011:286248, 15 pages.
Feuerer M. et al., How punctual ablation of regulatory T cells unleashes an autoimmune lesion within the pancreatic islets. Immunity 2009; 31:654-664.
Fowler S. and Powrie F, "CTLA-4 expression on antigen-specific cells but not IL-10 secretion is required for oral tolerance," European Journal of Immunology 2002, 32:2997-3006.
Gasson, M.J., "Plasmid Complements of Streptococcus lactis NCDO 712 and Other Lactic Streptococci After Protoplast-Induced Curing," J. Bacteriol. 1983, 154: 1-9.
Gazzaniga et al., "Oral delayed release system for colonic specific delivery," (1994) Int. J. Pharm. 108:77-83).
Glenting et al. Appl. Environ. Microbiol. (2002) 68:5051-5056.
Hartemann et al., "Low-dose interleukin 2 in patients with type 1 diabetes: a phase 1/2 randomised, double-blind, placebo-controlled trial," Lancet Diabetes Endocrinol. 2013, 1(4): 295-305.
Harwood and Cutting, "Molecular Biological Methods for Bacillus," John Wiley & Co. 1990, p. 341-344.
Herold K.C. and Taylor L.; "Treatment of Type 1 diabetes with anti-CD3 monoclonal antibody: induction of immune regulation?". Immunologic Research 2003, 28 (2): 141-50).
Hori S. et al., "Control of Regulatory T Cell Development by the Transcription Factor Foxp3," Science 2003; 299:1057-1061).
Kim J.M., et al., "Regulatory T cells prevent catastrophic autoimmunity throughout the lifespan of mice," Nature Immunology 2007;8:191-197.
Liston A. et al., Homeostatic control of regulatory T cell diversity. Nature Reviews Immunology 2014; 14:154-165.
Long et al., "Humoral Responses to Islet Antigen-2 and Zinc Transporter 8 Are Attenuated in Patients Carrying HLA-A*24 Alleles at the Onset of Type 1 Diabetes," Diabetes 2013, 62 (6), 2067-2071).
Ludvigsson J. et al., GAD65 antigen therapy in recently diagnosed type 1 diabetes mellitus. N. Engl. J. Med. 2012, 366:433-442.
Mayer and Shao, "Therapeutic Potential of Oral Tolerance," Nat Rev Immunol. Jun. 2004;4(6):407-19.
Mayer C.T. et al., "Few Foxp3+ regulatory T cells are sufficient to protect adult mice from lethal autoimmunity," European Journal of Immunology 2014, 44:2990-3002.
Mayer C.T. et al., "Advantages of Foxp3+ regulatory T cell depletion using DEREG mice," Immun. Inflamm. Dis. 2014, 2:162-165.
Rapoport (1990) "Gene expression using Bacillus," Current Opinion in Biotechnology 1:21 -27.
Robert et al., "Trimming of two major type 1 diabetes driving antigens, GAD6 and IA-2, allows for successful expression in Lactococcus lactis," Benef. Microbes 2015, 6(4): 591-601.
Robert S. and Steidler L., Microb. Cell Fact. 2014, 13 Suppl. 1: S11.
Robert, S. et al., Diabetes 2014, 63: 2876-2887.
Rondas et al., "Citrullinated Glucose-Regulated Protein 78 Is an Autoantigen in Type 1 Diabetes," Diabetes 2015; 64(2):573-586.
Sorensen et al. (2000) Appl. Environ. Microbiol. 66:1253-1258.
Steidler et al., Science 2000; 289(5483): 1352-1355.
Steidler L, Rottiers P, "Therapeutic Drug Delivery by Genetically Modified Lactococcus lactis," Annals of the New York Academy of Sciences 2006; 1072:176-186.
Steidler, L., et al., "Biological containment of genetically modified Lactococcus lactis for intestinal delivery of human interleukin 10" Nat. Biotechnol. 2003, 21(7): 785-789.
Strobel et al., "Immunological responses to fed protein antigens in mice," Immunology. Jul. 1983;49(3):451-6.
Suffner J. et al., "Dendritic Cells Support Homeostatic Expansion of Foxp3+ Regulatory T Cells in Foxp3.LuciDTR Mice," J. Immunol. 2010, 184:1810-1820.
Takiishi T. et al., "Reversal of autoimmune diabetes by restoration of antigen-specific tolerance using genetically modified Lactococcus lactis in mice," J. Clin. Invest. 2012, 122:1717-1725.
Tian L. et al., Foxp3+ regulatory T cells exert asymmetric control over murine helper responses by inducing Th2 cell apoptosis. Blood 2011; 118:1845-1853.
Van Asseldonk et al., "Functional analysis of the Lactococcus lactis usp45 secretion signal in the secretion of a homologous proteinase and a heterologous α-amylase,"(1993) Mol. Gen. Genet. 240:428-434.
Waterfield, N R, Lepage, R W F, Wilson, P W, et al. (1995). "The isolation of lactococcal promoters and their use in investigating bacterial luciferase synthesis in Lactococcus lactis" Gene 165(1):9-15.
Ye et al., "Grp78 Heterozygosity Promotes Adaptive Unfolded Protein Response and Attenuates Diet-Induced Obesity and Insulin Resistance,"Diabetes 2010, 59(1):6-16.
International Search Report/Written Opinion dated Dec. 13, 2017 for PCT/IB2017/055287.
European Office Action issued in European patent application No. 17 784 999.9, dated Jun. 5, 2020.
Witkowski et al., "Conversion of a β-Ketoacyl Synthase to a Malonyl Decarboxylase by Replacement of the Active-side Cysteine with Glutamine," Biochemistry 38:11643-11650, 1999 (Year: 1999).
Devos et al., "Practical Limits of Function Prediction" (Proteins: Structure, Function and Genetics, 2000, vol. 41: 98-107), (Year: 2000).
Whisstock et al., "Prediction of protein function from protein sequence and structure," (Quarterly Reviews of Biophysics 2003, vol. 36 (3): 307-340) (Year: 2003).
Russian Office Action issued in Russian patent application No. RU2019104948 dated Dec. 23, 2020 w/machine English translation.
Russian Office Action issued in Russian patent application No. RU2019104948 dated May 21, 2021 w/machine English translation.
Wasserfall, C. H. et al., "Autoantibody markers for the diagnosis and prediction of type 1 diabetes", Autoimmunity Reviews 2006, vol. 5, pp. 424-428.
Media announcement from Precigen, on Jun. 10, 2021 (available at <https://investors.precigen.com/news-releases/news-release-details/precigen-actobio-announces-additional-positive-interim-data>).
Notice of the First Office Action dated Oct. 18, 2022 in Chinese Patent Application No. 201780054190.7 (11 pages) with an English translation (10 pages).

\* cited by examiner

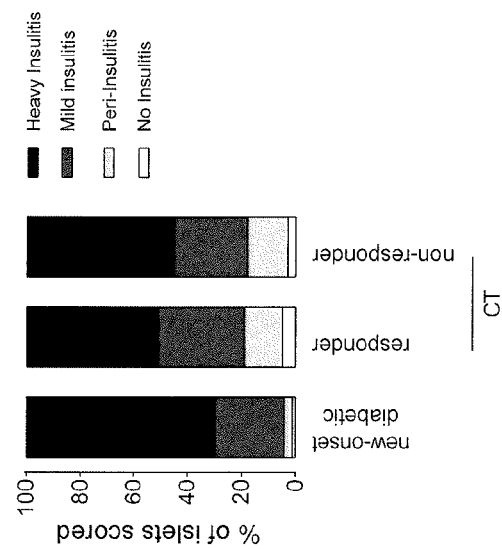

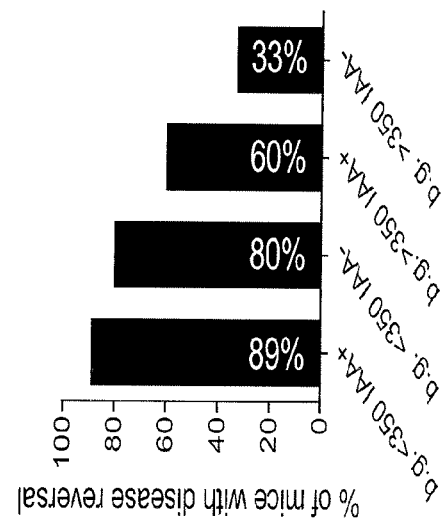

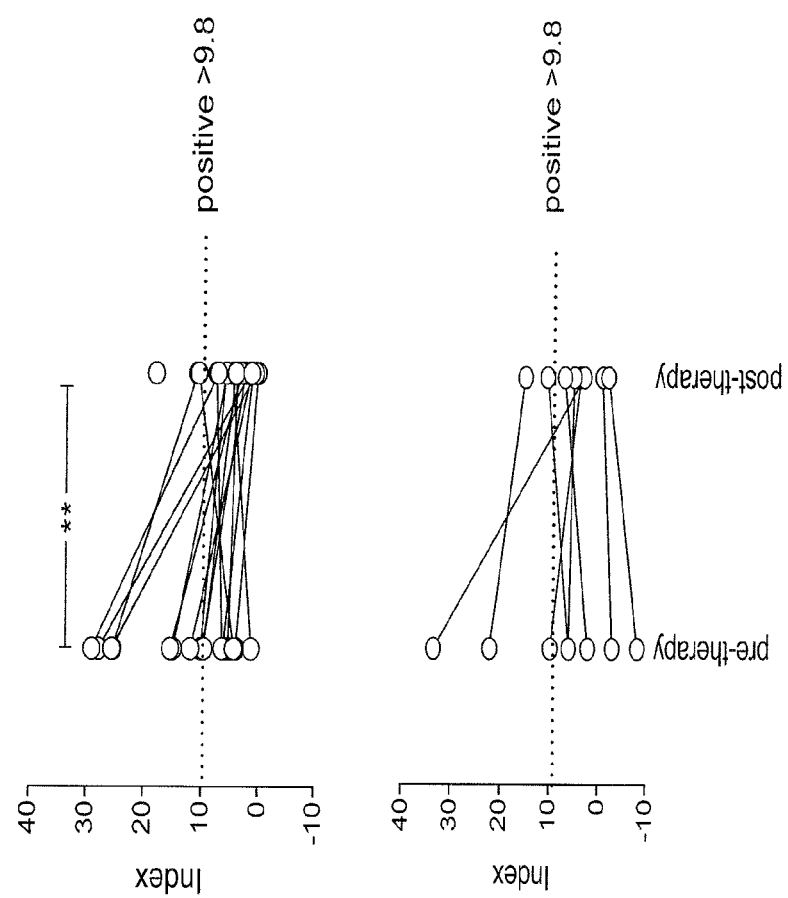

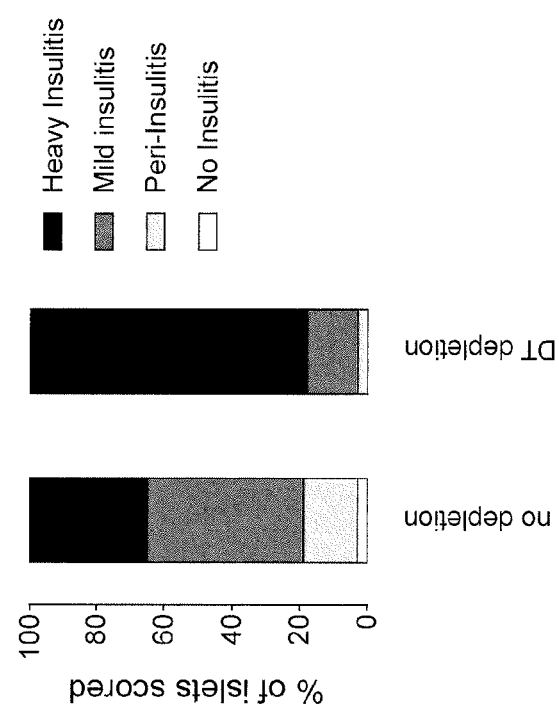

Figure 11

```
  1  aaaacgcctt aaaatggcat tttgacttgc aaactgggct aagatttgct aaaatgaaaa
     >>..............................Ph11A...........................>

61  atgcctatgt ttaaggtaaa aaacaaatgg aggacatttc taaaatgaaa aaaaagatta
     >................... Ph11A..................>>
                                                        >>...SSusp45....>
                                                          m  k  k  i 121  tctcagctat tttaatgtct acagtgatac tttctgctgc agccccgttg tcaggtgttt
     >..............................SSusp45...........................>
       i  s  a  i  l  m  s  t  v  i  l  s  a  a  a  p  l  s  g  v 181  acgcctcagc tggtcaaggt actcaatcag aaaactcatg tactcacttt ccaggtaact
     >..>> SSusp45
         y  a
           >>.....................hIL10aPxA..........................>
             s   a  g  q  g   t   q  s  e  n  s   c  t  h  f   p  g  n 241  tgccaaacat gcttcgtgat ttgcgtgatg cttttcacg tgttaaaact ttttttcaaa
     >..............................hIL10aPxA.........................>
       l  p  n  m  l  r  d  l  r  d  a  f  s  r  v  k  t  f  f  q 301  tgaaagatca acttgataac ttgcttttga aagaatcact tttggaagat tttaaggtt
     >..............................hIL10aPxA.........................>
       m  k  d  q  l  d  n  l  l  l  k  e  s  l  l  e  d  f  k  g 361  accttggttg tcaagctttg tcagaaatga tccaatttta ccttgaagaa gttatgccac
     >..............................hIL10aPxA.........................>
       y  l  g  c  q  a  l  s  e  m  i  q  f  y  l  e  e  v  m  p 421  aagctgaaaa ccaagatcca gatatcaaag ctcacgttaa ctcattgggt gaaaacctta
     >..............................hIL10aPxA.........................>
       q  a  e  n  q  d  p  d  i  k  a  h  v  n  s  l  g  e  n  l 481  aaactttgcg tcttcgtttg cgtcgttgtc accgttttct tccatgtgaa aacaaatcaa
     >..............................hIL10aPxA.........................>
       k  t  l  r  l  r  l  r  r  c  h  r  f  l  p  c  e  n  k  s 541  aagctgttga acaagttaaa aacgctttta acaaattgca agaaaaaggt atctacaaag
     >..............................hIL10aPxA.........................>
       k  a  v  e  q  v  k  n  a  f  n  k  l  q  e  k  g  i  y  k 601  ctatgtcaga atttgatatc tttatcaact acatcgaagc ttacatgact atgaaaatcc
     >..............................hIL10aPxA.........................>
       a  m  s  e  f  d  i  f  i  n  y  i  e  a  y  m  t  m  k  i 661  gtaactaact agaattaatc tataagttac tgacaaaact gtcagtaact ttttttgtgg
     >......>> hIL10aPxA
       r  n  -
```

Figure 12A

```
  1  aataaaaatt actgacagcc tgctcagtaa ttttttttagt cataattttt aggtggaaag 61  tcaaagatta ttgccaaaag tattagcttt tttaatgtta accgctttca gaagaagggg 121  agttcatttg cttttgtaga gcgctttcta aggtagttta tgtttgcaaa ttttaaaaaa
                                                             PgapB >>.>
                                                                      k 181  agtgttaaaa taaaagagta agttaaattg ttaacttagt caatttaaaa ggtttgcctt
     >..........................PgapB.................................>

241  ttataaaatc taatccctat aaggaggaaa ctactaatgg tagttaaagt tggtattaac
     >..............PgapB...............>>
                                          >>..........gapB............>
                                            m   v   v   k   v   g   i   n 301  ggtttcggtc gtatcggtcg tcttgctttc cgtcgtattc aaaatgttga aggtgttgaa
     >...............................gapB..............................>
       g   f   g   r   i   g   r   l   a   f   r   r   i   q   n   v   e   g   v   e 361  gttgttgcaa tcaacgactt gacagatcca gcaatgcttg ctcacttgct taaatacgat
     >...............................gapB..............................>
       v   v   a   i   n   d   l   t   d   p   a   m   l   a   h   l   l   k   y   d 421  acaactcaag gtcgttttga tggtaaagtt gaagttaaag atggtggttt tgaagttaac
     >...............................gapB..............................>
       t   t   q   g   r   f   d   g   k   v   e   v   k   d   g   g   f   e   v   n 481  ggtaaattcg ttaaagttac tgctgaatct aacccagcta acatcaactg ggctgaagtt
     >...............................gapB..............................>
       g   k   f   v   k   v   t   a   e   s   n   p   a   n   i   n   w   a   e   v 541  ggtgcagaaa tcgttcttga agcaactggt ttcttcgcaa ctaaagaaaa agctgaacaa
     >...............................gapB..............................>
       g   a   e   i   v   l   e   a   t   g   f   f   a   t   k   e   k   a   e   q 601  cacttgcacg ctaatggtgc taagaaagtt gttatcactg cacctggtgg atcagatgtt
     >...............................gapB..............................>
       h   l   h   a   n   g   a   k   k   v   v   i   t   a   p   g   g   s   d   v 661  aaaacaatcg ttttcaacac taaccacgaa gtacttgatg gaactgaaac agtaatttca
     >...............................gapB..............................>
       k   t   i   v   f   n   t   n   h   e   v   l   d   g   t   e   t   v   i   s 721  gctggttcat gtacaaccaa ctgtcttgct ccaatggctg atacttgaa caaacaattc
     >...............................gapB..............................>
       a   g   s   c   t   t   n   c   l   a   p   m   a   d   t   l   n   k   q   f 781  ggtatcaaag ttggtacaat gactacagtt cacggttaca ctggtgacca aatgactctt
     >...............................gapB..............................>
       g   i   k   v   g   t   m   t   t   v   h   g   y   t   g   d   q   m   t   l 841  gatggcccac accgtggtgg agatttccgt cgcgcacgtg ctgcagctga aaacatcgta
     >...............................gapB..............................>
       d   g   p   h   r   g   g   d   f   r   r   a   r   a   a   a   e   n   i   v 901  cctaactcaa caggtgctgc taaagccatc ggtcttgtat tgccagaact tcaaggtaaa
     >...............................gapB..............................>
       p   n   s   t   g   a   a   k   a   i   g   l   v   l   p   e   l   q   g   k
```

Figure 12B

```
 961   cttcaaggac atgctcaacg tgtaccagtt ccaactggtt cattgactga acttgttact
       >............................gapB..............................>
        l  q  g   h  a  q   r  v  p   v  p  t   g  s  l   t  e  l   v  t 1021   atccttgata agaagttac agttgacgaa atcaacgcag ctatgaaagc tgcttcaaat
       >............................gapB..............................>
        i  l  d   k  e  v   t  v  d   e  i  n   a  a  m   k  a  a   s  n 1081   gaatcatttg gttacaacga agaccaaatc gtttcatctg atatcgttgg tatctcaaac
       >............................gapB..............................>
        e  s  f   g  y  n   e  d  q   i  v  s   s  d  i   v  g  i   s  n 1141   tcttcactct ttgatgctac tcaaactgaa gttacttcag ctaacggagc tcaacttgtt
       >............................gapB..............................>
        s  s  l   f  d  a   t  q  t   e  v  t   s  a  n   g  a  q   l  v 1201   aaaactgtat cttggtacga taacgaaatg tcatacactt caaaccttgt tcgtacactt
       >............................gapB..............................>
        k  t  v   s  w  y   d  n  e   m  s  y   t  s  n   l  v  r   t  l 1261   gcatacttcg ctaaaatcgc taaataagga ggaaaaaatg aagaagaaaa tcattagtgc
       >..........gapB.........>>
        a  y  f   a  k  i   a  k
                              >>...TRrpmD..>>
                                        >>........SSusp45........>
                                          m  k   k  i  i   s 1321   catcttaatg tctacagtga ttctttcagc tgcagctcct ttatcaggcg tttatgcatt
       >.......................SSusp45.........................>>
        a  i  l   m  s  t   v  i  l   s  a  a   a  p  l   s  g  v   y  a
                                                              pins >>

1381   tgtgaaccaa cacctgtgcg gctcacacct ggtggaagct ctctacctag tgtgcgggga
       >.................pins...........................>
        f  v  n   q  h  l   c  g  s   h  l  v   e  a  l   y  l  v   c  g 1441   acgaggcttc ttctacacac ccaagacccg ccggaggca gaggacctgc aggtgggca
       >.................pins...........................>
        e  r  g   f  f  y   t  p  k   t  r  r   e  a  e   d  l  q   v  g 1501   ggtggagctg ggcggggcc ctggtgcagg cagcctgcag cccttggccc tggaggggtc
       >.................pins...........................>
        q  v  e   l  g  g   g  p  g   a  g  s   l  q  p   l  a  l   e  g 1561   cctgcagaag cgtggcattg tggaacaatg ctgtaccagc atctgctccc tctaccagct
       >.................pins...........................>
        s  l  q   k  r  g   i  v  e   q  c  c   t  s  i   c  s  l   y  q 1621   ggagaactac tgcaactaat tttccgattt taacggtata aaaaccagtc ttcgggctgg
       >........pins......>>
        l  e  n   y  c  n   -
```

Figure 13A

```
   1 gatggctgaa gctccaactc atgaacaagt tgaccatgtt gtggatacaa ttgttgaagt tgttgaagag gaaattggtg tgaaataaag aaaagccaag
     >>........ .......... .......... ........../ femD...... .......... .......... .......... .......... .......>>

101 gagaatattc ttcttgtctt tttcatatc ctaaaactct acctactgtg gtagagtttt tttatctttt ttggcgtcta gcaaactctg taaaacgaaa
     .......... .......... .......... .......... .......... .......... .......... .......... .......... ......<<
                                                                                                         .treR.

201 acggtcaacc tgatgtcgtg attcagtata ctggaaaagt gtattatcgg caagatagac atgagatttc acggaaacaa catgatggtc cttcggattt
     .......... .......... .......... .......... .......... .......... .......... .......... .......... ..........
     .treR.

301 aaatcaagat atgtaaaatc atcttcacaa gcaaaatcaa tggtaacttc tttttgggca taggcaatat caagtcccaa agccccttct aaataatcgt
     <<........ .......... .......... .......... .......... .......... .......... .......... .......... ..........

401 aagtagaatt ttgggcatgt gcggggtca aaccatcagc gtattttttct aaaataaat cccaatccaa aatgaaaaat ttaccatcta ctttttcttct
     <<........ .......... .......... .......... .......... ..treR.... .......... .......... .......... ..........

501 tctaagaata ctaagggctt ggtcgccgat ggcgaatcca gtagttcctg aaagagctgg gtaattttt atactttcaa atttattac ttcagtttca
     <<........ .......... .......... .......... .......... ..treR.... .......... .......... .......... ..........

601 ctgtcaaaac ccattgaagt ttgcaattct ttatatgaag ttaagcccgga aataggaaa aggagccgat cgtgagcgag gacaatgctg ccatagccat
     <<........ .......... .......... .......... .......... ..treR.... .......... .......... .......... ..........

701 gtcttcttg gatgagccct tttcttccta aaattttaa agcttgtctg acgttgaac ggctactttc ataactaata gaaagttcat tctcgcttgg
     <<........ .......... .......... .......... .......... ..treR.... .......... .......... .......... ..........

801 aagaatatcg ttcgttttat agatatcatt aaaaatcttt tttctaaat cttgcaaaat cacttcatat ttcttcatac tttatatttt atcataaaaa
     <<........ .......... .......... .......... .......... ..treR.... .......... .......... .......... ......<<

901 taattgttaa cgcttgctga aacgttttt atgaaaacgc cttaaaatg catttttgact tgcaaactgg gctaagattt gctaaaatga aaaatgccta
     >>........ .......... .......... .......... .......... ..Ph11A... .......... .......... .......... .......>>

1001 tgtttaaggt aaaaaacaaa tggaggacat ttctaaaatg tttggaatag gaaaaaagaa agaattgaga catgataaaa gcctttatgc tccagtttct
     >>........ .......... .......... .......... .......... ..Ph11A... .......... .......... .......... ..........
                                                                                                              .ptsI.

1101 ggggaagtta tcaacctttc aacagtcaac gacccgtat tttcaaaaaa gataatggga gacgggttcg cggttgagcc aaaagaaaat aaaattttg
     >>........ .......... .......... .......... .......... ..ptsI.... .......... .......... .......... ..........
```

Figure 13B

```
1201 cccagtttc tgcaaagta actttggttc aaggacatgc aattggtttt aaacgtgctg atggcttaga tgtactttta catcttggaa ttgatacagt
     >..........................................................................................ptsI...
     >...

1301 agctcttaaa ggtcttcatt ttaaaatcaa ggtcaaagtt gatgatattg tcaatggtgg tgatgagctt ggaagcgttg attgggcaca gattgaagct
     >..........................................................................................ptsI...
     >...

1401 gcaggtttag ataaaacgac aatggttatc caaaagataa actctctgag ttcaatgtca attatggacc agctacttct ggaagtgaac
     >..........................................................................................ptsI...
     >...

1501 ttggtaaggc aagtgttaaa taaggaggaa aaatggcaa attattcaca acttgcgaca gaaattatcg caaatgtagg tggcgctgag aatgtcacaa
     >.........Pts I..............>>
     >............................IRrpmD..>>..............................................................

1601 aagttattca ctgtatcact cgtcttcgtt ttaccttgaa agacaaagat aaagcagata cggcggcgat tgaagccta cctggtgtcg cctggagcgt
     >..........................................................................................ptsII...
     >...

1701 ttataactca aacttgaatc aatatcaagt agttattgga caagctgtag aagatgttta tgacgaggtt gttgaacagc ttgagattc agttgt=gat
     >..........................................................................................ptsII...
     >...

1801 gaagatgcaa cggcgcaagc acttactgca acagcaccgg ctagtgctaa acagcaccgg ccaattgttc atgcttttcca agtggttatt gggacaatta
     >..........................................................................................ptsII...
     >...

1901 caggttcgat gattccaatt attggtttac ttgcggctgg tggga=gatt aatggattat taagtatctt tgttaaagga aatcgttaa ttgaagtgat
     >..........................................................................................ptsII...
     >...

2001 tgaccctgca agttcaactt acgtcattat ctcaactcta gcaatgacac cattttattt cttacctgtt ttagtacgat tttcagcagc aaaacaatta
     >..........................................................................................ptsII...
     >...

2101 gcacctaaag atactgtttt acaattatt ggtgctgctg ttggtggttt catgattaat ccagggatta ctaacttggt aaatgctcat gttgaacaa
     >..........................................................................................ptsII...
     >...

2201 atgcggccgg taaaatgtt gtgttgaag cagcagctcc agtagcactc ttccttgaag tcacttttaa tacaagttat tttgcaattc cggttgcttt
     >..........................................................................................ptsII...
     >...

2301 gccaagttat gcttataaca ttttcccaat cattgtggcg gtagcaatcg ctaaaccttt gaatgcttgg ttgaaaaagg ttttaccact tgccttgcgt
     >..........................................................................................ptsII...
     >...
```

Figure 13C

```
2401 ccaattttcc aaccgatgat tactttcttc atcactgctt caatcattt actcttggtc ggtcctgtta tttcaacaat ttcatctggt ttgtcattcg
     >..........................................................ptsII...........................................>
2501 ttattgacca tatcttgtca ttaaacttag ggattgcaag tattatcgtc ggtggttgt atcaatgttt ggttatattt ggttgcact ggttggttgt
     >..........................................................ptsII...........................................>
2601 accacttatt tcacaagagt tggcagcaac aggagcaagc tcacttaata tgattgttag cttcacaatg cttgcgcaag gagttggtgc cttgactgtc
     >..........................................................ptsII...........................................>
2701 ttcttttaaat ctaaaaaagc tgacctttaaa ggactttctg ctccagctgc catttcggct ttttgtggag taactgaacc tgccatgtac ggaattaact
     >..........................................................ptsII...........................................>
2801 tgaaatatgc tcgcgtcttc atcatgtctt caattggtgc agcaattggt gctgggattg ccgcattttgg tggcttacaa atgtttggat tttcagggtc
     >..........................................................ptsII...........................................>
2901 attgattagc ttcctaact ttatctctaa tccattgacg catcatgcac ctgcgggtaa cttaatgctc ttctgattg ccactgcggt atgtgctgtt
     >..........................................................ptsII...........................................>
3001 gccactttct tattagtttg gttcttttggt tacaaggata ctgatgtcat gggacaagga gttgaacaaa aaaatgcatt taaggatgct gtaaaataaa
     >..........................................................ptsII.........................................>>
3101 tagttttgct cttaataaag ttttgataca aggatttaca attatttttt gataaaaaa ttactgatag aaatgaaaaa aattctgtca gtaattttgg
3201 aaagtcattc taaaaaattc attttaaaat gacgagaaag aagtaaaaa gatgttaaa gcagtattgt ttgatttaga tggcgtaat
                                                          >>.........................................pgmB/.........>>
```

Figure 14A

```
   1 gtaattctaa tgctggtggg aatacaaatt caggcactag tactggaaat actggaggaa caactactgg tgtagcggt ataaatagtt caccaattgg
     >>................................................................................../usp45.................^
 101 aaatccttat gctggtggtg gatgtactga ctatgtatgg caatacttg ctgcacaagg aatttatatc agaaatatca tgcctgtaa tggtgacaa
     .........................................................................................................^
 201 tggcttcta atggacctgc ccaaggcgtg ctccatcttg taggagctgc tcctggtgtt atcgcatcaa gcttctcagc tgattttgtt ggatatgcaa
     ............................................................................../usp45...................^
 301 actcaccta cggtcacgta gctattgtaa aatcagttaa ttcagatggt acaattacta tcaaagaagg cggatatggt acaactggt ggggacatga
     ............................................................................../usp45...................^
 401 acgtactgta agtgcgtctg gtgttacttt cttgatgcca aactaaggag gaaaaatga cagaaccgtt aaccgaaacc cctgaactat ccgcgaaata
     ..../usp45................>>
                              >>.IRrpmD.>>
                                          >>................................................otsB..........^
 501 tgcctggtt tttgatcttg atggaacgct ggcggaaatc ccgatcaggt aaaccgcatc cgtcgtgcct gacaatattc tgcaaggact acagctactg
     ..........................................................................................otsB..........^
 601 gcaaccgcaa gtgatggtgc attggcattg atatcagggc gctcaatggt ggagcttgac gcactggcaa aaccttatcg cttcccgtta gcgggcgtgc
     ..........................................................................................otsB..........^
 701 atggggcga gcgcgtgac atcaatggta aaacacatat cgttcatctg ccggatgcga ttgcgcgtga tattagcgtg caactgcata cagtcatcgc
     ..........................................................................................otsB..........^
 801 tcagtatccc ggcgcggagc tggaggcgaa agggatggct tttgcgctgc attatcgtca ggctccgcag catgaagacg cattaatgac attagcgcaa
     ..........................................................................................otsB..........^
 901 cgtattactc agatctggcc acaaatggcg ttacagcagg gaaagtgtgt tgtcgagatc aaaccgagag gtaccagtaa aggtgaggca attgcagctt
     ..........................................................................................otsB..........^
1001 ttatgcacga agctcccttt atcgggcgaa cgcccgtatt tctggggcat gattaaccg atgaatctgg cttcgcagtc gttaaccgac tgggcggaat
     ..........................................................................................otsB..........^
1101 gtcagtaaaa attggcacag gtcaactca ggcatcatgg cgactggcgg gtgtgccgga tgtctggagc gtgccttgaaa tgataaccac cgcattacaa
     ..........................................................................................otsB..........^
```

Figure 14B

```
1201 caaaaaagag aaaataacag gagtgatgac tatgagtcgt ttagtcgtag tatctaaaaa aaagtcttaa taaataaaaa atagtggttt gatagtgggg
     >.........otsB.........>>
1301 aataatttc cttctgtcaa atcatttttt attattgtgg tataataata aggaaaaatg ataagggat agatacaaat gtgtggaatt gtcggcttta
                                                                                          >>......asnH/.........
1401 ttgaccggat cgatcaaaat gataaatcaa aaactttaga agaaatgatg gatacaatcg ctcaccgagg tccaagtagt tcaggtgaat ttattgacga
     >.........asnH/.........
1501 aggagcagca attggttttc gtcgcctgag tattattgac cttgagggtg gagatcaacc tatctttaat gaagataaaa ctaaacttat aaccttaat
     >.........asnH/.........
1601 ggcgaaattt ataatttccg tgaattgcgt gaagacctta tctctaaagg tcatgatttt actactcatg ctgatacaga agtgctttta catggttacg
     >.........asnH/.........
```

Figure 15A

```
  1 cacggaatta acacgcatta tgacttaacg aggcaattac ctacggtcta tttgacagaa cgtttaacag atctcgttta tcaacgttcc aactaaaaaa
    >>................................................................................................/transcriptional..................................................>>

101 gccaatctgg cttttttcta tgctctgtcg ttcctaatgg tttgatatct aaaagtaaaa aagttaaatt gagataacaa atataattat caaggctgaa 201 cctcgcaagc ttaaaggaaa ctttatatgac aatttttggta caggagtctt caaaagtggc acagaaccaa agtgatggaa aaataagaaa ctgctttctt 301 tactttgcct attaatgcta taatgaaaat gtagaaaaga tggacgtgaa accagttcat caaaaaaagt aaaggagact gttcaaccat gaacaatttt
                                                                                                       >>..ptcC/...>
                                                                                                             m  n  n  f 401 attcaaaaca aaatcatgcc tccaatgatg aaatttttga ataccgtgc agtcacggca atcaaaaatg gtatgtgaat tcctatccca tttatcatta
    >.............................................................................................................>
     i  q  n  k  i  m  p  p  m  k  f  l  n  t  r  a  v  t  a  i  k  n  g  m  -  i  p  i  p  f  i  i
                                                                                               tga30
                                                                                               EcoRI 501 ttggttcagt attcttgatt cttggtcaac agcaggacaa gacttcatga acaaaatcaa attgggccca ctctttttac aaattaataa
    >.....................................................................................ptcC/................^
     i  g  s  v  f  l  i  i  l  g  q  l  p  f  q  a  g  q  d  f  m  n  k  i  k  l  g  p  l  f  l  q  i  n 601 tgcttcattt ggtatatgg cttgcttcgc cgtgttcggt attgcttacg ctgggttcg agatgcaggt tatgaaggag taccggctgg tttaacaggt
    >...................................................................ptcC/......................................^
     n  a  s  f  g  i  m  a  l  l  a  v  f  g  i  a  y  a  w  v  r  d  a  g  y  e  g  v  p  a  g  l  t  g 701 gtcattgttc acatcttgtt gcaaccagac acaatccatc aagtaacaag tgttactgac caactaaaa catcaacagc atttcaagta ggtggtgtca
    >.......................................................ptcC/..................................................^
     v  i  v  h  i  l  l  q  p  d  t  i  h  q  v  t  s  v  t  d  p  t  k  t  s  t  a  f  q  v  g  g  v 801 ttgaccgagc ttggttaggt gggaaaggga tggttctctc aatcatcgtt ggactcttag taggttggat ttacactggc tttatgcgtc ggaacatcac
    >.......................................................................................................>
     l  d  r  a  w  l  g  g  k  g  m  v  l  s  i  i  v  g  l  l  v  g  w  i  y  t  g  f  m  r  r  n  i 901 aatcaaaatg ccagaacaag ttccagaaaa cgttgccgca tcatttactt cacttgtaac tgcaggagca atcattacaa tggctggtgt ggttcatgga
    >...........................................ptcC/..................................................>
     t  i  k  m  p  e  q  v  p  e  n  v  a  a  s  f  t  s  l  v  p  a  g  a  i  i  t  m  a  g  v  v  h  g
```

Figure 15B

```
1001 atcacaacga ttggcttcaa cacaacttt
     >..........ptcC/..........>>
        i  t  t  i  g  f  n  t  t
```

Figure 16

```
  1 tcagctaacg gagctcaact tgttaaaact gtatcttggt acgataacga aatgtcatac acttcaaacc ttgttcgtac acttgcatac ttcgctaaaa
    >../gapB..>>
    >................................................................................................/gapB..>

101 tcgctaaata aggaggaaaa aatgaagaag aaatcatta gtgccatctt aatgtctaca gtgattcttt cagctgcagc tcctttatca cgcgtttatg
    >>.IRrpmD..>>
    >>...................................>>.SSusp45..

201 cattgtgaa ccaacacctg tcggctcac acctggtgga agctctctac ctagtgtgcg gggaacgagg cttcttctac acaccaaga cccgccggga
    >> SSusp45                            pins
    >>.............>>......................................................................

301 ggcagaggac ctgcaggtgg ggcaggtgga gctgggcggg ggccctggtg caggcagcct gcagcccttg gccctggagg ggtccctgca gaagcgtggc
    pins
    >.......................................................................>

401 attgtgaac aatgctgtac cagcatctgc tccctctacc agctggagaa ctactgcaac taattttccg atttaacgg tataaaaacc agtcttcggg
    pins
    >................................>>
```

Figure 17

```
  1 aatccaatga cggcacttct tccttggacg acaccagcac ctgtgagaat ggccatttca ggtggacttc catttttgat tatttttgca atctgtttag
    >>......................................................................................................'PTS.......^
101 tcttgaatgt tcttatttac tacccattct ttaaggtggc gtataataaa gctttagaag aagaaaaagc agctgttgaa ttagagggtt cagaaactgc
    .........................................................................................................'PTS....^
201 ctgatggaaa acgccttaaa atggcatttt gacttgcaaa ctgggctaag atttgctaaa atgaaaaatg cctatgttta agtaaaaaa caaatgaagg
    >.>> ./PTS............................................................................................Ph1A......^
    >.>>
301 acatttctaa aatgaaaaaa aagattatct cagctattct aatgtctaca gtgatacttt ctgctgcagc cccgttgtca gtgtttacg cctcagctgg
    >..Ph1A..>>..........................................................SSusp45.............................^
                      >>..............................................................................hIl10 >>.......^
                                                                                                               s  a
401 tcaaggtact caatcagaaa actcatgtac tcactttcca gtaacttgc caaacatgct tcgtgatttg cgtgatgctt tttcacgtgt taaaactttt
    ^.........................................................hIL10.......................................^
501 tttcaaatga aagatcaact tgataacttg ctttgaaag aatcactttt ggaagatttt aaaggttacc ttggtgtca agctttgtca gaaatgatcc
    ^..............................................hIL10.................................................^
601 aattttacct tgaagaagtt atgccacaag ctgaaaacca agatccagat atcaaagctc acgttaactc attggtgaa aattgcaaga ctttgcgtct
    ^.........................................hIL10......................................................^
701 tcgtttgcgt cgttgtcacc gtttttcttcc atgtgaaatg ctgttgaaca aaatcaaaag gcttttaaca aattgcaaga aaaaggtatc
    ^................................................hIL10...............................................^
801 tacaaagcta tgtcagaatt tgacatcttt atcaactaca tcgaagctta catgactatg aaaatccgta actaactaga attaatctat aagttactga
    ^........................................................hIL10.....>>.................................^
901 caaactgtc agtaacttc tttgtgggaa aatgtatct ttatgaccgt aaagaatctg tcagtagaag tctgaaattc gtttaaaaat cgactagaat
```

GENETICALLY MODIFIED BACTERIA STABLY EXPRESSING IL-10 AND INSULIN

CROSS REFERENCE TO RELATED APPLICATION

This application is a division of U.S. patent application Ser. No. 16/329,321, filed Feb. 28, 2019, now U.S. Pat. No. 10,858,663, issued Dec. 8, 2020, which is the national phase entry of International Application No. PCT/IB2017/055287, filed Sep. 2, 2017, and claims benefit of the filing date of U.S. Provisional Application No. 62/383,079, filed Sep. 2, 2016, the disclosure of each of which is hereby incorporated herein by this reference in its entirety.

REFERENCE TO SEQUENCE LISTING

The instant application contains a Sequence Listing which has been submitted electronically in ASCII format via EFS-WEB and is hereby incorporated by reference in its entirety. Said ASCII copy, created on Nov. 28, 2022, is named 009581.00020_US_SubSL.txt and is 42,419 bytes in size.

BACKGROUND

Genetically modified microorganisms (e.g., bacteria) have been used to deliver therapeutic molecules to mucosal tissues. See, e.g., Steidler, L., et al., *Nat. Biotechnol.* 2003, 21(7): 785-789; and Robert S. and Steidler L., *Microb. Cell Fact.* 2014, 13 Suppl. 1: S11.

Interleukin 10 (IL-10) producing lactic acid bacteria have been previously described and mucosally administered IL-10 and/or insulin or proinsulin have been described for the treatment of type-1 diabetes (T1D). See e.g., International patent application publication WO 2007/063075; Robert S. et al., *Diabetes* 2014, 63: 2876-2887; Steidler et al., *Nat. Biotechnol.* 2003, 21(7): 785-789; and Takiishi T. et al., *J. Clin. Invest.* 2012, 122(5): 1717-1725.

However, there is still a need in the art for genetically modified bacterial strains that are stable, constitutively express more than one bioactive polypeptide and are suitable for clinical usage, e.g., for the treatment of T1D. The present disclosure addresses these needs.

SUMMARY

The current disclosure provides genetically modified microorganisms containing chromosomally integrated nucleic acids encoding IL-10 and proinsulin (PINS), methods of preparing such microorganisms, and methods of using such microorganisms. These genetically modified microorganisms can be suitable to human therapy, including but not limited to the treatment of diabetes, e.g., T1D.

Microorganisms and Compositions

The present disclosure provides microorganisms, e.g., Gram-positive bacteria, such as a lactic acid bacterium (LAB) containing an exogenous nucleic acid encoding an interleukin-10 (IL-10) polypeptide, and an exogenous nucleic acid encoding a T1D-specific antigen, such as proinsulin (PINS) polypeptide, wherein the exogenous nucleic acid encoding the IL-10 polypeptide and the exogenous nucleic acid encoding the T1D-specific antigen (e.g., PINS polypeptide) are both chromosomally integrated, i.e., are integrated into (or located on) the bacterial chromosome.

The microorganism can be a Gram-positive bacterium, such as an LAB. The LAB can be a *Lactococcus* species bacterium. In other embodiments, the LAB is a *Lactobacillus* species, or a *Bifidobacterium* species. In some embodiments, the LAB can be *Lactococcus lactis*. The LAB can be *Lactococcus lactis* subspecies *cremoris*. Another exemplary LAB is a *Lactococcus lactis* strain MG1363. See, e.g., Gasson, M. J., *J. Bacteriol.* 1983, 154: 1-9.

In some examples according to any of the above embodiments, the IL-10 polypeptide is human IL-10 (hIL-10). In other examples, the IL-10 is an IL-10 variant polypeptide, e.g., including at least one point mutation, e.g., to increase expression of the IL-10 polypeptide by the bacterium. In some examples according to these embodiments the IL-10 is "mature" human IL-10 (hIL-10), i.e. without its signal peptide. In some embodiments, the hIL-10 comprises a proline (Pro) to alanine (Ala) substitution, at position 2, when counting the amino acids in the mature peptide. See, e.g., SEQ ID NO: 1. Such polypeptides are described, e.g., in Steidler et al., *Nat. Biotechnol.* 2003, 21(7): 785-789, the disclosure of which incorporated herein by reference in its entirety. In some examples, the IL-10 polypeptide is wild-type human IL-10. In other examples, the IL-10 polypeptide is wild-type human IL-10 without its own signal peptide and has an amino acid sequence at least 90%, at least 92%, at least 95%, at least 96%, at least 97%, at least 98%, or at least 99% identical to SEQ ID NO: 1. In other examples, the exogenous nucleic acid encoding the IL-10 polypeptide has a nucleotide sequence at least 90%, at least 92%, at least 95%, at least 96%, at least 97%, at least 98%, or at least 99% identical to SEQ ID NO: 2.

In some examples according to any of the above embodiments, the T1D-specific antigen polypeptide is a PINS polypeptide, such as human PINS (hPINS), e.g., wild-type human PINS. In some examples, the PINS polypeptide has an amino acid sequence at least 90%, at least 92%, at least 95%, at least 96%, at least 97%, at least 98%, or at least 99% identical to SEQ ID NO: 5. The wild-type PINS may be encoded by a nucleotide sequence that is at least 90%, at least 92%, at least 95%, at least 96%, at least 97%, at least 98%, or at least 99% identical to SEQ ID NO: 6 or SEQ ID NO: 7. In other examples, the PINS polypeptide is human PINS without its signal peptide and has an amino acid sequence that is at least 90%, at least 92%, at least 95%, at least 96%, at least 97%, at least 98%, or at least 99% identical to SEQ ID NO: 3. In other examples, the exogenous nucleic acid encoding the PINS polypeptide has a nucleotide sequence at least 90%, at least 92%, at least 95%, at least 96%, at least 97%, at least 98%, or at least 99% identical to SEQ ID NO: 4.

In some examples according to any of the above embodiments, the microorganism, (e.g., LAB) expresses (e.g., constitutively expresses) the IL-10 polypeptide. In other examples, the microorganism (e.g., LAB) constitutively expresses and secretes the IL-10 polypeptide (e.g., hIL-10). In other examples according to any of the above embodiments, the LAB constitutively expresses the T1D-specific antigen polypeptide (e.g., PINS polypeptide). In other examples, the microorganism (e.g., LAB) constitutively expresses and secretes the T1D-specific antigen (e.g., PINS) polypeptide. In yet other examples, the microorganism (e.g., LAB) constitutively expresses and secretes the IL-10 polypeptide (e.g., hIL-10) and the T1D-specific antigen (e.g., PINS) polypeptide (e.g., hPINS).

In some examples according to any of the above embodiments, the exogenous nucleic acid encoding the IL-10 polypeptide is positioned 3' of an hllA promoter (PhllA), such as a *Lactococcus lactis* PhllA. In some examples according to this embodiment, the exogenous nucleic acid encoding the IL-10 polypeptide is transcriptionally regulated by the PhllA. In other examples, the LAB includes an IL-10 expression cassette containing a PhllA promoter (e.g., a *Lactococcus lactis* PhllA), an IL-10 secretion sequence (e.g., positioned 3' of the PhllA), and the exogenous nucleic acid encoding the IL-10 polypeptide (e.g., positioned 3' of the IL-10 secretion sequence). In some examples, the IL-10 expression cassette is chromosomally integrated. In some examples, the IL-10 expression cassette is chromosomally integrated thereby replacing or partially replacing another gene. In some examples according to this embodiment, the IL-10 expression cassette is chromosomally integrated at the thyA locus, e.g., replacing an endogenous thyA gene, e.g., as described in Steidler et al., *Nat. Biotechnol.* 2003, 21(7): 785-789. In some examples according to any of the above embodiments, the IL-10 secretion sequence is a nucleotide sequence encoding a secretion leader of unidentified secreted 45-kDa protein (Usp45). Such secretion sequence is referred to herein as SSusp45. In some examples, SSusp45 has an amino acid sequence that is at least 90%, at least 92%, at least 95%, at least 96%, at least 97%, at least 98%, or at least 99% identical to SEQ ID NO: 10. In other examples, SSusp45 is encoded by a nucleic acid sequence that is at least 90%, at least 92%, at least 95%, at least 96%, at least 97%, at least 98%, or at least 99% identical to SEQ ID NO: 11 or SEQ ID NO: 12. In some examples SSusp45 in the IL-10 expression cassette is encoded by a nucleic acid sequence that is at least 90%, at least 92%, at least 95%, at least 96%, at least 97%, at least 98%, or at least 99% identical to SEQ ID NO: 11. In some examples, the IL-10 expression cassette is illustrated by: PhllA>>SSusp45>>hIL-10. The nucleotide sequence of an exemplary IL-10 expression cassette is depicted in FIG. 11.

In some examples according to any of the above embodiments, the exogenous nucleic acid encoding the T1D-specific antigen (e.g., PINS) polypeptide is positioned 3' of a gapB promoter, e.g., a gapB promoter that is endogenous to the microorganism (e.g., LAB). In other examples according to this embodiment, the exogenous nucleic acid encoding the T1D-specific antigen (e.g., PINS) polypeptide is transcriptionally regulated by the gapB promoter. In other examples, the exogenous nucleic acid encoding the T1D-specific antigen (e.g., PINS) polypeptide is positioned 3' of a gapB gene (gapB) and its gapB promoter. In other examples, the LAB comprises a first polycistronic expression cassette (e.g., a dual cistron) comprising a gapB promoter positioned 5' of a gapB gene, a T1D-specific antigen secretion sequence (e.g., PINS secretion sequence) (e.g., positioned 3' of the gapB), and the exogenous nucleic acid encoding the T1D-specific antigen (e.g., PINS) polypeptide (e.g., 3' of the PINS secretion sequence). In some examples according to this embodiment, the polycistronic expression cassette further includes an intergenic region, e.g., between the gapB and the PINS secretion sequence. In some examples according to any of the above embodiments, the gapB promoter and the gapB gene are endogenous to the microorganism (e.g., LAB). In some examples, the PINS secretion sequence is SSusp45. In other examples according to the above embodiments, the first polycistronic expression cassette is chromosomally integrated. In other examples, the first polycistronic expression cassette is illustrated by: PgapB>>gapB>>intergenic region>>SSusp45>>PINS. In some examples according to any of the above embodiments, the intergenic region in the first polycistronic expression cassette is rpmD gene 5' intergenic region (i.e. the region preceding rpmD). In some examples according to any of the above embodiments, the rpmD has a nucleotide sequence according to SEQ ID NO: 8 (which includes a stop codon of the first gene, and a start codon of a second gene). Without the start and stop codons, the intergenic region rpmD has a nucleic acid sequence according to SEQ ID NO: 9.

In some examples according to any of the above embodiments, the microorganism (e.g., LAB) further comprises an exogenous nucleic acid encoding a trehalose-6-phosphate phosphatase, e.g., otsB, such as *Escherichia coli* otsB. In some examples according to these embodiments, the exogenous nucleic acid encoding the trehalose-6-phosphate phosphatase is chromosomally integrated. In some examples, the exogenous nucleic acid encoding the trehalose-6-phosphate phosphatase is chromosomally integrated 3' of unidentified secreted 45-kDa protein gene (usp45). In some examples according to this embodiment, the LAB comprises a second polycistronic expression cassette comprising a usp45 promoter, the usp45 gene (e.g., 3' of the promoter), and the exogenous nucleic acid encoding a trehalose-6-phosphate phosphatase (e.g., 3' of the usp45 gene). In some examples, the second polycistronic expression cassette further comprises an intergenic region between the usp45 gene and the exogenous nucleic acid encoding a trehalose-6-phosphate phosphatase. In some examples, the second polycistronic expression cassette is illustrated by: Pusp45>>usp45>>intergenic region>>otsB. In some examples according to these embodiments, the intergenic region is rpmD as described herein above (e.g., having SEQ ID NO: 8 or SEQ ID NO: 9). The second polycistronic expression cassette may then be illustrated by: Pusp45>>usp45>>rpmD>>otsB.

In some examples according to any of the above embodiments, a trehalose-6-phosphate phosphorylase gene (trePP) is disrupted or inactivated in the microorganism (e.g., LAB). For example, the trePP has been inactivated by removing the trePP gene or a fragment thereof, or the trePP has been disrupted by inserting a stop codon. Thus, in some examples according to these embodiments, the microorganism (e.g., LAB) lacks trePP activity.

In other examples according to any of the above embodiments, a cellobiose-specific PTS system IIC component gene (ptcC) has been disrupted or inactivated in the microorganism (e.g., LAB). For example, the ptcC has been disrupted by inserting a stop codon, or ptcC has been inactivated by removing the ptcC or a fragment thereof. Thus, in some examples according to these embodiments, the microorganism (e.g., LAB) lacks ptcC activity.

In other examples according to any of the above embodiments, the LAB further comprises one or more genes encoding one or more trehalose transporter(s). In some examples, the one or more genes encoding the one or more trehalose transporter(s) are endogenous to the LAB. In some examples, the LAB overexpresses the one or more genes encoding the one or more trehalose transporter(s). In some examples according to these embodiments, the one or more genes encoding the one or more trehalose transporter(s) is positioned 3' of an exogenous promoter, e.g., an hllA promoter (PhllA). For example, the one or more genes encoding the one or more trehalose transporter(s) are transcriptionally regulated by the PhllA. In some examples according to these embodiments, the one or more genes encoding the one or more trehalose transporter(s) is selected from llmg_0453, llmg_0454, and any combination thereof. In some examples, llmg_0453 and llmg_0454 are transcriptionally regulated by a PhllA.

In some examples, according to any of the above embodiments, the one or more genes encoding one or more trehalose transporter(s) comprises two genes encoding two trehalose transporters, wherein an intergenic region is located between the two genes. In some examples, the intergenic region is rpmD, e.g., having SEQ ID NO: 8 or SEQ ID NO: 9. In some examples, the microorganism (e.g., LAB) comprises a polycistronic expression cassette comprising two nucleic acid sequences (e.g., genes) encoding two different trehalose transporters (transporter 1 and transporter 2 sequences) and an intergenic region between the two nucleic acids encoding the two different trehalose transporters. Such expression cassette may be illustrated by: PhllA>>transporter 1>>intergenic region>>transporter 2. In some examples according to these embodiments, the intergenic region is rpmD as described herein above (e.g., having SEQ ID NO: 8 or SEQ ID NO: 9). The polycistronic expression cassette may then be illustrated by: PhllA>>transporter1>>rpmD>>transporter2.

Thus, in some embodiments, the LAB comprises, in a single strain, several useful features. In one embodiment, the LAB is *Lactococcus lactis*, comprising:
(A) a chromosomally integrated promoter>>secretion signal>>>therapeutic protein, such as an interleukin, antigen, or enzyme;
(B) a chromosomally-integrated promoter>>secretion signal>>optional second therapeutic protein.
(C) a combination of mutations and insertions to promote trehalose accumulation, which enhances LAB survivability against bile salts and drying. The mutations are selected from
  (i) chromosomally-integrated trehalose transporter(s), such as PhllA>>transporter 1>>intergenic region>>transporter 2, such as llmg_0453 and/or llmg_0454, for uptake of trehalose;
  (ii) chromosomally-integrated Trehalose-6-phosphate phosphatase gene (otsB; Gene ID: 1036914) positioned downstream of usp45 (Gene ID: 4797218) to facilitate conversion of trehalose-6-phosphate to trehalose;
  (iii) inactivated (e.g. through gene deletion) Trehalose-6-phosphate phosphorylase gene (trePP; Gene ID: 4797140); and
  (iv) inactivated cellobiose-specific PTS system IIC component (Gene ID: 4796893), ptcC, (e.g. tga at codon position 30 of 446; tga30).

The LAB may also contain an auxotrophic mutation for biological containment, such as thyA.

In one embodiment, the LAB is *Lactococcus lactis*, comprising:
(A) a chromosomally integrated promoter>>secretion signal>>hIL-10 to secrete mature hIL-10 from LAB, such as PhllA>>SSusp45>>hIL-10;
(B) a chromosomally-integrated promoter>>secretion signal>>PINS, to secrete mature PINS from LAB; such as PgapB>>gapB>>intergenic region>>SSusp45>>PINS. The intergenic region could be, for example, rpmD;
(C) a combination of mutations and insertions to promote trehalose accumulation, which enhances LAB survivability against bile salts and drying. The mutations are selected from
  (i) chromosomally-integrated trehalose transporter(s), such as PhllA>>transporter 1>>intergenic region>>transporter 2, such as llmg_0453 and/or llmg_0454, for uptake of trehalose;
  (ii) chromosomally-integrated Trehalose-6-phosphate phosphatase gene (otsB; Gene ID: 1036914) positioned downstream of usp45 (Gene ID: 4797218) to facilitate conversion of trehalose-6-phosphate to trehalose;
  (iii) inactivated (e.g. through gene deletion) Trehalose-6-phosphate phosphorylase gene (trePP; Gene ID: 4797140); and
  (iv) inactivated cellobiose-specific PTS system IIC component (Gene ID: 4796893), ptcC, (e.g. tga at codon position 30 of 446; tga30).

The LAB may also contain an auxotrophic mutation for biological containment, such as thyA.

In one embodiment, the LAB is *Lactococcus lactis*, with
(A) thyA mutation, for biological containment
(B) a chromosomally integrated PhllA>>SSusp45>>hIL-10 to secrete mature hIL-10 from LAB;
(C) a chromosomally-integrated PgapB>>gapB>>intergenic region>>SSusp45>>PINS, wherein the intergenic region is selected from rpmD, to secrete mature PINS from LAB;
(D) chromosomally-integrated trehalose transporter(s), such as PhllA>>transporter 1>>intergenic region>>transporter 2, such as llmg_0453 and/or llmg_0454, for uptake of trehalose;
(E) inactivated (e.g. through gene deletion) Trehalose-6-phosphate phosphorylase gene (trePP; Gene ID: 4797140);
(F) chromosomally integrated Trehalose-6-phosphate phosphatase gene (otsB; Gene ID: 1036914) (positioned downstream of usp45 (Gene ID: 4797218) to facilitate conversion of trehalose-6-phosphate to trehalose; and
(G) inactivated cellobiose-specific PTS system IIC component (Gene ID: 4796893), ptcC, (e.g. tga at codon position 30 of 446; tga30).

The present disclosure further provides compositions containing a microorganism (e.g., an LAB) as described herein, e.g., a microorganism (e.g., LAB) in accordance with any of the above embodiments.

The present disclosure further provides pharmaceutical compositions containing a microorganism (e.g., LAB) as described herein, e.g., a microorganism (e.g., LAB) in accordance with any of the above embodiments, and further containing a pharmaceutically acceptable carrier.

The present disclosure further provides a microbial suspension (e.g., bacterial suspension) containing a microorganism (e.g., LAB) in accordance with any of the above embodiments, and further containing a solvent, and a stabilizing agent. In some examples according to this embodiment, the solvent is selected from water, oil, and any combination thereof. For example, the present disclosure provides a bacterial suspension containing an LAB of the present disclosure, an aqueous mixture (e.g., a drink), and a stabilizing agent. Exemplary stabilizing agents are selected from a protein or polypeptide (e.g., glycoprotein), a peptide, a mono-, di- or polysaccharide, an amino acid, a gel, a fatty acid, a polyol (e.g., sorbitol, mannitol, or inositol), a salt (e.g., an amino acid salt), or any combination thereof.

The present disclosure further provides a microorganism as described herein (e.g., an LAB in accordance with any of the above embodiments), a composition as described herein, or a pharmaceutical composition as described herein, for use in the treatment of type-1 diabetes (T1D).

The present disclosure further provides a microorganism as described herein (e.g., an LAB in accordance with any of the above embodiments), a composition as described herein, or a pharmaceutical composition as described herein, for use in the preparation of a medicament, e.g., for the treatment of a disease, e.g., an autoimmune disease, such as type-1 diabetes (T1D)

Method 1: Methods of Treating Disease

The present disclosure further provides methods for the treatment of T1D in a subject in need thereof. Exemplary methods include administering to the subject a therapeutically effective amount of a microorganism (e.g., LAB) as disclosed herein (e.g., an LAB in accordance with any of the above embodiments), a composition as disclosed herein, or a pharmaceutical composition as disclosed herein. In some examples according to any of these embodiments, the subject is a human, e.g., a human patient. In some examples according to any of these embodiments, the method further comprises administering an immunomodulatory agent (e.g., an anti-CD3 antibody) to the subject. For example, the immuno-modulatory agent (e.g., anti-CD3 antibody) is administered to the subject using a co-therapeutic regimen, i.e., the subject (e.g., human) is concurrently treated with another immune-modulatory agent, such as an anti-CD3 antibody. Thus, in some examples, the present disclosure provides a method for the treatment of T1D in a human subject in need thereof. Exemplary methods include administering to the human subject a therapeutically effective amount of an LAB as disclosed herein (e.g., an LAB in accordance with any of the above embodiments), a composition as disclosed herein, or a pharmaceutical composition as disclosed herein, wherein the human subject is further administered an anti-CD3 antibody (e.g., is concurrently treated with an anti-CD3 antibody) or fragment thereof.

In some examples, the anti-CD3 antibody is a monoclonal antibody. In other examples, the anti-CD3 antibody is a humanized monoclonal antibody. In other examples, the anti-CD3 antibody is otelixizumab or teplizumab. In some examples, when administered as a combination therapy with LAB, the anti-CD3 antibody is administered to the subject in a dose different from that normally used for monotherapy. The optimal dose of anti-CD3 for use in combination therapy may be determined through animal models and clinical trials. Preferably, the dose of anti-CD3 is less than a dose normally required for effective mono-therapy with anti-CD3 antibody, i.e. a subtherapeutic dose. A dose effective for monotherapy may be determined by reference to animal models and clinical trials, and by the practice of those of skill in the art, and may be the regulatory-approved dose. In some examples, the subject undergoing combination therapy with LAB is administered a dose of anti-CD3 that is at least about 10%, at least about 20%, at least about 30%, at least about 40%, at least about 50%, at least about 60%, at least about 70%, at least about 80%, or at least about 90% less than the standard dose of anti-CD3 in monotherapy. In other examples, the dose of anti-CD3 administered in combination therapy is about 10-100% less, about 10-90% less, about 10-70% less, about 10-60% less, about 10-50% less, about 50-100% less, or about 20-50% less than the dose of anti-CD3 in monotherapy. Experiments have shown that 6 daily doses of 48 or 64 mg of otelixizumab can suppress T-cell activity enough that, at 36 months, the treatment group retained 80% more beta cell function than placebo control. However, such a dose was associated with reactivation of latent Epstein-Barr infection. A 3.1 mg/day dose for 8 days did not preserve beta-cell function. Therefore, a treatment at least 10% less than 48 mg (i.e. 43 mg) would be considered "subtherapeutic."

In some embodiments, the mammalian subject in the above methods, has recently been diagnosed with T1D (i.e., has recent-onset T1D). In some examples according to these embodiments, the subject has been diagnosed with T1D within the previous 12 months, the previous 24 months, or the previous 36 months prior to administering the microorganism (e.g., LAB).

In some examples according to any of the embodiments of Method 1, the method further includes measuring a clinical marker (e.g., an immune biomarker) in the subject, e.g., the subject's organ or blood. For example, the method may further include measuring a T1D-related antibody in the subject's blood. In some examples, the method can further include measuring insulin autoantibody (IAA) in the subject's blood. In some examples, the amount of IAA in the subject's blood is indicative of T1D disease progression, e.g., whether the subject can be classified as having recent-onset T1D, and may be indicative of whether the subject will likely benefit from treatment. Thus, measuring IAA may occur prior to administering the microorganism to the subject. In some examples, IAA positivity at disease onset is predictive of positive therapeutic outcome. However, measuring IAA may also be used to monitor and measure the outcome of the treatment, and may therefore be used during treatment (e.g., throughout the treatment period in intervals) to monitor treatment efficacy or outcome and/or subsequent to the treatment period, e.g., to monitor whether the subject maintains treatment results (e.g., normoglycemia) after treatment has stopped. In some examples, decline of IAA positivity is indicative of a positive therapeutic outcome. In other examples, the method further includes measuring regulatory T cells in the subject. Regulatory T cells include Treg17, Tr1 Th3, CD8±CD28$^-$, Qa-1 restricted T cells, CD4$^+$Foxp3$^+$CD25$^+$ and/or CD4$^+$Foxp3$^+$CD25$^-$ T cells. Preferably, CD4$^+$Foxp3$^+$CD25$^+$ and/or CD4$^+$Foxp3$^+$CD25$^-$ T cells. In other examples, the method further includes measuring an initial blood glucose concentration in the subject. In other examples, the method further includes measuring C-peptide levels in the subject.

In related embodiments, the invention is a method of increasing the activity of Treg cells to suppress the autoimmune response to beta cells and/or a T1D-associated antigen, preferably suppressing the autoimmune response to all T1D-associated antigens. In other embodiments, the invention is a method of substantially decreasing, preferably halting, the autoimmune response to beta cells and/or any T1D-associated antigen. Preferably, the substantial decrease in the autoimmune response leads to a substantial decrease or halting of the disease progress.

In some embodiments in any of the above methods, the microorganism (e.g., LAB) is administered to the subject orally. For example, the microorganism (e.g., LAB) is administered to the subject in the form of a pharmaceutical composition for oral administration (e.g., a capsule, tablet, granule, or liquid) comprising the microorganism (e.g., LAB) and a pharmaceutically acceptable carrier. In other examples, the microorganism (e.g., LAB) is administered to the subject in the form of a food product, or is added to a food (e.g., a drink). In other examples, the microorganism (e.g., LAB) is administered to the subject in the form of a dietary supplement. In yet other examples, the microorganism (e.g., LAB) is administered to the subject in the form of a suppository product. In some examples, the compositions of the present disclosure are adapted for mucosal delivery of the polypeptides, which are expressed by the microorganism (e.g., LAB). For example, compositions may be formulated for efficient release in the gastro-intestinal tract (e.g., gut) of the subject.

In accordance with any of the above embodiments, the present disclosure further provides methods for establishing tolerance to a T1D-specific antigen (e.g., PINS) polypeptide in a subject in need thereof. Exemplary methods include administering to the subject a therapeutically effective amount of a microorganism (e.g., LAB) as disclosed herein (e.g., an LAB in accordance with any of the above embodiments), a composition as disclosed herein, or a pharmaceutical composition as disclosed herein. In some examples according to any of these embodiments, the subject is a human, e.g., a human patient.

In accordance with any of the above embodiments, the present disclosure further provides methods for decreasing IAA in a subject in need thereof, or for increasing the number of $CD4^+Foxp3^+$ T cells in a subject in need thereof. Exemplary methods include administering to the subject a therapeutically effective amount of a microorganism (e.g., LAB) as disclosed herein (e.g., an LAB in accordance with any of the above embodiments), a composition as disclosed herein, or a pharmaceutical composition as disclosed herein. In some examples according to any of these embodiments, the subject is a human, e.g., a human patient.

In some examples, administering a therapeutically effective amount of a microorganism (e.g., LAB) of the current disclosure and an anti-CD3 antibody of the current disclosure to the subject (e.g., in accordance with any of the above methods), reduces the amount of insulin the subject is (i.e., must be) administered to control blood glucose levels or maintain a certain blood glucose level (e.g., as recommended by a physician, or as generally regarded as safe). For example, administering a therapeutically effective amount of a microorganism (e.g., LAB) of the current disclosure and an anti-CD3 antibody of the current disclosure to the subject (e.g., in accordance with any of the above methods), reduces the amount of insulin required to control blood glucose levels or maintain a certain blood glucose level in a subject when compared to the amount of insulin required by a corresponding subject not being administered the microorganism (e.g., LAB) and the anti-CD3 antibody, or when compared to the amount of insulin required by a corresponding subject treated with anti-CD3 antibody alone.

In other examples, administering a therapeutically effective amount of a microorganism (e.g., LAB) of the current disclosure and an anti-CD3 antibody of the current disclosure to the subject (e.g., in accordance with any of the above methods), preserves beta-cell function in a subject (e.g., preserves the beta-cell function measured at the beginning of treatment) in a subject, e.g., as measured using art recognized methods. Exemplary methods for measuring beta-cell function (e.g., using C-peptide levels) are also described herein. In some examples, beta-cell function in the subject is preserved for at least about 2 months, at least about 4 months, at least about 6 months, at least about 8 months, at least about 10 months, at least about 12 months, at least about 14 months, at least about 16 months, at least about 18 months, at least about 20 months, at least about 22 months, or at least about 24 months after administration of the microorganism (e.g., LAB) and the anti-CD3 antibody began. In other examples, administering a therapeutically effective amount of a microorganism (e.g., LAB) of the current disclosure and an anti-CD3 antibody of the current disclosure to the subject (e.g., in accordance with any of the above methods), increases the time in which beta-cell function is preserved in the subject, when compared to the time in which beta-cell function is preserved in a corresponding subjects not being administered the microorganism (e.g., LAB) and the anti-CD3 antibody, or when compared to a corresponding subject treated with anti-CD3 antibody alone.

In other examples, administering a therapeutically effective amount of a microorganism (e.g., LAB) of the current disclosure and an anti-CD3 antibody of the current disclosure to the subject (e.g., in accordance with any of the above methods), maintains normal glycemia in a subject, e.g., as measured using art recognized methods. Blood glucose ranges correlating with normal glycemia are described herein. For example, normal glycemia in a human subject may be correlated with two consecutive fasting blood glucose measurements of 126 mg/dL or less. Exemplary methods for measuring blood glucose levels are known in the art and are described herein. In some examples, normal glycemia in the subject (undergoing treatment) is preserved for at least about 2 months, at least about 4 months, at least about 6 months, at least about 8 months, at least about 10 months, at least about 12 months, at least about 14 months, at least about 16 months, at least about 18 months, at least about 20 months, at least about 22 months, or at least about 24 months after administration of the microorganism (e.g., LAB) and the anti-CD3 antibody began. In other examples, administering a therapeutically effective amount of a microorganism (e.g., LAB) of the current disclosure and an anti-CD3 antibody of the current disclosure to the subject (e.g., in accordance with any of the above methods), increases the time in which normal glycemia is maintained in the subject, when compared to the time normal glycemia is maintained in a corresponding subject not being administered the microorganism (e.g., LAB) and the anti-CD3 antibody, or when compared to the time normal glycemia is maintained in a corresponding subject treated with anti-CD3 antibody alone.

In other examples, administering a therapeutically effective amount of a microorganism (e.g., LAB) of the current disclosure and an anti-CD3 antibody of the current disclosure to the subject (e.g., in accordance with any of the above methods), maintains a normal hemoglobin A1c (HbA1c) level in a subject, e.g., as measured using art recognized methods. In some examples, normal HbA1c level in the subject (undergoing treatment) is maintained for at least about 2 months, at least about 4 months, at least about 6 months, at least about 8 months, at least about 10 months, at least about 12 months, at least about 14 months, at least about 16 months, at least about 18 months, at least about 20 months, at least about 22 months, or at least about 24 months after administration of the microorganism (e.g., LAB) and the anti-CD3 antibody.

In an alternative embodiment, the therapeutic method of the invention ameliorates the disease, such that in treated subjects the degree and frequency of hyperglycemia is reduced compared with untreated subjects. Such reduction may be 10, 20, 30, 40, 50, 60, 70, 80 or 90% of the untreated subjects.

Untreated T1D develops over time and becomes progressively worse as beta cells in the pancreas are destroyed. Thus, as the present method can halt disease, it is advantageous to treat subjects as early as possible in the disease progression. Such markers of disease progression include, without limitation, glycemic index, insulin autoantibody (IAA) levels, fragment C levels, and insulitis. Thus, in a related embodiment, the therapeutic method of the invention also includes measuring disease progression prior to therapy, and during therapy.

For example, a human subject may be categorized as having early onset T1D when any one of the following is measured in the subject: (1) two consecutive fasting blood glucose tests are equal to or greater than 126 mg/dL; (2) when any random blood glucose measurement is greater than 200 mg/dL; (3) a hemoglobin A1c (HbA1c) test that is equal to or greater than 6.5 percent (HbA1c is a blood test that gives a three month average of blood sugars); or (4) a two-hour oral glucose tolerance test with any value over 200 mg/dL, or combinations thereof. Thus, normal glycemia may be characterized by any of the following: (1) two consecutive fasting blood glucose tests are below 126 mg/dL, below 120 mg/dL, or below 100 mg/dL; (2) when any random blood glucose measurement is below 200 mg/dL, below 180 mg/dL, below 160 mg/dL, or below 140 mg/dL; (3) a hemoglobin A1c (HbA1c) test that is less than 6.5 percent, or less than 6%; or (4) a two-hour oral glucose tolerance test with a value below 200 mg/dL, below 180 mg/dL, below 160 mg/dL, or below 140 mg/dL, or any combination thereof.

Once disease progression is substantially decreased (and preferably ceased, especially with regard to autoimmunity that underlies the pathogenic process), a subject may be further treated by methods to restore beta cell function. Thus in a further embodiment, the subject may be treated with a beta-cell transplant, and/or with drugs to cause the proliferation of endogenous beta cells. Because the method is able to reverse the autoimmunity that underlies T1D, the method is not limited to early onset diabetes. Once the beta-cell destroying autoimmunity is eliminated, beta cell function can be restored through transplantation, and/or by encouraging the growth and development of endogenous beta cells. Thus, the method can be applied to subjects with chronic diabetes.

In a further embodiment, the therapeutic method of the invention ameliorates disease progression, such that the rate of worsening is three quarters, half, one quarter or less that of the untreated disease. Such worsening may be assessed through glycemic index, insulin autoantibody (IAA) levels, fragment C levels, and insulitis, for example.

In a further embodiment, the therapeutic method of the invention is given to prevent T1D, such as by administration prior to any clinical symptoms. Preferably, the subject is identified as having T1D risk factors, including family history, elevated (but not diabetic) sugar levels in blood and urine, and antibodies to T1D associated antigens, and by a progressive worsening of these markers over time.

Method 2: Method of Preparing a Genetically-Modified Organism for Treatment of T1D The current disclosure further provides methods for preparing a genetically modified microorganism (e.g., an LAB as disclosed herein. Exemplary methods include (i) contacting a microorganism (e.g., LAB) with an exogenous nucleic acid encoding an IL-10 polypeptide; and (ii) contacting the microorganism (e.g., LAB) with an exogenous nucleic acid encoding a T1D-specific antigen (e.g., PINS) polypeptide, wherein the exogenous nucleic acid encoding the IL-10 polypeptide and the exogenous nucleic acid encoding the T1D-specific antigen (e.g., PINS) polypeptide are chromosomally integrated (i.e., integrated into the chromosome of the microorganism, e.g., LAB). When the nucleic acids are integrated into the microbial (e.g., bacterial) genome, e.g. in the chromosome, the genetically modified microorganism (e.g., LAB) is formed. The microorganism (e.g., LAB) subjected to the genetic modification of the current method can be any microbial strain, e.g., can be a wild-type bacterial strain, or can be genetically modified prior to contacting it with the exogenous nucleic acid encoding the IL-10 polypeptide and the exogenous nucleic acid encoding the T1D-specific antigen (e.g., PINS) polypeptide.

In some examples, the above methods employ homologous recombination to integrate the nucleic acids into the microbial (e.g., bacterial) chromosome. Thus, in some examples in accordance with these embodiments, the exogenous nucleic acid encoding the IL-10 polypeptide and the exogenous nucleic acid encoding the T1D-specific antigen (e.g., PINS) polypeptide are chromosomally integrated using homologous recombination (e.g., employing one or more integration plasmid containing the respective nucleic acids). In some examples according to any of these embodiments, contacting the microorganism (e.g., LAB) with an exogenous nucleic acid encoding the IL-10 polypeptide (e.g., an integration plasmid containing the exogenous nucleic acid encoding the IL-10 polypeptide) occurs prior to contacting the LAB with an exogenous nucleic acid encoding the T1D-specific antigen (e.g., PINS) polypeptide (e.g., an integration plasmid containing the exogenous nucleic acid encoding the PINS polypeptide). In other examples according to any of these embodiments, contacting the microorganism (e.g., LAB) with an exogenous nucleic acid encoding the IL-10 polypeptide (e.g., an integration plasmid containing the exogenous nucleic acid encoding the IL-10 polypeptide) occurs subsequent to contacting the LAB with an exogenous nucleic acid encoding the T1D-specific antigen (e.g., PINS) polypeptide (e.g., an integration plasmid containing the exogenous nucleic acid encoding the PINS polypeptide). In yet other examples according to any of these embodiments, the microorganism (e.g., LAB) is contacted concurrently with an exogenous nucleic acid encoding the IL-10 polypeptide (e.g., an integration plasmid containing the exogenous nucleic acid encoding the IL-10 polypeptide) and an exogenous nucleic acid encoding the T1D-specific antigen (e.g., PINS) polypeptide (e.g., an integration plasmid containing an exogenous nucleic acid encoding a PINS polypeptide), or a exogenous nucleic acid encoding both hIL-10 and PINS.

In some examples according to any of these embodiments, the method further includes combining a culture of the genetically modified microorganism (e.g., LAB) with at least one stabilizing agent (e.g., a cryopreserving agent) to form a microbial (e.g., bacterial) mixture. In some examples, the method further includes removing water from the microbial (e.g., bacterial) mixture forming a dried composition. For example, the method can further include freeze-drying the microbial (e.g., bacterial) mixture to form a freeze-dried composition. In other examples, the method may further include combining the genetically modified microorganism (e.g., LAB) or the dried composition (e.g., the freeze-dried composition) with a pharmaceutically acceptable carrier to form a pharmaceutical composition. The method may further include formulating the dried composition (e.g., the freeze-dried composition) or the pharmaceutical composition into a pharmaceutical dosage form.

The current disclosure further provides a genetically modified microorganism (e.g., a genetically modified LAB) prepared by a method described herein (e.g., a method in accordance with any of the above embodiments of Method 2).

Method 3: Method of Preparing a Pharmaceutical Composition

The disclosure further provides methods for preparing a pharmaceutical composition. Exemplary methods include contacting a culture of a microorganism (e.g., LAB) as disclosed herein (e.g., an LAB in accordance with any of the above embodiments) with at least one stabilizing agent (e.g., a cryopreserving agent), thereby forming a microbial (e.g., bacterial) mixture. In some examples, the at least one stabilizing agent comprises at least one cryopreserving agent. In some examples, the microorganism (e.g., LAB) contains an exogenous nucleic acid encoding an interleukin-10 (IL-10) polypeptide, and further contains an exogenous nucleic acid encoding a T1D-specific antigen (e.g., PINS) polypeptide, wherein the exogenous nucleic acid encoding the IL-10 polypeptide and the exogenous nucleic acid encoding the T1D-specific antigen (e.g., PINS) polypeptide are both chromosomally integrated, i.e., are integrated into (or located on) the microbial (e.g., bacterial) chromosome.

Such methods may further include removing water from the microbial (e.g., bacterial) mixture, thereby forming a dried composition. For example, the methods may include freeze-drying the microbial (e.g., bacterial) mixture thereby forming a freeze-dried composition.

In some examples according to any of the above embodiments of Method 3, the method further includes contacting the dried composition (e.g., the freeze-dried composition) with a pharmaceutically acceptable carrier forming a pharmaceutical composition. The methods may further include formulating the dried composition (e.g., freeze-dried composition) into a pharmaceutical dosage form, such as a tablet, a capsule, or a sachet.

Unit Dosage Forms

Accordingly, the present disclosure further provides a unit dosage form comprising a microorganism (e.g., LAB) of the present disclosure, a dried composition of the present disclosure (e.g., a freeze-dried composition of the present disclosure), or a pharmaceutical composition of the present disclosure. In some examples, the unit dosage form is an oral dosage form, such as a tablet, a capsule (e.g., a capsule containing a powder or containing micro-pellets or micro-granules), a granule, or a sachet (e.g., containing dried bacteria for suspension in a liquid for oral administration). In some embodiments, the non-pathogenic microorganism (e.g., LAB) contained in the dosage form is in a dry-powder form or compacted version thereof.

In some examples according to these embodiments, the unit dosage form contains from about $1 \times 10^4$ to about $1 \times 10^{12}$ colony-forming units (cfu) of the microorganism (e.g., LAB). In other examples, the unit dosage form contains from about $1 \times 10^6$ to about $1 \times 10^{12}$ colony forming units (cfu) of the microorganism (e.g., LAB). In other examples, the unit dosage form contains from about $1 \times 10^8$ to about $1 \times 10^{11}$ cfu. In yet other examples, the unit dosage form contains about $1 \times 10^9$ to about $1 \times 10^{12}$ cfu.

Kits

The current disclosure further provides kits containing (1) a microorganism (e.g., LAB) according to any of the embodiments disclosed herein, a composition containing a microorganism (e.g., LAB) according to any of the embodiments described herein, a pharmaceutical composition containing a microorganism (e.g., LAB) according to any of the embodiments described herein, or a unit dosage form containing a microorganism (e.g., LAB) according to any of the embodiments described herein; and (2) instructions for administering the microorganism (e.g., LAB), the composition, the pharmaceutical composition, or the unit dosage form to a mammal, e.g., a human (e.g., human patient).

In related embodiments, the kit may further comprise tests for ascertaining the progression of the disease and the success of treatment (e.g., tests for glycemic index, insulin autoantibody (IAA) levels, fragment C levels, and insulitis). The kit may further provide with beta cells for transplantation.

BRIEF DESCRIPTION OF THE DRAWINGS

FIG. 1C is a graph demonstrating that an exemplary antigen-specific therapy according to the present disclosure halts insulitis progression in NOD mice. Insulitis scoring was performed in a blinded manner on paraffin-embedded pancreatic sections of new-onset diabetic and L. lactis-based combination therapy (CT)-treated mice (both responders and non-responders), as indicated, at the end of treatment. Statistical significance between groups was calculated using Mann-Whitney t-test; ** P<0.01.

FIG. 2C is a graph showing that starting glycemia and positivity for IAAs at entry correlated with therapeutic success. New-onset diabetic NOD mice were stratified based on starting glycemia under or above 350 mg/dl and IAA positivity at study entry. Shown is the percentage of mice that were tolerized after therapy.

FIG. 2D depicts graphs showing that change in IAA positivity between pre- and post-therapy was significantly different in therapy responders. Shown is IAA levels at diabetes diagnosis and after L. lactis-based combination treatment follow-up in therapy responders (upper panel) and non-responders (lower panel). Statistical significance between groups was calculated using Mann-Whitney t-test; ** P<0.01. For one mouse the starting level of IAA was 139, outside the y-axis limit, and therefore not shown.

FIG. 7C is a graph showing insulitis scoring in the pancreas of therapy-cured NOD.Foxp3.DTR mice before and after DT treatment.

FIG. 11 is a representation of an exemplary IL-10 expression cassette (SEQ ID NO: 13) comprising an hllA promoter (PhllA), an IL-10 secretion sequence (SSusp45), and an exemplary nucleic acid sequence encoding human IL-10 (and a corresponding amino acid sequence), which sequence is used without its native signal peptide and includes a (Pro to Ala) point mutation at position 2 of the indicated IL-10 sequence (hIL10aPxA). SEQ ID NO: 14 is the amino acid sequence of the IL-10 secretion sequence linked to the human IL-10 sequence.

FIGS. 12A and 12B are collectively a representation of an exemplary PINS polycistronic expression cassette (SEQ ID NO: 15) containing a gapB promoter (PgapB), the gapB gene, an exemplary intergenic region (rpmD), an exemplary PINS secretion sequence (SSusp45) translationally coupled to an exemplary nucleic acid sequence encoding human PINS. SEQ ID NO: 16 is the amino acid sequence encoded by the gapB gene. SEQ ID NO: 17 is the amino acid sequence encoded by the PINS secretion sequence and the translationally coupled human PINS sequence.

FIGS. 13A, 13B, and 13C (SEQ ID NO: 18) are collectively a representation of a deletion of the trehalose-6-phosphate phosphorylase gene (trePP; Gene ID: 4797140); Insertion of the constitutive promoter of the HU-like DNA-binding protein gene (PhllA; Gene ID: 4797353) to precede the putative phosphotransferase genes in the trehalose operon (trePTS; llmg_0453 and llmg_0454; ptsI and ptsII; Gene ID: 4797778 and Gene ID: 4797093 respectively), insertion of the intergenic region preceding the highly expressed *L. lactis* MG1363 50S ribosomal protein L30 gene (rpmD; Gene ID: 4797873) in between ptsI and ptsII.

FIGS. 14A and 14B (SEQ ID NO: 19) are collectively a representation of insertion of trehalose-6-phosphate phosphatase gene (otsB; Gene ID: 1036914) downstream of unidentified secreted 45-kDa protein gene (usp45; Gene ID: 4797218). Insertion of the intergenic region preceding the highly expressed *L. lactis* MG1363 50S ribosomal protein L30 gene (rpmD; Gene ID: 4797873) between usp45 and otsB.

FIGS. 15A and 15B (SEQ ID NOS: 20, 21, and 25) are collectively a representation of insertion of tga at codon position 30 of 446 (tga30), alongside with the introduction of an EcoRI restriction site, to disrupt the gene encoding cellobiose-specific PTS system IIC component (ptcC; Gene ID: 4796893).

FIG. 16 (SEQ ID NO: 22) is a representation of insertion of a gene encoding a fusion of usp45 secretion leader (SSusp45) with the pins gene, encoding human proinsulin (PINS; UniProt: P01308, amino acids 25-110), downstream of the highly expressed glyceraldehyde 3-phosphate dehydrogenase gene (gapB; Gene ID: 4797877). Insertion of the intergenic region preceding the highly expressed *L. lactis* MG1363 50S ribosomal protein L30 gene (rpmD; Gene ID: 4797873) between gapB and pins.

FIG. 17 (SEQ ID NO: 23) is a representation of deletion of thymidylate synthase gene (thyA; Gene ID: 4798358). Downstream of the constitutive promoter of the HU-like DNA-binding protein gene (PhllA; Gene ID: 4797353), insertion of a gene encoding a fusion (SEQ ID NO: 24) of SSusp45 with the hil-10 gene, encoding human interleukin-10 (hIL-10; UniProt: P22301, aa 19-178, variant P2A, Steidler et al., *Nat. Biotechnol.* 2003, 21(7): 785-789) is inserted to allow expression and secretion of hIL-10.

DETAILED DESCRIPTION

Figure 1A:
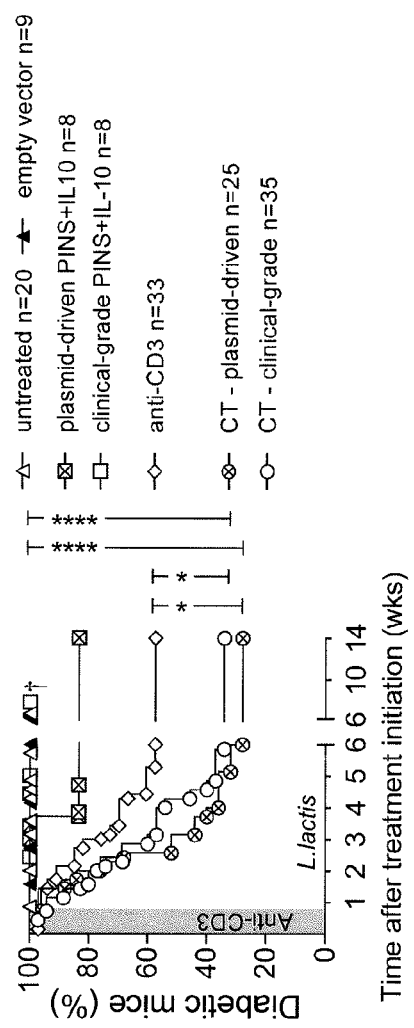
FIG. 1A is a graph demonstrating that an exemplary antigen-specific therapy according to the present disclosure stably reverses new-onset diabetes in NOD mice. New-onset diabetic NOD mice were treated as indicated and blood glucose concentrations were followed up for 14 weeks post-treatment initiation. Shown is the percentage of mice that remained diabetic after treatment. "†" indicates dead or moribund mice. In all Kaplan-Meier survival curves, statistical significance between groups was determined by Mantel-Cox log-rank test; * P<0.05, ****, P<0.0001.

Provided are compositions and methods for the treatment of T1D, and/or for restoring tolerance to T1D-specific antigens (i.e., PINS) in a subject.

Definitions

As used in the specification and embodiments, the singular forms "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "expressing" a gene or polypeptide or "producing" a polypeptide (e.g., an IL-10 polypeptide or T1D-specific antigen polypeptide), or "secreting" a polypeptide is meant to include "capable of expressing" and "capable of producing," or "capable of secreting," respectively. For example, a microorganism, which contains an exogenous nucleic acid can under sufficient conditions (e.g., sufficient hydration and/or in the presence of nutrients) express and secrete a polypeptide encoded by an exogenous nucleic acid. However, the microorganism may not always actively express the encoded polypeptide. The microorganism (e.g., bacterium) may be dried (e.g., freeze-dried), and in that state can be considered dormant (i.e., is not actively producing polypeptide). However, once the microorganism is subjected to sufficient conditions, e.g., is administered to a subject and is released (e.g., in the gastro-intestinal tract of the subject) it may begin expressing and secreting polypeptide. Thus, a microorganism "expressing" a gene or polypeptide, "producing" a polypeptide, or "secreting" a polypeptide of the current disclosure includes the microorganism in its "dormant" state. As used herein, "secrete" means that the protein is exported outside the cell and into the culture medium/supernatant or other extracellular milieu.

As used herein, the term "constitutive" in the context of a promoter (or by extension relating to gene expression or secretion of a polypeptide) refers to a promoter that allows for continual transcription of its associated gene. A constitutive promoter compares to an "inducible" promoter.

The term "about" in relation to a reference numerical value, and its grammatical equivalents as used herein, can include the reference numerical value itself and a range of values plus or minus 10% from that reference numerical value. For example, the term "about 10" includes 10 and any amounts from and including 9 to 11. In some cases, the term "about" in relation to a reference numerical value can also include a range of values plus or minus 10%, 9%, 8%, 7%, 6%, 5%, 4%, 3%, 2%, or 1% from that reference numerical value. In some embodiments, "about" in connection with a number or range measured by a particular method indicates that the given numerical value includes values determined by the variability of that method.

An "IL-10 gene" refers to an interleukin 10 gene encoding an "IL-10 polypeptide." The term "IL-10 gene" includes "IL-10 variant genes" encoding "IL-10 variant polypeptides." The DNA sequence encoding IL-10 in an LAB may be codon optimized to facilitate expression in LAB, and as such may differ from that in the native organism (e.g., humans).

The term "IL-10" or "IL-10 polypeptide" refers to a functional, IL-10 polypeptide (e.g., human IL-10 polypeptide) that has at least the amino acid sequence of the mature form (i.e. without its secretion signal), but also includes membrane-bound forms and soluble forms, as well as "IL-10 variant polypeptides."

An "IL-10 variant" or "IL-10 variant polypeptide" refers to a modified (e.g., truncated or mutated), but functional IL-10 polypeptide, e.g., a truncated or mutated version of human IL-10. The term "IL-10 variant polypeptide" includes IL-10 polypeptides with enhanced activity or diminished activity when compared to a corresponding wild-type IL-10 polypeptide. An "IL-10 variant polypeptide" retains at least some IL-10 activity (functional polypeptide).

The "percentage identity" between polypeptide sequences can be calculated using commercially available algorithms which compare a reference sequence with a query sequence. In some embodiments, polypeptides are 70%, at least 70%, 75%, at least 75%, 80%, at least 80%, 85%, at least 85%, 90%, at least 90%, 92%, at least 92%, 95%, at least 95%, 97%, at least 97%, 98%, at least 98%, 99%, or at least 99% or 100% identical to a reference polypeptide, or a fragment thereof (e.g., as measured by BLASTP or CLUSTAL, or other alignment software) using default parameters. Similarly, nucleic acids can also be described with reference to a starting nucleic acid, e.g., they can be 50%, at least 50%, 60%, at least 60%, 70%, at least 70%, 75%, at least 75%, 80%, at least 80%, 85%, at least 85%, 90%, at least 90%, 95%, at least 95%, 97%, at least 97%, 98%, at least 98%, 99%, at least 99%, or 100% identical to a reference nucleic acid or a fragment thereof (e.g., as measured by BLASTN or CLUSTAL, or other alignment software using default parameters). When one molecule is said to have a certain percentage of sequence identity with a larger molecule, it means that when the two molecules are optimally aligned, the percentage of residues in the smaller molecule finds a match residue in the larger molecule in accordance with the order by which the two molecules are optimally aligned, and the "%" (percent) identity is calculated in accord with the length of the smaller molecule.

The term "chromosomally integrated" or "integrated into a chromosome" or any variation thereof means that a nucleic acid sequence (e.g., gene; open reading frame; exogenous nucleic acid encoding a polypeptide; promoter; expression cassette; and the like) is located on (integrated into) a microbial (e.g., bacterial) chromosome, i.e., is not located on an episomal vector, such as a plasmid. In some embodiments, in which the nucleic acid sequence is chromosomally integrated, the polypeptide encoded by such chromosomally integrated nucleic acid is constitutively expressed.

The terms "self-antigen" or "auto-antigen" are used interchangeably herein. The terms are used herein in accordance with the art recognized meaning of self-antigen or auto-antigen, and generally refer to a polypeptide/protein originating from within a subjects own body (produced by the subject's own body), wherein the antigen is recognized by the subject's own immune system, and typically produces antibodies against such antigen. Autoimmune diseases are generally associated with certain disease-specific self-antigens. For example, in T1D a subject's immune system may produce antibodies against at least one antigen associated with the beta-cell destruction process. Such self-antigens include proinsulin (PINS), glutamic acid decarboxylase (GAD65), insulinoma-associated protein 2 (IA-2), islet-specific glucose-6-phosphatase catalytic subunit-related protein (IGRP) and zinc transporter (ZnT) 8. Clinical T1D may further be associated with additional candidate target molecules expressed by beta-cells such as chromogranin A, (prepro) islet amyloid polypeptide (ppIAPP), peripherin and citrullinated glucose-regulated protein (GRP).

The term "T1D-specific antigen gene" refers to a gene encoding the above "T1D-specific antigen." The term "T1D-specific antigen gene" includes "T1D-specific antigen variant genes" encoding "T1D-specific antigen variant polypeptides." The DNA sequence encoding T1D antigen in an LAB may be codon optimized to facilitate expression in LAB, and as such may differ from that in the native organism (e.g. humans).

The term "T1D-specific antigen polypeptide" refers to a functional, e.g., full-length, polypeptide, as well as "T1D-specific antigen variant polypeptides," which may have enhanced activity or diminished activity when compared to a corresponding wild-type polypeptide The T1D specific antigen may also lack the eukaryotic signal sequences.

The term "T1D-specific antigen variant" or "T1D-specific antigen variant polypeptide" refers to a modified (e.g., truncated or mutated), but functional polypeptide, e.g., a truncated or mutated version of human PINS. The term "variant polypeptide" includes polypeptides with enhanced activity or diminished activity when compared to a corresponding wild-type polypeptide. A "variant polypeptide" retains at least some biological activity (functional polypeptide). Exemplary variants of GAD65 and IA-2 include trimmed versions thereof (e.g., GAD65$_{370-575}$, and IA-2635-979, respectively; relative to NCBI accession numbers NP_000809.1 and NP_002837.1 retaining antigenic properties, and are thus useful in the compositions and methods of the current disclosure, e.g., in stimulating Tregs and inducing tolerance in a subject. Generally, trimmed or truncated versions of a T1D-specific antigen are efficiently expressed and secreted by the microorganism (e.g., *Lactococcus lactis*).

The term "operably linked" refers to a juxtaposition wherein the components described are in a relationship permitting them to function in their intended manner A control sequence "operably linked" to a coding sequence is ligated in such a way that expression of the coding sequence is achieved under condition compatible with the control sequences. For example, a promoter is said to be operably linked to a gene, open reading frame or coding sequence, if the linkage or connection allows or effects transcription of said gene. In a further example, a 5' and a 3' gene, cistron, open reading frame or coding sequence are said to be operably linked in a polycistronic expression unit, if the linkage or connection allows or effects translation of at least the 3' gene. For example, DNA sequences, such as, e.g., a promoter and an open reading frame, are said to be operably linked if the nature of the linkage between the sequences does not (1) result in the introduction of a frameshift mutation, (2) interfere with the ability of the promoter to direct the transcription of the open reading frame, or (3) interfere with the ability of the open reading frame to be transcribed by the promoter region sequence.

Anti-CD3 Antibody

An "anti-CD3 antibody" can be any antibody that binds to a CD3 receptor on the surface of a T cell, e.g., an antibody that targets the epsilon chain of CD3 (CD3E). The term "anti-CD3 antibody" includes any fragment of such antibody, such as Fab fragments, single domain antibodies, nanobodies and the like. In some examples, the anti-CD3 antibody or fragment thereof is a monoclonal antibody. In other examples, the anti-CD3 antibody is a humanized monoclonal antibody, e.g., a chimeric or humanized hybrid antibody. In some examples, the anti-CD3 antibody is a single domain antibody or nanobody. In other examples, the anti-CD3 antibody is muromonab-CD3. Other known monoclonal anti-CD3 antibodies include otelixizumab, teplizumab and visilizumab, and fragments thereof. These antibodies are being investigated for the treatment of conditions like Crohn's disease, ulcerative colitis and type 1 diabetes (see, e.g., Herold K. C. and Taylor L.; "Treatment of Type 1 diabetes with anti-CD3 monoclonal antibody: induction of immune regulation?". *Immunologic Research* 2003, 28 (2): 141-50) and for inducing immune tolerance. See, e.g., Bisikirska et al. "TCR stimulation with modified anti-CD3 mAb expands CD8+ T cell population and induces CD8+ CD25+ Tregs" (2005), and Bisikirska et al., "Use of Anti-CD3 Monoclonal Antibody to Induce Immune Regulation in Type 1 Diabetes". *Annals of the New York Academy of Sciences* 2004, 1037: 1-9. In some examples, the anti-CD3 antibody blocks the function of effector T cells (e.g., which attack and destroy insulin-producing beta-cells) and/or stimulates regulatory T cells. Thus, in some examples, the anti-CD3 antibody protects a subject against effector T cell damage, e.g., preserving the ability of beta-cells to produce insulin. In some examples, the anti-CD3 antibody is suitable for administration to a human, e.g., is the subject of a clinical trial or has already been approved by a regulatory agency. In some examples, the anti-CD3 antibody is otelixizumab or teplizumab.

Recent-Onset T1D

The inventors have discovered that subjects with certain minimal amounts of residual beta-cell function respond particularly well to the therapeutic methods described herein. Residual beta-cell function may be measured in accordance with art recognized methods and as described herein. However, sufficient residual beta-cell function is typically found in subjects who have not been exposed to harmful auto-immune functions targeting the subject's beta-cells for too long. Thus, in some embodiments, the mammalian subject in the above methods has recently been diagnosed with T1D. For example, such subject may be referred to as having "recent-onset T1D" or "new-onset T1D" (used interchangeably herein). In some examples according to these embodiments, the subject has been diagnosed with T1D within the previous 12 months, the previous 18 months, or the previous 24 months prior to administering a composition according to the present disclosure. In other examples, the subject has been treated with insulin for less than about 12 weeks, less than about 8 weeks, less than about 6 weeks, or less than about 4 weeks. In other examples, according to any of the above embodiments, the subject tested positive for at least one auto-antibody, e.g., tested positive for insulin autoantibody (IAA), islet-cell auto-antibodies, glutamic acid decarboxylase (e.g., GAD65) auto-antibodies, and/or ICA512 antibodies. In other examples, according to any of the above embodiments, the subject has a fasting plasma glucose level of greater than about 100 mg/dL, or greater than about 120 mg/dL, or greater than about 126 mg/dL. In other examples, according to any of the above embodiments, the subject has a fasting plasma glucose level of about 180 to about 250 mg per deciliter (mg/dL), or about 10 mmol/L to about 14 mmol/L. In other examples, according to any of the above embodiments, the subject has a plasma glucose level of about 100 to about 500 mg/dL, In other examples, according to any of the above embodiments, the subject had polyuria for less than about 8 months, less than about 6 months, or less than about 4 months.

In some examples, a human subject may be categorized as having early onset T1D when any one of the following is measured in the subject: (1) two consecutive fasting blood glucose tests are equal to or greater than 126 mg/dL; (2) when any random blood glucose measurement is greater than 200 mg/dL; (3) a hemoglobin A1c (HbA1c) test that is equal to or greater than 6.5 percent (HbA1c is a blood test that gives a three month average of blood sugars); or (4) a two-hour oral glucose tolerance test with any value over 200 mg/dL, or combinations thereof. Thus, normal glycemia may be characterized by any of the following: (1) two consecutive fasting blood glucose tests are below 126 mg/dL, below 120 mg/dL, or below 100 mg/dL; (2) when any random blood glucose measurement is below 200 mg/dL, below 180 mg/dL, below 160 mg/dL, or below 140 mg/dL; (3) a hemoglobin A1c (HbA1c) test that is less than 6.5 percent, or less than 6%; or (4) a two-hour oral glucose tolerance test with a value below 200 mg/dL, below 180 mg/dL, below 160 mg/dL, or below 140 mg/dL, or any combination thereof.

A subject that returns to normoglycemia (e.g. no glucosuria and blood glucose measurements >200 mg/dl) following treatment may be considered to be a "responder" to the treatment. Subject who do not return to substantial normoglycemia are "non-responders".

The concentrations of C-peptide in the blood or urine of a subject may be used to assess a subject's beta-cell function and the T1D disease stage, where higher concentrations of C-peptide indicate higher beta-cell function. In some examples, the subject (e.g., human patient) has recent-onset T1D, characterized by having a fasting blood C-peptide concentration of less than about 1 nmol/L, but at least about 0.2 nmol/L. In other embodiments, the recent-onset subject (e.g., human patient) has a stimulated blood C-peptide concentration, e.g., during a 4-hour mixed meal tolerance test (MMTT) of less than about 5 nmol/L, but at least about 0.2 nmol/L, or less than about 4 nmol/L, but at least about 0.5 nmol/L. Other suitable C-peptide ranges are described herein. Stimulated C-peptide may thus be measured using MMTT area under the curve C-peptide (AUC CP), or may alternatively be measured using a 90 minute MMTT stimulated CP (90CP post MMTT or 90CP).

Promoter

By "promoter" is meant generally a region on a nucleic acid molecule, for example DNA molecule, to which an RNA polymerase binds and initiates transcription. A promoter is for example, positioned upstream, i.e., 5', of the sequence the transcription of which it controls. The skilled person will appreciate that the promoter may be associated with additional native regulatory sequences or regions, e.g. operators. The precise nature of the regulatory regions needed for expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the Pribnow-box (cf. TATA-box), Shine-Dalgarno sequence, and the like.

Expression Cassette

The term "expression cassette" or "expression unit" is used in accordance with its generally accepted meaning in the art, and refers to a nucleic acid containing one or more genes and sequences controlling the expression of the one or more genes. Exemplary expression cassettes contain at least one promoter sequence and at least one open reading frame.

Polycistronic Expression Cassette

The terms "polycistronic expression cassette" "polycistronic expression unit" or "polycistronic expression system" are used herein interchangeably and in accordance with their generally accepted meaning in the art. They refer to a nucleic acid sequence wherein the expression of two or more genes is regulated by common regulatory mechanisms, such as promoters, operators, and the like. The term polycistronic expression unit as used herein is synonymous with multicistronic expression unit. Examples of polycistronic expression units are without limitation bicistronic, tricistronic, tetracistronic expression units. Any mRNA comprising two or more, such as 3, 4, 5, 6, 7, 8, 9, 10, or more, open reading frames or coding regions encoding individual expression products such as proteins, polypeptides and/or peptides is encompassed within the term polycistronic. A polycistronic expression cassette includes at least one promoter, and at least two open reading frames controlled by the promoter, wherein an intergenic region is optionally placed between the two open reading frames.

In some example, the "polycistronic expression cassette" includes one or more endogenous genes and one or more exogenous genes that are transcriptionally controlled by a promoter which is endogenous to the microorganism (e.g., LAB). The polycistronic expression unit or system as described herein can be transcriptionally controlled by a promoter that is exogenous to the microorganism (e.g., LAB). In a further embodiment, the translationally or transcriptionally coupled one or more endogenous genes and one or more exogenous genes as described herein are transcriptionally controlled by the native promoter of (one of) said one or more endogenous genes. In another embodiment, the polycistronic expression unit is transcriptionally controlled by the native promoter of (one of) said one or more endogenous genes comprised in said polycistronic expression unit. In another embodiment, the polycistronic expression unit is operably linked to a gram-positive endogenous promoter. In an exemplary embodiment, the promoter may be positioned upstream of, i.e., 5' of the open reading frame(s) to which it is operably linked. In a further embodiment, the promoter is the native promoter of the 5' most, i.e., most upstream, endogenous gene in the polycistronic expression unit. Accordingly, in some examples, the polycistronic expression unit contains an endogenous gene and one or more exogenous genes transcriptionally coupled to the 3' end of said one or more endogenous gene, for example wherein said one or more exogenous gene(s) is (are) the most 3' gene(s) of the polycistronic expression unit.

As used herein, the term "translationally coupled" is synonymous with "translationally linked" or "translationally connected". These terms in essence relate to polycistronic expression cassettes or units. Two or more genes, open reading frames or coding sequences are said to be translationally coupled when common regulatory element(s) such as in particular a common promoter effects the transcription of said two or more genes as one mRNA encoding said two or more genes, open reading frames or coding sequences, which can be subsequently translated into two or more individual polypeptide sequences. The skilled person will appreciate that bacterial operons are naturally occurring polycistronic expression systems or units in which two or more genes are translationally or transcriptionally coupled.

Intergenic Region

As used herein, the term "intergenic region" is synonymous with "intergenic linker" or "intergenic spacer". An intergenic region is defined as a polynucleic acid sequence between adjacent (i.e., located on the same polynucleic acid sequence) genes, open reading frames, cistrons or coding sequences. By extension, the intergenic region can include the stop codon of the 5' gene and/or the start codon of the 3' gene which are linked by said intergenic region. As defined herein, the term intergenic region specifically relates to intergenic regions between adjacent genes in a polycistronic expression unit. For example, an intergenic region as defined herein can be found between adjacent genes in an operon. Accordingly, in an embodiment, the intergenic region as defined herein is an operon intergenic region.

In some examples, the intergenic region, linker or spacer is selected from intergenic regions preceding, i.e., 5' to, more particularly immediately 5' to, rp/W, rpf P, rpmD, rp/8, rpsG, rpsE or rp/N of a gram-positive bacterium. In an embodiment, said gram positive bacterium is a lactic acid bacterium, for example a *Lactococcus* species, e.g., *Lactococcus lactis*, and any subspecies or strain thereof. In an embodiment, said intergenic region encompasses the start codon of rp/W, rp/P, rpmD, rp/8, rpsG, rpsE or rp/N and/or the stop codon of the preceding, i.e. 5', gene. In a preferred embodiment, the invention relates to a gram-positive bacterium or a recombinant nucleic acid as described herein, wherein the endogenous gene and the one or more exogenous genes are transcriptionally coupled by intergenic region or regions active in the gram-positive bacterium, for example wherein the intergenic region or regions is endogenous to said gram-positive bacterium, for example, wherein the endogenous intergenic region is selected from intergenic regions preceding rp/W, rpf P, rpmD, rp/8, rpsG, rpsE, rp/N, rplM, rplE, and rplF.

The skilled person will appreciate that if the intergenic region encompasses a 5' stop codon and/or a 3' start codon, these respective codons in some cases are not present in the genes which are linked by said intergenic regions, in order to avoid double start and/or stop codons, which may affect correct translation initiation and/or termination. Methods for identifying intergenic regions are known in the art. By means of further guidance, intergenic regions can for instance be identified based on prediction of operons, and associated promoters and open reading frames, for which software is known and available in the art. Exemplary intergenic regions are described in international patent application publication WO2012/164083, the disclosure of which is incorporated herein by reference in its entirety.

Subject

A "subject" is an organism, which may benefit from being administered a composition of the present disclosure, e.g., according to methods of the present disclosure. The subject may be a mammal ("mammalian subject"). Exemplary mammalian subjects include humans, farm animals (such as cows, pigs, horses, sheep, goats), pets or domesticated animals (such as a dogs, cats, and rabbits), and other animals, such as mice, rats, and primates. In some examples, the mammalian subject is a human patient.

The term "international unit" (IU) is used herein in accordance with its art-recognized meaning and represents an amount of a substance (e.g., polypeptide). The mass or volume that constitutes one international unit varies based on which substance is being measured. The World Health Organization (WHO) provides unit characterizations for bioactive polypeptides.

TID Specific Antigen

The at least one microorganism of the present disclosure contains an exogenous nucleic acid encoding at least one disease-specific (i.e., T1D-specific) self-antigen gene, and can express such gene under conditions sufficient for expression. Exemplary T1D-specific self-antigens include islet antigens associated with the beta-cell destruction process. In some embodiments, in any of the above compositions and methods, the T1D-specific antigen is selected from known auto-antigens associated with T1D, and include proinsulin (PINS); insulin (INS); glutamic acid decarboxylase (GAD) (e.g., GAD65, GAD67, or GAD2); insulinoma-associated protein 2 (islet antigen-2; IA-2) (also referred to as protein tyrosine phosphatase, receptor type, N (PTPRN), tyrosine phosphatase-like protein, or ICA512), (see, e.g., Long et al., *Diabetes* 2013, 62 (6), 2067-2071); islet-specific glucose-6-phosphatase catalytic subunit-related protein (IGRP), zinc transporter 8 (ZnT8). Other examples include molecules expressed by beta-cells, such as chromogranin A, (prepro) islet amyloid polypeptide (ppIAPP), peripherin, citrullinated glucose-regulated protein (e.g., GRP78); see, e.g., Rondas et al., *Diabetes* 2015; 64(2):573-586; and Ye et al., *Diabetes* 2010, 59(1):6-16), and combinations of two or more of these antigens. In other embodiments, in the above compositions and methods, the T1D-specific antigen is PINS, GAD65, or IA-2. In other embodiments, in the above compositions and methods, the T1D-specific antigen is PINS. In various embodiments, the T1D-specific antigen is encoded by a variant nucleic acid sequence shorter than a full length (e.g., wild-type) gene, as such "trimmed" versions are often more efficiently expressed and/or secreted by the microorganisms used (e.g., *Lactococcus lactis*). While secretion is more efficient, many "trimmed" versions retain all (or a substantial portion) of their biological activity, e.g., retain sufficient Treg stimulating and/or tolerance-inducing capacities.

Examples of PINS polypeptides include wild-type human PINS and polypeptides having at least about 60%, at least about 70%, at least about 80%, at least about 90%, at least about 95%, at least about 96%, at least about 97%, at least about 98%, or at least about 99% sequence identity with such wild-type human PINS. An exemplary amino acid sequence of wild-type human PINS is SEQ ID NO: 5, and an exemplary nucleic acid sequence is represented by SEQ ID NO: 6 (see CDS contained in accession number NM_000207.2). In some examples, the PINS polypeptide has an amino acid sequence of SEQ ID NO: 3, which is encoded by a nucleic acid sequence of SEQ ID NO: 4.

Additional exemplary PINS nucleotide sequences are represented by the coding sequences of NCBI accession numbers AY899304 (complete CDS, alternatively spliced; SEQ ID NO: 7); NM_000207 (transcript variant 1);

NM_001185097 (transcript variant 2); NM_001185098 (transcript variant 3); NM_001291897 (transcript variant 4), and partial sequences thereof. Exemplary PINS amino acid sequences include those encoded by any one of the above PINS nucleic acid sequences.

Any nucleotide sequence encoding the amino acid sequence of SEQ ID NO: 3, or any nucleotide sequence encoding at least about 20, at least about 30, at least about 40, at least about 50, at least about 60, at least about 70, or at least about 80 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity with SEQ ID NO: 3 may be used.

Additional PINS polypeptides are described, e.g., in UniProtKB-P01308 and links therein. In some examples, the PINS polypeptide is represented by amino acid residues 25-110 (numbering according to SEQ ID NO: 5).

Exemplary GAD (e.g., GAD65) polypeptides include wild-type human GAD65, and polypeptides having at least about 60%, at least about 70%, at least about 80%, at least about 90%, at least about 95%, at least about 96%, at least about 97%, at least about 98%, or at least about 99% sequence identity with such wild-type GAD65. See, e.g., CDS contained in accession number M81882.1.

Any nucleotide sequence encoding the above amino acid sequence, or any nucleotide sequence encoding at least about 100, at least about 200, at least about 300, at least about 400, or at least about 500 consecutive amino acids thereof, or any nucleotide sequence encoding a polypeptide having at least about 60%, at least about 70%, at least about 80%, at least about 90%, at least about 95%, at least about 96%, at least about 97%, at least about 98%, or at least about 99% sequence identity may be used.

Other exemplary glutamate decarboxylase (e.g., GAD65) sequences are described, e.g., in UniProtKB-Q05329 and links therein. In some example, the GAD polypeptide is a trimmed variant containing less than about 500, less than about 400, or less than about 300 of the wild-type amino acids. Exemplary polypeptide fragments (trimmed GAD65 variants) are described, e.g., in Robert et al., *Benef. Microbes* 2015, 6(4): 591-601, the disclosure of which is incorporated herein by reference in its entirety. In some examples, the trimmed GAD variants are efficiently expressed and secreted by a gram-positive bacterium (i.e., *Lactococcus lactis*). An exemplary trimmed GAD variant is GAD65$_{370-575}$ (amino acid numbering relative to NCBI accession number NP_000809.1).

Other exemplary GAD nucleotide sequences are represented by NCBI accession numbers M81882 (GAD65); M81883 (GAD67); NM_000818 (GAD2 variant 1); and NM_001134366 (GAD2 variant 2); and open reading frames (CDS) contained therein. Exemplary amino acid sequences include sequences encoded by the above nucleotide sequences of accession numbers M81882, M81883, NM_001134366, and NM_000818.

A person of ordinary skill in the art will appreciate that the optimal amount of self-antigen to be delivered to the subject using the methods of the present disclosure varies, e.g., with the type of antigen, the microorganism expressing the antigen, and the genetic construct, e.g., the strength of the promoter used in the genetic construct. Typically, the microorganism will be administered in an amount equivalent to a particular amount of expressed antigen, or in an amount, which generates a desired PK profile for the respective antigen polypeptide in the respective subject. Exemplary daily antigen doses are from about 10 fg to about 100 µg of active polypeptide per day. Other exemplary dose ranges are from about 1 pg to about 100 µg per day; or from about 1 ng to about 100 µg per day.

The above antigen doses may be realized by administering to the subject effective amounts of the microorganism per day, wherein the microorganism is adapted to express a sufficient amount of bioactive polypeptide to realize the desired dose, such as those above. The microorganism secreting the antigen polypeptide may be delivered in a dose of from about $10^4$ colony forming units (cfu) to about $10^{12}$ cfu per day, e.g., from about $10^6$ cfu to about $10^{12}$ cfu per day, or from about $10^9$ cfu to about $10^{12}$ cfu per day.

The amount of secreted antigen polypeptide can be determined based on cfu, for example in accordance with the methods described in Steidler et al., *Science* 2000; 289 (5483):1352-1355, or by using ELISA. For example, a particular microorganism may secrete at least about 1 ng to about 1 µg of active polypeptide per $10^9$ cfu. Based thereon, the skilled person can calculate the range of antigen polypeptide secreted at other cfu doses.

Each of the above doses/dose ranges may be administered in connection with any dosing regimen as described herein. The daily dose of active polypeptide may be administered in 1, 2, 3, 4, 5, or 6 portions throughout the day. Further the daily doses may be administered for any number of days, with any number of rest periods between administration periods. For example, a dose of from about 0.01 to about 3.0 M IU of IL-10/day/subject may be administered every other day for a total of 6 weeks.

Treating

The terms "treatment", "treating", and the like, as used herein means ameliorating or alleviating characteristic symptoms or manifestations of a disease or condition, e.g., T1D. For example, treatment of T1D can result in the restoration or induction of antigen-specific immune tolerance in the subject. In other examples, treatment means arresting auto-immune diabetes, or reversing autoimmune diabetes. As used herein these terms also encompass, preventing or delaying the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. Treatment of a subject "in need thereof" conveys that the subject has a diseases or condition, and the therapeutic method of the invention is performed with the intentional purpose of treating the specific disease or condition.

Patient Sub-Populations

In some embodiments, the subject being treated using the methods of the present disclosure, has significant (e.g., measurable) residual beta-cell function. Under such circumstances, the subject may maintain disease remission, even after treatment is interrupted or stopped altogether. Newly diagnosed patients often have a certain minimal number of pancreatic islet beta-cells (beta-cells) remaining at the time of diagnosis, so that such patients are able to produce a certain minimal amount of endogenous insulin. Such patient population can benefit particularly well when treated with the compositions and methods of the current disclosure (e.g., IL-10 and PINS therapy). The treatments described herein can prevent further destruction of beta-cells and may thus induce disease remission. Unexpectedly, the inventors have found that initial beta-cell mass can be important for the efficacy of treatment. However, once a subject's beta-cells are destroyed, such subject may no longer benefit from the described treatment in the same manner.

Untreated T1D develops over time and becomes progressively worse as beta cells in the pancreas are destroyed. Thus, as the present method can halt disease, it is advantageous to treat subjects as early as possible in the disease progression. Thus, in a related embodiment, the therapeutic method of the invention also includes measuring disease progression prior to therapy, and during therapy.

Therapeutically Effective Amount

As used herein, the term "therapeutically effective amount" refers to an amount of a non-pathogenic microorganism or a composition of the present disclosure that will elicit a desired therapeutic effect or response when administered according to the desired treatment regimen. In some cases, the compounds or compositions are provided in a unit dosage form, for example a tablet or capsule, which contains an amount of the active component equivalent with the therapeutically effective amount when administered once, or multiple times per day.

A person of ordinary skill in the art will appreciate that a therapeutically effective amount of a recombinant microorganism, which is required to achieve a desired therapeutic effect (e.g., for the effective treatment of T1D), will vary, e.g., depending on the nature of the IL-10 polypeptide expressed by the microorganism, the nature of the antigen polypeptide expressed by the microorganism, the route of administration, and the age, weight, and other characteristics of the recipient.

Mucosa

The term "mucosa" or "mucous membrane" is used herein in accordance with its art recognized meaning. The "mucosa" can be any mucosa found in the body, such as oral mucosa, rectal mucosa, gastric mucosa, intestinal mucosa, urethral mucosa, vaginal mucosa, ocular mucosa, buccal mucosa, bronchial or pulmonary mucosa, and nasal or olfactory mucosa.

The term "mucosal delivery" as used herein is used in accordance with its art recognized meaning, i.e., delivery to the mucosa, e.g., via contacting a composition of the present disclosure with a mucosa. Oral mucosal delivery includes buccal, sublingual and gingival routes of delivery. Accordingly, in some embodiments, "mucosal delivery" includes gastric delivery, intestinal delivery, rectal delivery, buccal delivery, pulmonary delivery, ocular delivery, nasal delivery, vaginal delivery and oral delivery.

The term "mucosal tolerance" refers to the inhibition of specific immune responsiveness to an antigen in a mammalian subject (e.g., a human patient), after the subject has been exposed to the antigen via the mucosal route. In some cases the mucosal tolerance is systemic tolerance. Low dose oral tolerance is oral tolerance induced by low doses of antigens, and is characterized by active immune suppression, mediated by cyclophosphamide sensitive regulatory T-cells that can transfer tolerance to naive hosts. High dose oral tolerance is oral tolerance induced by high doses of antigens, is insensitive to cyclophosphamide treatment, and proceeds to induction of T cell hyporesponsiveness via anergy and/or deletion of antigen specific T-cells. The difference in sensitivity to cyclophosphamide can be used to make a distinction between low dose and high dose tolerance (Strobel et al., 1983). In some cases, the oral tolerance is low dose oral tolerance as described by Mayer and Shao (2004).

Immuno-Modulating Compound

The terms "immuno-modulating compound" or immunomodulator" are used herein in accordance with their art-recognized meaning. The immuno-modulating compound can be any immuno-modulating compound known to a person skilled in the art.

In some embodiments, the immuno-modulating compound is a tolerance inducing compound. Tolerance induction can be obtained, e.g., by inducing regulatory T-cells, or in an indirect way, e.g., by activation of immature dendritic cells to tolerizing dendritic cells and/or inhibiting Th2 immune response inducing expression of "co-stimulation" factors on mature dendritic cells Immuno-modulating and immuno-suppressing compounds are known to the person skilled in the art and include, but are not limited to, bacterial metabolites such as spergualin, fungal and streptomycal metabolites such as tacrolimus or ciclosporin, immuno-suppressing cytokines such as IL-4, IL-10, IFN$\alpha$, TGF$\beta$ (as selective adjuvant for regulatory T-cells) Flt3L, TSLP and Rank-L (as selective tolerogenic DC inducers), antibodies and/or antagonist such as anti-CD40L, anti-CD25, anti-CD20, anti-IgE, anti-CD3, and proteins, peptides or fusion proteins such as the CTL-41 g or CTLA-4 agonist fusion protein. In some embodiments, the immuno-modulating compound is an immuno-suppressing compound. In other embodiments, the immuno-suppressing compound is an immuno-suppressing cytokine or antibody. In other embodiments, the immuno-suppressing cytokine is a tolerance-enhancing cytokine or antibody. It will be appreciated by the person skilled in the art that the term "immuno-modulating compound" also includes functional homologues thereof. A functional homologue is a molecule having essentially the same or similar function for the intended purposes, but can differ structurally. In some examples, the immuno-modulating compound is anti-CD3, or a functional homologue thereof.

Microorganisms

The invention relates to the use of at least one microorganism. In some embodiments, the microorganism is a non-pathogenic and non-invasive bacterium. In other embodiments, the microorganism is a non-pathogenic and non-invasive yeast.

In some embodiments, the microorganism is a yeast strain selected from the group consisting of *Saccharomyces* sp., *Hansenula* sp., *Kluyveromyces* sp. *Schizzosaccharomyces* sp. *Zygosaccharomyces* sp., *Pichia* sp., *Monascus* sp., *Geothchum* sp and *Yarrowia* sp. In some embodiments, the yeast is *Saccharomyces cerevisiae*. In other embodiments, the *S. cerevisiae* is of the subspecies *boulardii*. In one embodiment of the present invention, the recombinant yeast host-vector system is a biologically contained system. Biological containment is known to the person skilled in the art and can be realized by the introduction of an auxotrophic mutation, for example a suicidal auxotrophic mutation such as the ThyA mutation, or its equivalents.

In other embodiments of the present invention, the microorganism is a bacterium, such as a non-pathogenic bacterium, e.g., a food grade bacterial strain. In some examples, the non-pathogenic bacterium is a gram-positive bacterium, e.g., a gram-positive food-grade bacterial strain. In some embodiments, the gram-positive food grade bacterial strain is a lactic acid fermenting bacterial strain (i.e., a lactic acid bacterium (LAB) or a *Bifidobacterium*).

In some embodiments, the lactic acid fermenting bacterial strain is a *Lactococcus, Lactobacillus* or *Bifidobacterium* species. As used herein, *Lactococcus* or *Lactobacillus* is not limited to a particular species or subspecies, but meant to include any of the *Lactococcus* or *Lactobacillus* species or subspecies. Exemplary *Lactococcus* species include *Lactococcus garvieae, Lactococcus lactis, Lactococcus piscium, Lactococcus plantarum,* and *Lactococcus raffinolactis.* In some examples, the *Lactococcus lactis* is *Lactococcus lactis* subsp. *cremoris, Lactococcus lactis* subsp. hordniae, or *Lactococcus lactis* subsp. *Lactis.*

Exemplary *Lactobacillus* species include *Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus camis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus fornicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefiranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rimae, Lactobacillus rogosae, Lactobacillus ruminis, Lactobacillus sakei, Lactobacillus sakei* subsp. *camo sus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp. *mali, Lactobacillus yamanashiensis* subsp. *Yamanashiensis, Lactobacillus zeae, Bifidobacterium adolescentis, Bifidobacterium angulatum, Bifidobacterium bifidum, Bifidobacterium breve, Bifidobacterium catenulatum, Bifidobacterium longum,* and *Bifidobacterium infantis.* In some examples, the LAB is *Lactococcus lactis* (LL).

In further examples, the bacterium is selected from the group consisting of *Enterococcus alcedinis, Enterococcus aquimarinus, Enterococcus asini, Enterococcus avium, Enterococcus caccae, Enterococcus camelliae, Enterococcus canintestini, Enterococcus canis, Enterococcus casseliflavus, Enterococcus cecorum, Enterococcus columbae, Enterococcus devriesei, Enterococcus diestrammenae, Enterococcus dispar, Enterococcus durans, Enterococcus eurekensis, Enterococcus faecalis, Enterococcus faecium, Enterococcus gallinarum, Enterococcus gilvus, Enterococcus haemoperoxidus, Enterococcus hermanniensis, Enterococcus hirae, Enterococcus italicus, Enterococcus lactis, Enterococcus lemanii, Enterococcus malodoratus, Enterococcus moraviensis, Enterococcus mundtii, Enterococcus olivae, Enterococcus pallens, Enterococcus phoeniculicola, Enterococcus plantarum, Enterococcus pseudoavium, Enterococcus quebecensis, Enterococcus raffinosus, Enterococcus ratti, Enterococcus rivorum, Enterococcus rotai, Enterococcus saccharolyticus, Enterococcus silesiacus, Enterococcus solitarius, Enterococcus sulfureus, Enterococcus termitis, Enterococcus thailandicus, Enterococcus ureasiticus, Enterococcus ureilyticus, Enterococcus viikkiensis, Enterococcus villorum,* and *Enterococcus xiangfangensis,*

In further examples, the bacterium is selected from the group consisting of *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus milleri, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans,* and *Streptococcus zooepidemicus.*

In a particular aspect of the present invention, the gram-positive food grade bacterial strain is *Lactococcus lactis* or any of its subspecies, including *Lactococcus lactis* subsp. *Cremoris, Lactococcus lactis* subsp. Hordniae, and *Lactococcus lactis* subsp. *Lactis.* In another aspect of the present invention, the recombinant gram-positive bacterial strains is a biologically contained system, such as the plasmid free *Lactococcus lactis* strain MG1363, that lost the ability of normal growth and acid production in milk (Gasson, M. J. (1983) *J. Bacteriol.* 154:1-9); or the threonine- and pyrimidine-auxotroph derivative *L. lactis* strains (Sorensen et al. (2000) *Appl. Environ. Microbiol.* 66:1253-1258; Glenting et al. (2002) 68:5051-5056).

In one embodiment of the present invention, the recombinant bacterial host-vector system is a biologically contained system. Biological containment is known to the person skilled in the art and can be realized by the introduction of an auxotrophic mutation, for example a suicidal auxotrophic mutation such as the ThyA mutation, or its equivalents, debilitating DNA synthesis. Other examples of auxotrophic mutations can debilitate RNA, cell wall or protein synthesis. Alternatively, the biological containment can be realized at the level of the plasmid carrying the gene encoding the IL-10 polypeptide or IL-10 variant, such as, for example, by using an unstable episomal construct, which is lost after a few generations. Several levels of containment, such as plasmid instability and auxotrophy, can be combined to ensure a high level of containment, if desired.

Constructs

In the present invention, the microorganism (e.g., the non-pathogenic gram-positive bacterium) delivers the IL-10 polypeptide and the T1D-specific antigen (e.g., PINS) at the intended site, i.e., the mucosa. For example, the microorganism (e.g., LAB) expresses the IL-10 polypeptide, after which the IL-10 polypeptide is secreted (if a secreted form of IL-10 is used). Hence, in a particular embodiment the microorganism (e.g., LAB), such as L. lactis, expresses IL-10 and PINS at the site of an intended mucosa, e.g., in the gastrointestinal tract.

Use of an operon enables expression of the IL-10 polypeptide and T1D-specific antigen polypeptide (e.g., PINS) to be coordinated. Polycistronic expression systems in bacterial host cells are described, e.g., in U.S. Patent Application No. 2014/0105863 to Vanden-Broucke et al., which is incorporated herein by reference in its entirety.

In an embodiment the present invention relates to stably transfected microorganisms, i.e., microorganisms in which the gene coding for the IL-10 polypeptide and the T1D-specific antigen (e.g., PINS) gene has been integrated into the host cell's genome. Techniques for establishing stably transfected microorganisms are known in the art. For instance, the IL-10 polypeptide and the T1D-specific antigen (e.g., PINS) gene may be cloned into the host's genome, e.g. in the chromosome, via homologous recombination. In some embodiments, an essential gene of the host is disrupted by the homologous recombination event, such as deletion of the gene, one or more amino acid substitutions leading to an inactive form of the protein encoded by the essential gene, or to a frameshift mutation resulting in a truncated form of the protein encoded by the essential gene. In an embodiment, the essential gene is the thyA gene. A preferred technique is described, e.g., in WO 02/090551, which is incorporated herein by reference in its entirety. The plasmid may be a self-replicating, for example carrying one or more genes of interest and one or more resistance markers. Then, the transforming plasmid can be any plasmid, as long as it cannot complement the disrupted essential gene, e.g., thyA gene. Alternatively, the plasmid is an integrative plasmid. In the latter case, the integrative plasmid itself may be used to disrupt the essential gene, by causing integration at the locus of the essential gene, e.g., thyA site, because of which the function of the essential gene, e.g., the thyA gene, is disrupted. In some cases, the essential gene, such as the thyA gene, is replaced by double homologous recombination by a cassette comprising the gene or genes of interest, flanked by targeting sequences that target the insertion to the essential gene, such as the thyA target site. It will be appreciated that that these targeting sequences are sufficiently long and sufficiently homologous to enable integration of the gene of interest into the target site. In some examples, an IL-10 expression cassette of the present disclosure is integrated at the thyA locus.

The genetic construct encoding the IL-10 polypeptide and the T1D-specific antigen (e.g., PINS) may be integrated into the microbial genomic DNA, e.g., bacterial or yeast chromosome, e.g., Lactococcus chromosome. In the latter case, a single or multiple copies of the nucleic acid may be integrated; the integration may occur at a random site of the chromosome or, as described above, at a predetermined site thereof, for example at a predetermined site, such as, in a non-limiting example, in the thyA locus of Lactococcus, e.g., Lactococcus lactis.

Hence, in an embodiment, the genetic construct encoding the IL-10 polypeptide and the T1D-specific antigen (e.g., PINS) may further comprise sequences configured to effect insertion of the genetic construct into the genome, e.g., a chromosome, of a host cell.

In some examples, insertion of the genetic construct into particular sites within a genome, e.g., chromosome, of a host cell may be facilitated by homologous recombination. For instance, the genetic construct the invention may comprise one or more regions of homology to the said site of integration within the genome e.g., a chromosome, of the host cell. The sequence at the said genome, e.g., chromosome, site may be natural, i.e., as occurring in nature, or may be an exogenous sequence introduced by previous genetic engineering. For instance, the region(s) of homology may be at least 50 bp, 100 bp, 200 bp, 300 bp, 400 bp, 500 bp, 600 bp 700 bp, 800 bp, 900 bp, 1000 bp, or more.

In one example, two regions of homology may be included, one flanking each side of the relevant expression units present in the genetic construct of the invention. Such configuration may advantageously insert the relevant sequences, i.e., at least the ones encoding and effecting the expression of the antigen of interest, in host cells. Ways of performing homologous recombination, especially in bacterial hosts, and selecting for recombinants, are generally known in the art.

Transformation methods of microorganisms are known to the person skilled in the art, such as for instance protoplast transformation and electroporation.

A high degree of expression can be achieved by using homologous expression and/or secretion signals on the expression vectors present in the microorganism, e.g., L. lactis. Expression signals will be apparent to the person skilled in the art. The expression vector can be optimized for expression depending on the microorganism, e.g., L. lactis, it is incorporated in. For instance, specific expression vectors that gave sufficient levels of expression in Lactococcus, Lactobacillus lactis, casei and plantarum are known. Moreover, systems are known which have been developed for the expression of heterologous antigens in the non-pathogenic, non-colonizing, non-invasive food-grade bacterium Lactococcus lactis (see UK patent GB2278358B, which is incorporated herein by reference). A particularly preferred construct according to the invention comprises the multi-copy expression vector described in PCT/NL95/00135 (WO-A-96/32487), in which the nucleotide sequence encoding the IL-10 polypeptide and/or the T1D-specific antigen (e.g., PINS) has been incorporated. Such a construct is particularly suitable for expression of a desired antigen in a lactic acid bacterium, in particular in a Lactobacillus, at a high level of expression, and also can be used advantageously to direct the expressed product to the surface of the bacterial cell. The constructs (e.g., of PCT/NL95/00135) may be characterized in that the nucleic acid sequence encoding the IL-10 polypeptide and/or T1D-specific antigen (e.g., PINS) is preceded by a 5' non-translated nucleic acid sequence comprising at least the minimal sequence required for ribosome recognition and RNA stabilization. This can be followed by a translation initiation codon which may be (immediately) followed by a fragment of at least 5 codons of the 5' terminal part of the translated nucleic acid sequence of a gene of a lactic acid bacterium or a structural or functional equivalent of the fragment. The fragment may also be controlled by the promoter. The contents of PCT/NL95/00135, including the differing embodiments disclosed therein, and all other documents mentioned in this specification, are incorporated herein by reference. One aspect of the present invention provides a method which permits the high level regulated expression of heterologous genes in the host and the coupling of expression to secretion. In another embodiment, the T7 bacteriophage RNA polymerase and its cognate promoter are used to develop a powerful expression system according to WO 93/17117, which is incorporated herein by reference. In one embodiment, the expression plasmid is derived from pT1 NX (GenBank: HM585371.1).

A promoter employed in accordance with the present invention is in some cases expressed constitutively in the bacterium. The use of a constitutive promoter avoids the need to supply an inducer or other regulatory signal for expression to take place. In some cases, the promoter directs expression at a level at which the bacterial host cell remains viable, i.e., retains some metabolic activity, even if growth is not maintained. Advantageously then, such expression may be at a low level. For example, where the expression product accumulates intracellularly, the level of expression may lead to accumulation of the expression product at less than about 10% of cellular protein, about or less than about 5%, for example about 1-3%. The promoter may be homologous to the bacterium employed, i.e., one found in that bacterium in nature. For example, a Lactococcal promoter may be used in a *Lactococcus*. A preferred promoter for use in *Lactococcus lactis* (or other Lactococci) is "P1" derived from the chromosome of *Lactococcus lactis* (Waterfield, N R, Lepage, R W F, Wilson, P W, et al. (1995). "The isolation of lactococcal promoters and their use in investigating bacterial luciferase synthesis in *Lactococcus lactis*" Gene 165(1):9-15). Other examples of a promoter include, the usp45 promoter, the gapB promoter, and the hllA promoter. Other useful promoters are described in U.S. Pat. No. 8,759,088 to Steidler et al., and in U.S. Patent Application No. 2014/0105863 to Vanden-Broucke et al., the disclosures of which are incorporated herein by reference in their entirety. In some examples, a nucleic acid encoding an IL-10 polypeptide is placed under an hllA promoter.

The nucleic acid construct or constructs may comprise a nucleic acid encoding a secretory signal sequence. Thus, in some embodiments the nucleic acid encoding IL-10 and/or the T1D-specific antigen (e.g., PINS) may provide for secretion of the polypeptides, e.g., by appropriately coupling a nucleic acid sequence encoding a signal sequence to the nucleic acid sequence encoding the polypeptide). Ability of a bacterium harboring the nucleic acid to secrete the antigen may be tested in vitro in culture conditions which maintain viability of the organism. Preferred secretory signal sequences include any of those with activity in Gram positive organisms such as *Bacillus, Clostridium* and *Lactobacillus*. Such sequences may include the α-amylase secretion leader of *Bacillus* amyloliquetaciens or the secretion leader of the Staphylokinase enzyme secreted by some strains of *Staphylococcus*, which is known to function in both Gram-positive and Gram-negative hosts (see "Gene Expression Using *Bacillus*," Rapoport (1990) *Current Opinion in Biotechnology* 1:21-27), or leader sequences from numerous other *Bacillus* enzymes or S-layer proteins (see pp 341-344 of Harwood and Cutting, "Molecular Biological Methods for *Bacillus*," John Wiley & Co. 1990). In one embodiment, said secretion signal is derived from usp45 (Van Asseldonk et al. (1993) *Mol. Gen. Genet.* 240:428-434). Such secretion leader is referred to herein, e.g., as SSusp45. In some embodiments, the IL-10 polypeptide is constitutively secreted using SSusp45. In other examples, the PINS polypeptide is secreted using SSusp45. In yet other examples, both the IL-10 polypeptide and the PINS polypeptide are secreted using SSusp45.

A person of ordinary skill in the art will appreciate that the optimal amount of IL-10 and PINS to be delivered to the subject using the methods of the present disclosure varies, e.g., with the microorganism expressing the IL-10 polypeptide and the PINS polypeptide, and the genetic constructs, e.g., the strength of the promoter used in the genetic constructs. Typically, the microorganism will be administered in an amount equivalent to a particular amount of expressed IL-10 polypeptide and PINS polypeptide, or in an amount which generates a desired PK profile for the respective IL-10 polypeptide or PINS polypeptide in the respective subject. Exemplary daily IL-10 polypeptide or PINS polypeptide doses are from about 10 fg to about 100 µg of active polypeptide per day. Other exemplary dose ranges are from about 1 pg to about 100 µg per day; or from about 1 ng to about 100 µg per day.

The above doses may be realized by administering to the subject effective amounts of the microorganism per day, wherein the microorganism is adapted to express a sufficient amount of IL-10 and a T1D-specific antigen (e.g., PINS) to realize the desired dose, such as those above. The microorganism secreting the IL-10 polypeptide and the T1D-specific antigen (e.g., PINS polypeptide) may be delivered in a dose of from about $10^4$ colony forming units (cfu) to about $10^{12}$ cfu per day, in particular from about $10^6$ cfu to about $10^{12}$ cfu per day, more in particular from about $10^9$ cfu to about $10^{12}$ cfu per day. The amount of secreted IL-10 and T1D-specific antigen (e.g., PINS polypeptide) can be determined based on cfu, for example in accordance with the methods described in Steidler et al., *Science* 2000; 289(5483):1352-1355, or by using ELISA. For example, a particular microorganism may secrete at least about 1 ng to about 1 µg IL-10 per $10^9$ cfu. Based thereon, the skilled person can calculate the range of IL-10 polypeptide secreted at other cfu doses.

Each of the above doses/dose ranges may be administered in connection with any dosing regimen as described herein. The daily dose may be administered in 1, 2, 3, 4, 5, or 6 portions throughout the day. Further the daily doses may be administered for any number of days, with any number of rest periods between administration periods. For example, the subject may be administered the microorganism at a dose equivalent to about 0.01 to about 3 M IU of IL-10/day or every other day, for a period of at least about 1 week, at least about 2 weeks, at least about 3 weeks, at least about 4 weeks, at least about 5 weeks, or at least about 6 weeks. In some examples, the subject is administered the microorganism at a dose equivalent to about 0.1 to about 5 MIU/day, or about 0.3 to about 3 MIU, e.g., for about 5 days, about 7 days, or about 14 days. Exemplary doses are described, e.g., in Hartemann et al., *Lancet Diabetes Endocrinol.* 2013, 1(4): 295-305, the disclosure of which is incorporated herein by reference in its entirety.

Formulations and Regimens

In some methods of the present disclosure, the IL-10 polypeptide and the T1D-specific antigen (e.g., PINS) are administered (delivered) to a subject (e.g., a human T1D-patient) using a microorganism (e.g., LAB) producing both the IL-10 polypeptide and the T1D-specific antigen (e.g., PINS) polypeptide.

In some embodiments, the microorganism (e.g., LAB), optionally contained in a composition (e.g., a pharmaceutical composition) of the present disclosure or a unit dosage form of the present disclosure, will be administered, once, twice, three, four, five, or six times daily, e.g., using an oral formulation. In some embodiments, the microorganism is administered every day, every other day, once per week, twice per week, three times per week, or four times per week. In other embodiments, treatment occurs once every two weeks. In other embodiments, treatment occurs once every three weeks. In other embodiments, treatment occurs once per month.

The duration of a treatment cycle is, for example, 7 days to the subject's lifetime, as needed to treat or reverse T1D, or prevent relapse. In some embodiments, a treatment cycle lasts for about 30 days to about 2 years. In other embodiments, the subject will have a treatment cycle that lasts from 30 days to 1.5 years. In other embodiments, the subject will have a treatment cycle that lasts from 30 days to 1 year. In other embodiments, the subject will have a treatment cycle that lasts from 30 days to 11 months. In other embodiments, the subject will have a treatment cycle that lasts from 30 days to 10 months. In other embodiments, the subject will have a treatment cycle that lasts from 30 days to 9 months. In other embodiments, the subject will have a treatment cycle that lasts from 30 days to 8 months. In other embodiments, the subject will have a treatment cycle that lasts from 30 days to 7 months. In other embodiments, the subject will have a treatment cycle that lasts from 30 days to 6 months. In other embodiments, the subject will have a treatment cycle that lasts from 30 days to 5 months. In other embodiments, the subject will have a treatment cycle that lasts from 30 days to 4 months. In other embodiments, the subject will have a treatment cycle that lasts from 30 days to 3 months. In other embodiments, the subject will have a treatment cycle that lasts from 30 days to 2 months.

In further embodiments, the treatment cycle will be based on the level of markers that track the progress of disease, including glycemic index, insulin autoantibody (IAA) levels, fragment C levels, and insulitis. Preferably, the subject is at early onset diabetes. A subject may also be assessed for the level of Treg cells that suppress the immune response to beta cells. In an exemplary embodiment, the subject is treated at least until there is no further disease progression, preferably until there is a return of normoglycemia. The patient may be treated for an additional period to ensure a population of Treg cells that suppress and reverse disease. A subject may also be monitored and treated at the first appearance of any indicia of reemergent disease.

Daily maintenance doses can be given for a period clinically desirable in the subject, for example from 1 day up to several years (e.g. for the subject's entire remaining life); for example from about (2, 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Nevertheless, unit doses should for example be administered from twice daily to once every two weeks until a therapeutic effect is observed.

The microorganisms producing the IL-10 polypeptide and the T1D-specific antigen (e.g., PINS) polypeptide may be administered to the subject in mono- or combination therapy (e.g., using a co-therapeutic regimen) for the treatment of T1D. "The term "co-therapy," "co-therapeutic" or variation thereof refers to a treatment regimen, in which the subject is administered at least one additional therapeutically active agent, such as an additional immuno-modulating compound. Thus, in some embodiments, the compositions of the present disclosure include additional therapeutically active agents. In some embodiments, the compositions of the present disclosure contain at least one additional immuno-modulating substance, such as antibodies (e.g., anti-CD3 antibodies). In some examples, the methods of the present disclosure further include administering to the subject (e.g., a human patient) an additional immuno-modulating substance, such as antibodies (e.g., anti-CD3 antibodies).

Pharmaceutical Compositions and Carriers

The microorganism (e.g., bacteria, such as LAB described herein) may be administered in pure form, combined with other active ingredients, and/or combined with pharmaceutically acceptable (i.e., nontoxic) excipients or carriers. The term "pharmaceutically acceptable" is used herein in accordance with its art-recognized meaning and refers to carriers that are compatible with the other ingredients of a pharmaceutical composition, and are not deleterious to the recipient thereof.

The compositions of the present disclosure can be prepared in any known or otherwise effective dosage or product form suitable for delivery of the microorganism (e.g., bacteria) to the mucosa, which would include pharmaceutical compositions and dosage forms as well as nutritional product forms.

In some embodiments, the pharmaceutical composition (i.e., formulation) is an oral pharmaceutical composition. In some examples according to this embodiment, the formulation or pharmaceutical composition comprises the non-pathogenic microorganism in a dried form (e.g., dry-powder form; e.g., freeze-dried form) or in compacted form thereof, optionally in combination with other dry carriers. Oral formulations will generally include an inert diluent carrier or an edible carrier.

In some examples, the oral formulation comprises a coating or utilizes an encapsulation strategy, which facilitates the delivery of the formulation into the intestinal tract, and/or allows the microorganism be released and hydrated in the intestinal tract (e.g., the ileum, small intestine, or the colon). Once the microorganism is released from the formulation and sufficiently hydrated, it begins expressing the bioactive polypeptides, which are subsequently released into the surroundings, or expressed on the surface of the microorganism. Such coating and encapsulation strategies (i.e., delayed-release strategies) are known to those of skill in the art. See, e.g., U.S. Pat. No. 5,972,685; WO 2000/18377; and WO 2000/22909, the disclosures of which are incorporated herein by reference in their entirety.

In some embodiments, the disclosure provides a pharmaceutical composition comprising the microorganism (e.g., the non-pathogenic bacteria) in a lyophilized or freeze dried form, optionally in conjunction with other components, such as dextrans, sodium glutamate, and polyols. Exemplary freeze dried compositions are described, e.g., in U.S. Patent Application No. 2012/0039853 to Corveleyn et al., the disclosure of which is incorporated herein by reference in its entirety. Exemplary formulations comprise freeze-dried bacteria (e.g., a therapeutically effective amount of the bacteria) and a pharmaceutically acceptable carrier. Freeze-dried bacteria may be prepared in the form of capsules, tablets, granulates and powders, each of which may be administered orally. Alternatively, freeze-dried bacteria may be prepared as aqueous suspensions in suitable media, or lyophilized bacteria may be suspended in a suitable medium, such as a drink, just prior to use. Such composition may additionally contain a stabilizing agent useful to maintain a stable suspension, e.g., without precipitation, aggregation, or floating of the bacterial biomass.

For oral administration, the formulation may be a gastro-resistant oral dosage form. For example, the oral dosage form (e.g., capsules, tablets, pellets, micro-pellets, granulates, and the like) may be coated with a thin layer of excipient (usually polymers, cellulosic derivatives and/or lipophilic materials) that resists dissolution or disruption in the stomach, but not in the intestine, thereby allowing transit through the stomach in favor of disintegration, dissolution and absorption in the intestine (e.g., the small intestine, or the colon).

In some examples, oral formulations may include compounds providing controlled release, sustained release, or prolonged release of the microorganism, and thereby provide controlled release of the desired protein encoded therein. These dosage forms (e.g., tablets or capsules) typically contain conventional and well known excipients, such as lipophilic, polymeric, cellulosic, insoluble, and/or swellable excipients. Controlled release formulations may also be used for any other delivery sites including intestinal, colon, bioadhesion or sublingual delivery (i.e., dental mucosal delivery) and bronchial delivery. When the compositions of the invention are to be administered rectally or vaginally, pharmaceutical formulations may include suppositories and creams. In this instance, the host cells are suspended in a mixture of common excipients also including lipids. Each of the aforementioned formulations are well known in the art and are described, for example, in the following references: Hansel et al. (1990, Pharmaceutical dosage forms and drug delivery systems, 5th edition, William and Wilkins); Chien 1992, Novel drug delivery system, 2nd edition, M. Dekker); Prescott et al. (1989, Novel drug delivery, J. Wiley & Sons); Gazzaniga et al., (1994, Oral delayed release system for colonic specific delivery, *Int. J. Pharm.* 108:77-83).

In some embodiments, the oral formulation includes compounds that can enhance mucosal delivery and/or mucosal uptake of the bioactive polypeptides expressed by the microorganism. In other examples, the formulation includes compounds, which enhance the viability of the microorganism within the formulation, and/or once released.

The bacteria of the invention can be suspended in a pharmaceutical formulation for administration to the human or animal having the disease to be treated. Such pharmaceutical formulations include but are not limited to live gram-positive bacteria and a medium suitable for administration. The bacteria may be lyophilized in the presence of common excipients such as lactose, other sugars, alkaline and/or alkali earth stearate, carbonate and/or sulphate (e.g., magnesium stearate, sodium carbonate and sodium sulphate), kaolin, silica, flavorants and aromas. Bacteria so-lyophilized may be prepared in the form of capsules, tablets, granulates and powders (e.g., a mouth rinse powder), each of which may be administered by the oral route. Alternatively, some gram-positive bacteria may be prepared as aqueous suspensions in suitable media, or lyophilized bacteria may be suspended in a suitable medium just prior to use, such medium including the excipients referred to herein and other excipients such as glucose, glycine and sodium saccharinate.

In some examples, the microorganism is locally delivered to the gastrointestinal tract of the subject using any suitable method. For example, microsphere delivery systems could be employed to enhance delivery to the gut. Microsphere delivery systems include microparticles having a coating that provides localized release into the gastrointestinal tract of the subject (e.g., controlled release formulations such as enteric-coated formulations and colonic formulations).

For oral administration, gastroresistant oral dosage forms may be formulated, which dosage forms may also include compounds providing controlled release of the gram-positive bacteria and thereby provide controlled release of the desired protein encoded therein (e.g., IL-10). For example, the oral dosage form (including capsules, tablets, pellets, granulates, powders) may be coated with a thin layer of excipient (e.g., polymers, cellulosic derivatives and/or lipophilic materials) that resists dissolution or disruption in the stomach, but not in the intestine, thereby allowing transit through the stomach in favor of disintegration, dissolution and absorption in the intestine.

The oral dosage form may be designed to allow slow release of the gram-positive bacteria and of the produced exogenous proteins, for instance as controlled release, sustained release, prolonged release, sustained action tablets or capsules. These dosage forms usually contain conventional and well-known excipients, such as lipophilic, polymeric, cellulosic, insoluble, and/or swellable excipients. Such formulations are well-known in the art and are described, for example, in the following references: Hansel et al., Pharmaceutical dosage forms and drug delivery systems, 5th edition, William and Wilkins, 1990; Chien 1992, Novel drug delivery system, 2nd edition, M. Dekker; Prescott et al., Novel drug delivery, J. Wiley & Sons, 1989; and Gazzaniga et al., *Int. J. Pharm.* 108: 77-83 (1994).

The pharmaceutical dosage form (e.g. capsule) may be coated with pH-dependent Eudragit polymers to obtain gastric juice resistance and for the intended delivery at the terminal ileum and colon, where the polymers dissolve at pH 6.5. By using other Eudragit polymers or a different ratio between the polymers, the delayed release profile could be adjusted, to release the bacteria for example in the duodenum or jejenum.

Pharmaceutical compositions contain at least one pharmaceutically acceptable carrier. Non-limiting examples of suitable excipients, diluents, and carriers include preservatives, inorganic salts, acids, bases, buffers, nutrients, vitamins, fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol/disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings. It will be appreciated that the form and character of the pharmaceutically acceptable carrier is dictated by the amount of active ingredient with which it is to be combined, the route of administration and other well-known variables. The carrier (s) must be "acceptable" in the sense of being compatible with the other ingredients of the formulation and not deleterious to the recipient thereof.

Alternative preparations for administration include sterile aqueous or nonaqueous solutions, suspensions, and emulsions. Examples of non-aqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Various liquid formulations are possible for these delivery methods, including saline, alcohol, DMSO, and water based solutions.

Oral aqueous formulations include excipients, such as pharmaceutical grades of mannitol, lactose, starch, magnesium stearate, sodium saccharine, cellulose, magnesium carbonate and/or the like. These compositions take the form of solutions such as mouthwashes and mouthrinses, further comprising an aqueous carrier such as for example water, alcoholic/aqueous solutions, saline solutions, parenteral vehicles such as sodium chloride, Ringer's dextrose, and the like.

Aqueous mouthwash formulations are well-known to those skilled in the art. Formulations pertaining to mouthwashes and oral rinses are discussed in detail, for example, in U.S. Pat. Nos. 6,387,352, 6,348,187, 6,171,611, 6,165,494, 6,117,417, 5,993,785, 5,695,746, 5,470,561, 4,919,918, U.S. Patent Appl. No. 2004/0076590, U.S. Patent Appl. No. 2003/0152530, and U.S. Patent Appl. No. 2002/0044910, each of which is herein specifically incorporated by reference into this section of the specification and all other sections of the specification.

Other additives may be present in the formulations of the present disclosure, such as flavoring, sweetening or coloring agents, or preservatives. Mint, such as from peppermint or spearmint, cinnamon, *eucalyptus*, citrus, *cassia*, anise and menthol are examples of suitable flavoring agents. Flavoring agents are for example present in the oral compositions in an amount in the range of from 0 to 3%; up to 2%, such as up to 0.5%, e.g., around 0.2%, in the case of liquid compositions.

Sweeteners include artificial or natural sweetening agents, such as sodium saccharin, sucrose, glucose, saccharin, dextrose, levulose, lactose, mannitol, sorbitol, fructose, maltose, xylitol, thaumatin, aspartame, D-tryptophan, dihydrochalcones, acesulfame, and any combination thereof, which may be present in an amount in the range of from 0 to 2%, for example, up to 1% w/w, such as 0.05 to 0.3% w/w of the oral composition.

Coloring agents are suitable natural or synthetic colors, such as titanium dioxide or CI 42090, or mixtures thereof. Coloring agents are preferably present in the compositions in an amount in the range of from 0 to 3%; for example, up to 0.1%, such as up to 0.05%, e.g., around 0.005-0.0005%, in the case of liquid compositions. Of the usual preservatives, sodium benzoate is preferred in concentrations insufficient substantially to alter the pH of the composition, otherwise the amount of buffering agent may need to be adjusted to arrive at the desired pH.

Other optional ingredients include humectants, surfactants (non-ionic, cationic or amphoteric), thickeners, gums and binding agents. A humectant adds body to the formulation and retains moisture in a dentifrice composition. In addition, a humectant helps to prevent microbial deterioration during storage of the formulation. It also assists in maintaining phase stability and provides a way to formulate a transparent or translucent dentifrice.

Suitable humectants include glycerine, xylitol, glycerol and glycols such as propylene glycol, which may be present, for example, in an amount of up to 50% w/w each, but total humectant is in some cases not more than about 60-80% w/w of the composition. For example, liquid compositions may comprise up to about 30% glycerine plus up to about 5%, for example, about 2% w/w xylitol. Surfactants are preferably not anionic and may include polysorbate 20 or cocoamidobetaine or the like in an amount up to about 6%, for example, about 1.5 to 3%, w/w of the composition.

When the oral compositions of the invention are in a liquid form, it is preferred to include a film-forming agent up to about 3% w/w of the oral composition, such as in the range of from 0 to 0.1%, for example, about 0.001 to 0.01%, such as about 0.005% w/w of the oral composition. Suitable film-formers include (in addition to sodium hyaluronate) those sold under the tradename Gantrez.

Liquid nutritional formulations for oral or enteral administration may comprise one or more nutrients such as fats, carbohydrates, proteins, vitamins, and minerals. Many different sources and types of carbohydrates, lipids, proteins, minerals and vitamins are known and can be used in the nutritional liquid embodiments of the present invention, provided that such nutrients are compatible with the added ingredients in the selected formulation, are safe and effective for their intended use, and do not otherwise unduly impair product performance.

These nutritional liquids are for example formulated with sufficient viscosity, flow, or other physical or chemical characteristics to provide a more effective and soothing coating of the mucosa while drinking or administering the nutritional liquid. These nutritional embodiments also in some cases represent a balanced nutritional source suitable for meeting the sole, primary, or supplemental nutrition needs of the individual.

Non-limiting examples of suitable nutritional liquids are described in U.S. Pat. No. 5,700,782 (Hwang et al.); U.S. Pat. No. 5,869,118 (Morris et al.); and U.S. Pat. No. 5,223,285 (DeMichele et al.), which descriptions are incorporated herein by reference in their entireties.

Nutritional proteins suitable for use herein can be hydrolyzed, partially hydrolyzed or non-hydrolyzed, and can be derived from any known or otherwise suitable source such as milk (e.g., casein, whey), animal (e.g., meat, fish), cereal (e.g., rice, corn), vegetable (e.g., soy), or any combination thereof.

Fats or lipids suitable for use in the nutritional liquids include, but are not limited to, coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and any combination thereof. Carbohydrates suitable for use in the nutritional liquids may be simple or complex, lactose-containing or lactose-free, or any combination thereof. Non-limiting examples of suitable carbohydrates include hydrolyzed corn starch, maltodextrin, glucose polymers, sucrose, corn syrup, corn syrup solids, rice-derived carbohydrate, glucose, fructose, lactose, high fructose corn syrup and indigestible oligosaccharides such as fructo-oligosaccharides (FOS), and any combination thereof.

The nutritional liquids may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and any combination thereof.

The nutritional liquids may further comprise any of a variety of minerals known or otherwise suitable for us in patients at risk of or suffering from T1D, non-limiting examples of which include calcium, phosphorus, magnesium iron, selenium, manganese, copper, iodine, sodium, potassium, chloride, and any combination thereof.

The microorganisms and in particular the yeast and bacteria of the present invention can also be formulated as elixirs or solutions for convenient oral or rectal administration or as solutions appropriate for parenteral administration, for instance by intramuscular, subcutaneous or intravenous routes. Additionally, the nucleoside derivatives are also well suited for formulation as a sustained or prolonged release dosage forms, including dosage forms that release active ingredient only or in some cases in a particular part of the intestinal tract, for example over an extended or prolonged period of time to further enhance effectiveness. The coatings, envelopes, and protective matrices in such dosage forms may be made, for example, from polymeric substances or waxes well known in the pharmaceutical arts.

The compositions of the present invention include pharmaceutical dosage forms such as lozenges, troches or pastilles. These are typically discoid-shaped solids containing the active ingredient in a suitably flavored base. The base may be a hard sugar candy, glycerinated gelatin, or the combination of sugar with sufficient mucilage to give it form. Troches are placed in the mouth where they slowly dissolve, liberating the active ingredient for direct contact with the mucosa.

The troche embodiments of the present invention can be prepared, for example, by adding water slowly to a mixture of the powdered active, powdered sugar, and a gum until a pliable mass is formed. A 7% acacia powder can be used to provide sufficient adhesiveness to the mass. The mass is rolled out and the troche pieces cut from the flattened mass, or the mass can be rolled into a cylinder and divided. Each cut or divided piece is shaped and allowed to dry, to thus form the troche dosage form.

If the active ingredient is heat labile, it may be made into a lozenge preparation by compression. For example, the granulation step in the preparation is performed in a manner similar to that used for any compressed tablet. The lozenge is made using heavy compression equipment to give a tablet that is harder than usual as it is desirable for the dosage form to dissolve or disintegrate slowly in the mouth. Ingredients are in some cases selected to promote slow-dissolving characteristics.

In a particular formulation of the present invention, the microorganisms will be incorporated in a bioadhesive carrier containing pregelatinized starch and cross-linked poly (acrylic acid) to form a bioadhesive tablet and a bioadhesive gel suitable for buccal application (i.e., having prolonged bioadhesion and sustained drug delivery.

In an alternative embodiment, a powder mixture of non-pathogenic and non-invasive bacterium according to the invention, bioadhesive polymers (pregelatinized starch and cross-linked poly (acrylic acid) coprocessed via spray drying), sodium stearyl fumarate (lubricant), and silicium dioxide (glidant) is processed into tablets (weight: 100 mg; diameter: 7 mm). The methods for the production of these tablets are well known to the person skilled in the art and has been described before for the successful development of bioadhesive tablets containing various drugs (miconazol, testosterone, fluoride, ciprofloxacin) (Bruschi M. L. and de Freitas O., *Drug Development and Industrial Pharmacy*, 2005 31:293-310). All excipient materials are commercially available in pharmaceutical grades.

To optimize a formulation, the drug load in the tablets and the ratio between starch and poly (acrylic acid) will be varied. Based on previous research, the maximum drug load in the coprocessed bioadhesive carrier is about 60% (w/w) and the starch/poly (acrylic acid) ratio can be varied between 75/25 and 95/5 (w/w). During the optimization study, the bioadhesive properties of the tablets and the drug release from the tablets are the main evaluation parameters, with the standard tablet properties (hardness, friability) as secondary evaluation criteria.

The bacteria are incorporated into an aqueous dispersion of pregelatinized starch and cross-linked poly (acrylic acid). This polymer dispersion is prepared via a standard procedure using a high shear mixer.

Similar to the tablet, the drug load of the gel and the starch/poly (acrylic acid) ratio need to be optimized in order to obtain a gel having optimal adherence to the esophageal mucosa. For a gel, the concentration of the polymers in the dispersion is an additional variable as it determines the viscosity of the gel, hence its muco-adhesive properties.

The model to screen the bioadhesive properties of polymer dispersions to the mucosa of esophagus has been described in detail by Batchelor et al. (*Int. J. Pharm.*, 238:123-132, 2002).

Other routes and forms of administration include food preparations containing the live microorganisms. In some examples, the bioactive polypeptide-expressing microorganism can be included into a dairy product.

The pharmaceutical compositions of the present invention can be prepared by any known or otherwise effective method for formulating or manufacturing the selected dosage form. For example, the microorganisms can be formulated along with common, e.g., pharmaceutically acceptable carriers, such as excipients and diluents, formed into oral tablets, capsules, sprays, lozenges, treated substrates (e.g., oral or topical swabs, pads, or disposable, non-digestible substrate treated with the compositions of the present invention); oral liquids (e.g., suspensions, solutions, emulsions), powders, suppositories, or any other suitable dosage form. In some embodiments, the present disclosure provides a method for the manufacture of a pharmaceutical composition. Exemplary methods include: contacting the microorganism (e.g., the non-pathogenic bacterium) containing the IL-10 gene and the T1D-specific antigen gene (or which is capable of expressing the IL-10 and the T1D-specific antigen) with a pharmaceutically acceptable carrier, thereby forming the pharmaceutical composition. In some examples, the method further includes: growing the microorganism in a medium. The method may further include freeze-drying a liquid containing the microorganism, wherein the liquid optionally includes the pharmaceutically acceptable carrier.

Unit Dosage Forms

The current disclosure further provides unit dosage forms comprising a certain amount of a non-pathogenic microorganism optionally in combination with a food-grade or pharmaceutically acceptable carrier, wherein said non-pathogenic microorganism (e.g., the non-pathogenic gram-positive bacterium) comprises: an exogenous nucleic acid encoding an IL-10 polypeptide; and an exogenous nucleic acid encoding a type-1 diabetes mellitus (T1D)-specific antigen (e.g., PINS). Exemplary unit dosage forms contain from about $1 \times 10^3$ to about $1 \times 10^{14}$ colony-forming units (cfu) of the non-pathogenic microorganism (e.g., a non-pathogenic gram-positive bacterium). Other exemplary unit dosage forms contain from about $1\times10^4$ to about $1\times10^{13}$ colony-forming units (cfu) of a non-pathogenic microorganism (e.g., a non-pathogenic gram-positive bacterium), or from about $1\times10^4$ to about $1\times10^{12}$ colony-forming units (cfu) of a non-pathogenic microorganism (e.g., a non-pathogenic gram-positive bacterium). In other embodiments, the unit dosage form comprises from about $1\times10^5$ to about $1\times10^{12}$ colony-forming units (cfu), or from about $1\times10^6$ to about $1\times10^{12}$ colony-forming units (cfu) of the non-pathogenic microorganism (e.g., the non-pathogenic gram-positive bacterium). In other embodiments, the unit dosage form comprises from about $1\times10^8$ to about $1\times10^{12}$ colony-forming units (cfu), or from about $1\times10^9$ to about $1\times10^{12}$ colony-forming units (cfu) of the non-pathogenic microorganism (e.g., the non-pathogenic gram-positive bacterium). In yet other embodiments, the unit dosage form comprises from about $1\times10^9$ to about $1\times10^{11}$ colony-forming units (cfu), or from about $1\times10^9$ to about $1\times10^{10}$ colony-forming units (cfu) of the non-pathogenic microorganism (e.g., the non-pathogenic gram-positive bacterium). In yet other embodiments, the unit dosage form comprises from about $1\times10^7$ to about $1\times10^{11}$ colony-forming units (cfu), or from about $1\times10^8$ to about $1\times10^{10}$ colony-forming units (cfu) of the non-pathogenic microorganism (e.g., the non-pathogenic gram-positive bacterium).

In yet other embodiments, the unit dosage form comprises from about $1\times10^9$ to about $1\times10^{10}$ colony-forming units (cfu), or from about $1\times10^9$ to about $100\times10^9$ colony-forming units (cfu) of the non-pathogenic microorganism (e.g., the non-pathogenic gram-positive bacterium).

The unit dosage form can have any physical form or shape. In some embodiments, the unit dosage form is adapted for oral administration. In some examples according to these embodiments, the unit dosage form is in the form of a capsule, a tablet, or a granule. Exemplary capsules include capsules filled with micro-granules. In some embodiments, the non-pathogenic microorganism (e.g., the non-pathogenic gram-positive bacterium) contained in the dosage form is in a dry-powder form. For example, the microorganism is in a freeze-dried powder form, which is optionally compacted and coated.

This compositions and methods can be better understood by reference to the Examples that follow, but those skilled in the art will appreciate that these are only illustrative of the invention as described more fully in the numbered embodiments and claims that follow. Additionally, throughout this application, various publications are cited. The disclosures of these publications are hereby incorporated by reference in their entirety.

EXAMPLES

Example 1

Construction of a Clinical-Grade *Lactococcus lactis* Secreting hPINS and hIL10

A *Lactococcus lactis* strain (sAGX0407) secreting human PINS and human IL10 was generated by replacement of the chromosomally-located thymidylate synthase (thyA) gene in an MG1363 parental strain by an expression cassette for human PINS and IL10 using methods previously described. See, e.g., Steidler L. et al., *Nat. Biotechnol.* 2003; 21:785-789; and Steidler L, Rottiers P; Annals of the New York Academy of Sciences 2006; 1072:176-186. Methods to introduce changes into the *L. lactis* chromosome make use of double homologous recombination. A conditionally replicative carrier plasmid derived from pORI19 and containing an erythromycin selection marker, was constructed in the repA+*L. lactis* strain LL108. Carrier plasmids were designed in such way that the cargo of interest was cloned in between up to 1 kb cross over (XO) areas, identical to the ones flanking the wild type sequence on the bacterial chromosome. This plasmid was introduced into MG1363 or any of its derivatives (repA-). Resistant colonies were selected on agar plates containing erythromycin and a first homologous recombination either at the 5' or 3' target sites was verified by PCR screening. Release of erythromycin selection enabled the excision of the carrier plasmid from the bacterial chromosome by a second homologous recombination, at either the 5' or 3' target site. The final genetic structure of the clinical-grade strain was extensively documented by both Sanger and Illumina full genome sequencing. There are no plasmids or residual erythromycin resistance in the final clinical strain. See, e.g., Steidler, L., et al., *Nat. Biotechnol.* 2003, 21(7): 785-789.

sAGX0407 is a derivative of *Lactococcus lactis* (*L. lactis*) MG1363. In sAGX0407:

Thymidylate synthase gene (thyA; Gene ID: 4798358) is absent, to warrant environmental containment (Steidler, L., et al., Nat. Biotechnol. 2003, 21(7): 785-789).

At the position where thyA had been deleted, and downstream of the constitutive promoter of the HU-like DNA-binding protein gene (PhllA; Gene ID: 4797353), a gene encoding the secretion leader of unidentified secreted 45-kDa protein gene (usp45; Gene ID: 4797218; SSusp45) fused to the hil-10 gene, encoding human interleukin-10 (hIL-10; UniProt: P22301, aa 19-178, variant P2A; Steidler, L., et al., Nat. Biotechnol. 2003, 21(7): 785-789) is inserted to allow expression and secretion of hIL-10.

Trehalose-6-phosphate phosphorylase gene (trePP; Gene ID: 4797140) is absent, to allow accumulation of exogenously added trehalose.

Trehalose-6-phosphate phosphatase gene (otsB; Gene ID: 1036914) is positioned downstream of usp45 (Gene ID: 4797218) to facilitate conversion of trehalose-6-phosphate to trehalose. The otsB expression unit was transcriptionally and translationally coupled to usp45 by use of the intergenic region (IR) preceding the highly expressed *L. lactis* MG1363 50S ribosomal protein L30 gene (rpmD; Gene ID: 4797873).

The constitutive promoter of the HU-like DNA-binding protein gene (PhllA; Gene ID: 4797353) is preceding the putative phosphotransferase genes in the trehalose operon (trePTS; llmg_0453 and llmg_0454; Gene ID: 4797778 and Gene ID: 4797093 respectively) to potentiate trehalose uptake.

The gene encoding cellobiose-specific PTS system IIC component (Gene ID: 4796893), ptcC, was disrupted (tga at codon position 30 of 446; tga30). This mutation ascertains trehalose retention after accumulation.

A gene encoding a fusion of usp45 secretion leader (SSusp45) with the pins gene, encoding human proinsulin (PINS; UniProt: P01308, amino acids 25-110) is positioned downstream of the glyceraldehyde 3-phosphate dehydrogenase gene (gapB; Gene ID: 4797877), to allow expression and secretion of PINS. The pins expression unit was transcriptionally and translationally coupled to gapB by use of IRrpmD.

All genetic traits of sAGX0407 reside on the bacterial chromosome. The genetic background of sAGX0407 provides:

Constitutive secretion of PINS and hIL-10.

Strict dependence on exogenously added thymidine for growth and survival.

The capacity to accumulate and retain trehalose and so acquire the capacity to resist bile acid toxicity.

Figure 18:
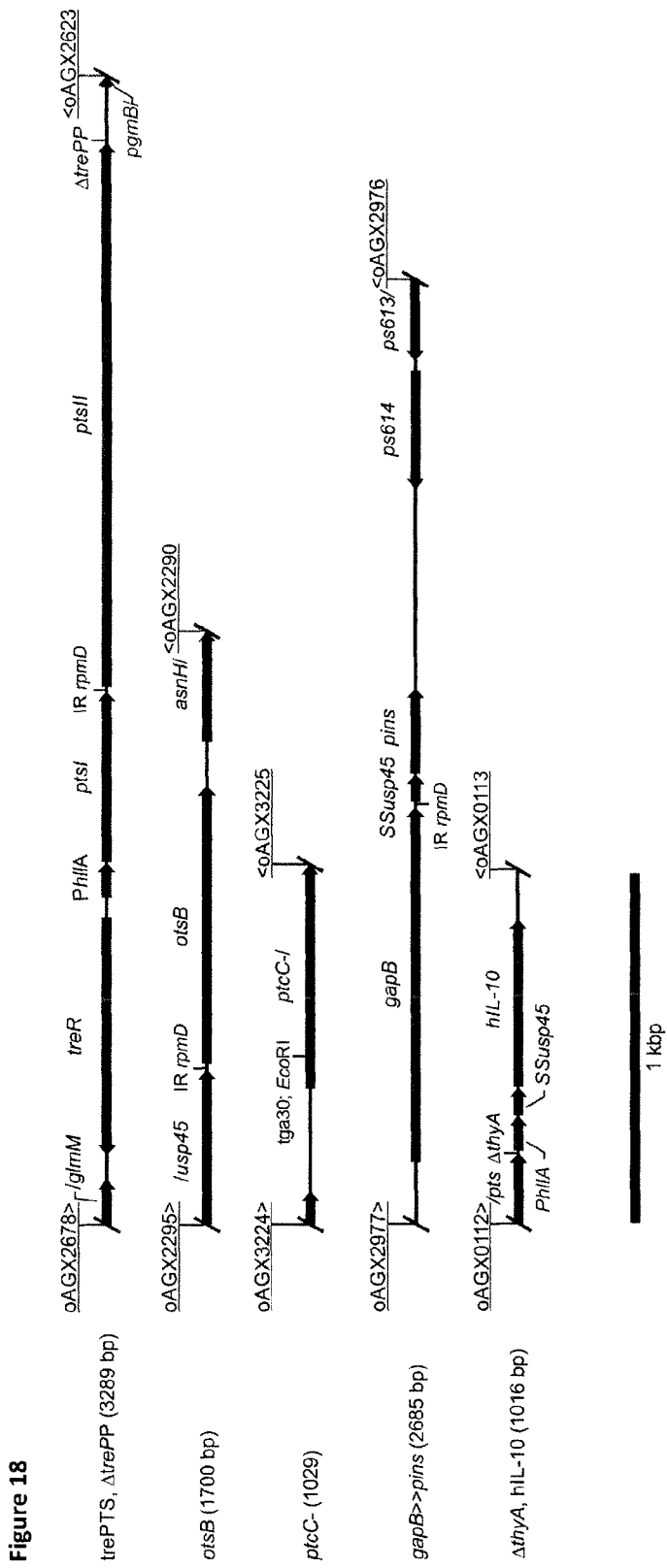
FIG. 18: Schematic overview of relevant genetic loci of sAGX0407 as described: trePTS, ΔtrePP; otsB; ptcC-; gapB>>pins and ΔthyA, hIL-10 with indication of the relevant oligonucleotide binding sites (oAGXno), EcoRI restriction site, (/truncated/) genetic characters, intergenic regions (IR), PCR amplification product sizes (bp).

FIG. 18 shows a schematic overview of relevant genetic loci of sAGX0407 as described: trePTS, ΔtrePP; otsB; ptcC-; gapB>>pins and ΔthyA, hIL-10 with indication of the relevant oligonucleotide binding sites (oAGXno), EcoRI restriction site, (/truncated/) genetic characters, intergenic regions (IR), PCR amplification product sizes (bp).

trePTS, ΔtrePP

Deletion of trehalose-6-phosphate phosphorylase gene (trePP; Gene ID: 4797140); Insertion of the constitutive promoter of the HU-like DNA-binding protein gene (PhllA; Gene ID: 4797353) to precede the putative phosphotransferase genes in the trehalose operon (trePTS; llmg_0453 and llmg_0454; ptsI and ptsII; Gene ID: 4797778 and Gene ID: 4797093 respectively), insertion of the intergenic region preceding the highly expressed *L. lactis* MG1363 50S ribosomal protein L30 gene (rpmD; Gene ID: 4797873) in-between ptsI and ptsII (FIGS. 13A, 13B, and 13C).

otsB

Insertion of trehalose-6-phosphate phosphatase gene (otsB; Gene ID: 1036914) downstream of unidentified secreted 45-kDa protein gene (usp45; Gene ID: 4797218). Insertion of the intergenic region preceding the highly expressed *L. lactis* MG1363 50S ribosomal protein L30 gene (rpmD; Gene ID: 4797873) between usp45 and otsB. (FIGS. 14A and 14B).

ptcC—

Insertion of tga at codon position 30 of 446 (tga30), alongside with the introduction of an EcoRI restriction site, to disrupt the gene encoding cellobiose-specific PTS system IIC component (ptcC; Gene ID: 4796893). (FIGS. 15A and 15B)

gapB>>Pins

Insertion of a gene encoding a fusion of usp45 secretion leader (SSusp45) with the pins gene, encoding human proinsulin (PINS; UniProt: P01308, amino acids 25-110), downstream of the highly expressed glyceraldehyde 3-phosphate dehydrogenase gene (gapB; Gene ID: 4797877). Insertion of the intergenic region preceding the highly expressed *L. lactis* MG1363 50S ribosomal protein L30 gene (rpmD; Gene ID: 4797873) between gapB and pins (FIGS. 12A, 12B, and 16)

ΔthyA, hIL-10

Deletion of thymidylate synthase gene (thyA; Gene ID: 4798358). Downstream of the constitutive promoter of the HU-like DNA-binding protein gene (PhllA; Gene ID: 4797353), insertion of a gene encoding a fusion of SSusp45 with the hil-10 gene, encoding human interleukin-10 (hIL-10; UniProt: P22301, aa 19-178, variant P2A, Steidler et al., *Nat. Biotechnol.* 2003, 21(7): 785-789) is inserted to allow expression and secretion of hIL-10 (FIG. 17).

Example 2

Treatment of Diabetes in Mice

NOD mice were screened for the onset of diabetes by evaluating glucose levels in urine (Diastix® Reagent strips, Bayer, Leverkusen, Germany) and venous blood (Accu-Check®, Roche Diagnostics, Vilvoorde, Belgium). Mice were diagnosed as diabetic when having glucosuria and two consecutive blood glucose measurements exceeding 200 mg/dl. Upon diabetes determination, NOD or NOD transgenic mice were treated for 5 consecutive days intravenously (i.v.) (day 0-4; 2.5 µg/mouse) with hamster anti-mouse CD3 antibodies (clone 145-2C11, BioXCell, West Lebanon, N.H.). This therapy was given in combination with oral administration of either plasmid-driven or clinical-grade *L. lactis* strains ($2 \times 10^9$ cfu) 5 times per week during 6 weeks. Control mice were left untreated. Individual blood glucose concentrations at the start of treatment were recorded. Mice were tested 3 times weekly for their weight and blood glucose status. Remission was defined as the absence of glucosuria and a return to normal blood glucose concentrations. Experimental animals were sacrificed immediately or long after stopping therapy (6 or 14 weeks after treatment initiation). Peripheral blood, lymph organs and pancreas were harvested, and single cells were assessed for phenotyping as described in the Supplemental Research Design and Methods. Mice were removed from the study prior to the 14-week endpoint when blood glucose concentrations exceeded 600 mg/dl in two consecutive measurements.

Glucose Tolerance Test

One or two weeks prior to sacrifice intraperitoneal glucose tolerance tests (IPGTT) were performed. Mice were fasted for 16 hours, injected intraperitoneally (i.p.) with glucose (2 g/kg) and blood glucose concentrations were measured at 0, 15, 30, 60, 90 and 120 minutes.

IAA Measurement

Heparinized plasma was collected from new-onset diabetic NOD mice before treatment randomization and at therapy discontinuation, and IAAs were analyzed at the UF Department of Pathology, Immunology and Laboratory Medicine, College of Medicine, Gainesville, Fla., as described in Robert S. et al., *Diabetes* 2014, 63: 2876-2887.

In Vivo Blocking of CTLA4 and TGF-β

Mice tolerized by *L. lactis*-based therapy were injected intraperitoneally (i.p.) after therapy withdrawal with blocking antibodies against CTLA4 (clone UC10-4F10, Bioceros) and TGF-β (clone 1D11.16.8, BioXCell) in the following dose regimen: 250 µg at day 1 and 3 and then 100 µg at day 6, 8, 10, 13 and 18 for CTLA4; 200 µg 3 times per week during 3 weeks for TGF-0. Blood glucose concentrations were measured daily up to 25 days after first injection.

Adoptive Transfer of Diabetes.

To assess the diabetogenic potential of Teff cells, total T cells from spleen ($1 \times 10^7$ cells) of new-onset diabetic controls, responders and non-responders of *L. lactis*-based therapy were transferred i.v. (intravenously) into the tail veins of 6- to 8-week-old immune-deficient NOD-scid mice. Recipient mice were monitored twice weekly for the development of diabetes up to 100 days post-cell transfer.

DT-Mediated Depletion of Foxp3+ T Cells in NOD.Foxp3.DTR Mice

NOD.Foxp3.DTR mice (expressing the human diphtheria toxin receptor (DTR) under the control of Foxp3 transcriptional control elements) allow for the depletion of Foxp3+ T cells upon DT (diphtheria toxin) administration. See, e.g., Feuerer M. et al., How punctual ablation of regulatory T cells unleashes an autoimmune lesion within the pancreatic islets. *Immunity* 2009; 31:654-664. For Treg depletion, NOD.Foxp3.DTR mice (unmanipulated or tolerized after stopping the *L. lactis*-based therapy) were injected i.p. with 40 µg/kg bodyweight of DT (Sigma) on days 1, 2, 4, and 7 and examined on day 8. Following DT injections, weight, urine and blood glucose status of mice were monitored.

Foxp3+ T cells were monitored in peripheral blood and pancreas by flow cytometry and histology respectively as described. See, e.g., Tian L. et al., Foxp3(+) regulatory T cells exert asymmetric control over murine helper responses by inducing Th2 cell apoptosis. *Blood* 2011; 118:1845-1853.

FOXP3-Inhibitory Peptide P60 in Combination with *L. lactis*-Based Therapy

P60 (a 15-mer synthetic peptide that can bind to and block FOXP3, i.p. 50 μg/dose daily, up to 14 doses) was given either at start of the *L. lactis*-based therapy, as previously described. See, e.g., Casares N. et al., A peptide inhibitor of FOXP3 impairs regulatory T cell activity and improves vaccine efficacy in mice. *Journal of Immunology* 2010, 185:5150-5159.

Histology of Pancreas and Insulitis Grading

Six-μm sections from formalin-fixed paraffin-embedded pancreas tissues were cut and collected 100-μm apart, then stained with hematoxylin eosin. Islets were observed under light microscopy at 20× or 40×, enumerated and graded by an independent investigator in blinded fashion. At least 25 islets per pancreatic sample were scored for islet infiltration as follows: 0, no infiltration; 1, peri-insulitis; 2, islets with lymphocyte infiltration in less than 50% of the area, 3, islets with lymphocyte infiltration in more than 50% of the area or completely destroyed.

Islet-Resident Foxp3+ T Cell Detection

Pancreas tissues were snap-frozen in 2-methyl-butane 99% and cut into 12-μm tissue sections. Foxp3+ T cell detection was performed as described. See, e.g., Takiishi T. et al., Reversal of autoimmune diabetes by restoration of antigen-specific tolerance using genetically modified *Lactococcus lactis* in mice. *J. Clin. Invest.* 2012, 122:1717-1725.

Statistics

All data were analyzed using GraphPad Prism 6 (Graphpad Prism, La Jolla, Calif.). Survival curves were computed with Kaplan-Meier test and compared with log-rank test. Groups were analyzed by ANOVA (non-parametric Kruskal-Wallis test) with Dunn's multiple comparison or with Mann-Whitney U test, as appropriate. Error bars represent SEM. Unless otherwise indicated, differences are not significant (ns). * $P<0.05$,  $P<0.01$, * $P<0.001$, **** $P<0.0001$.

Bacteria and Media

*L. lactis*-pT1NX is an MG1363 strain containing the empty vector pT1NX, and served as control. The plasmid-driven *L. lactis* strain (sAGX0328 secreting plasmid-encoded human PINS and chromosomally-integrated IL10) was cultured as previously described. See, e.g., Takiishi T. et al., *J. Clin. Invest.* 2012, 122:1717-17253. As growth and survival of thyA-deficient *L. lactis* strains depends on the presence of thymidine in the growth medium, the clinical-grade *L. lactis* (secreting chromosomally-integrated human PINS and IL10) was cultured in GM17T, i.e. M17 broth (BD, Franklin Lakes, N.J.), supplemented with 0.5% glucose (Merck KGaA, Darmstadt, Germany) and 200 μM thymidine (Sigma, St. Louis, Mo.). For intragastric inoculations, stock suspensions were diluted 1000-fold in growth media and incubated for 16 hours at 30° C., reaching a saturation density of $2\times10^9$ cfu/ml. Bacteria were harvested by centrifugation and concentrated 10-fold in BM9 medium. Treatment doses consisted of 100 μl of this bacterial suspension. For intragastric inoculations, stock suspensions were diluted 1000-fold in growth media and incubated for 16 hours at 30° C., reaching a saturation density of $2\times10^9$ cfu/ml. Bacteria were harvested by centrifugation and concentrated 10-fold in BM9 medium. Treatment doses consisted of 100 μl of this bacterial suspension.

Flow Cytometry

Peripheral blood and specified organs were harvested 6 weeks after treatment initiation, processed and incubated with fluorochrome-labeled antibodies or matching isotype controls for flow cytometric analysis. Tregs were stained with anti-mouse CD3 (145-2C11), CD4 (GK1.5), CD8a (53-6.7), CD25 (PC61.5 or 7D4 (BD, Erembodegem, Belgium)), and FR4 (eBio12A5) (all from eBioscience, San Diego, Calif., unless specified) for 20 min on ice. Intracellular staining antibodies against Foxp3 (FJK-16s) and CTLA4 (UC10-4B9) were from eBioscience and used according to the manufacturer's instructions. Naïve, effector memory and central memory T cells were determined by staining with anti-mouse CD3 (145-2C11), CD4 (GK1.5), CD8a (53-6.7), CD44 (IM7), CD62L (MEL-14), CD69 (H1.2F3), and CCR7 (4B12). Cells were analyzed in a Gallios™ flow cytometer with Kaluza (Beckman Coulter, Suarlēe, Belgium) or FlowJo software (Treestar, Ashland, Oreg.).

In vitro Suppressor Assays

Pathogenic CD4+CD25− Teff cells were isolated from spleen cells of 10-week old NOD mice by negative selection using antibodies to CD25, CD8a, B220, CD11c, CD11b, MHC class II, and sheep anti-rat IgG Dynabeads (Invitrogen, Merelbeke, Belgium). CD4+CD25+Foxp3+ and CD4+CD25−Foxp3+ Tregs were isolated from pooled lymph node and spleen cells of NOD.Foxp3.hCD2 mice (harboring a human CD2-CD52 fusion protein, along with an intra-ribosomal entry site, into the 3' untranslated region of the endogenous foxp3 locus). See, e.g., Culina S. et al., *Clin. Dev. Immunol.* 2011; 2011:286248. Briefly, cell samples were passed through a 70-μm cell strainer and suspended in RPMI1640 medium, centrifuged for 5 min at 1,500 rpm and suspended in RPMI1640 medium. The resultant cell suspension was counted, washed and first depleted of CD8α+, B220+, CD11c+, CD11b+ and MHC class+, and adherent cells by panning and stained with biotin-conjugated anti-CD4 and anti-hCD2 antibodies. Cells were then incubated with anti-biotin microbeads (Miltenyi Biotec B.V., Leiden, The Netherlands) and separated on LS or MS columns (Miltenyi Biotech). The resulting hCD2+ or hCD2− cells were further purified with anti-CD25 antibodies. In vitro polyclonal suppressor assays were conducted. Cytokines (IFN-γ, IL10 and TGF-β) were measured in cell-free supernatants by multiplex immunoassay (Mesoscale Discovery, Rockville, Mass.) or flow cytometric bead array (Bender MedSystems FlowCytomix™, eBioscience) as described. See, e.g., Ludvigsson J. et al., GAD65 antigen therapy in recently diagnosed type 1 diabetes mellitus. *N. Engl. J. Med.* 2012, 366:433-442.

Blocking antibodies against CTLA4 (UC10-4F10), IL10 (clone JES5-2A5, BioXCell), and TGF-β (clone 1D11.16.8, which neutralizes all three mammalian TGF-β isoforms (β1, β2, and β3), BioXCell) were added to cultures at a concentration of 10 μg/ml.

Results

A Clinical-Grade Self-Contained *L. lactis* Vaccine Combined with Low-Dose Anti-CD3 Stably Reversed New-Onset Diabetes, Preserved Residual Beta-Cell Function and Halted Insulitis Progression in NOD Mice.

Using a clinical-grade self-containing *L. lactis* strain secreting human PINS along with IL10 in combination with sub-therapeutic doses of anti-CD3 antibodies, 66% (23 out of 35) of mice reverted to normoglycemia for at least 14 weeks after disease onset, which was statistically significantly superior to 43% of mice treated by anti-CD3 alone (FIG. 1A). Animals left untreated (n=20) or treated with the empty vector bacterial strain *L. lactis*-pT1NX (n=9) remained hyperglycemic and were sacrificed when 20% of their starting body weight was lost. Monotherapy with the clinical-grade or plasmid-driven *L. lactis* strain secreting PINS and IL-10 was significantly less effective than the combination with anti-CD3 (0% (n=8) and 17% (n=8) respectively) (FIG. 1A).

Figure 1B:
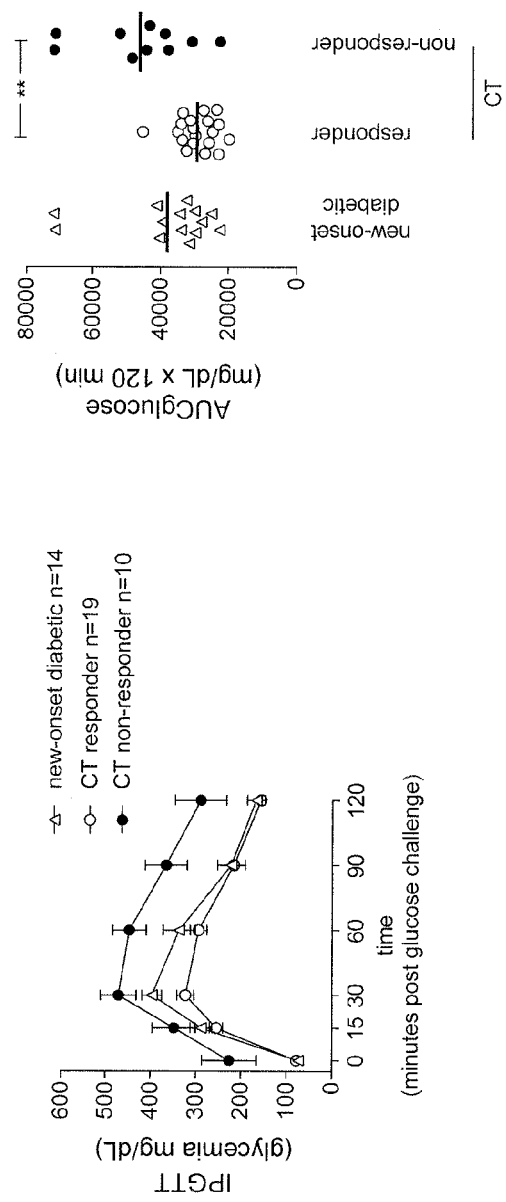
FIG. 1B depicts graphs demonstrating that an exemplary antigen-specific therapy according to the present disclosure preserves residual beta-cell function in NOD mice. Intraperitoneal glucose tolerance tests (IPGTTs) were performed on new-onset diabetic NOD mice in addition to L. lactis-based combination therapy (CT)-treated mice (both responders and non-responders) 1 to 2 weeks prior to treatment termination. Corresponding area under the glucose tolerance curve (AUC glucose; mg/dl×120 minutes) over 2 hours is shown. A responder is used herein as a subject that returns to normoglycemia (e.g. no glucosuria and blood glucose measurements >200 mg/dl) following treatment.

During follow up, new-onset diabetic controls, mice protected by *L. lactis*-based therapy, and mice not protected by such therapy, were subjected to IPGTT and sacrificed 6 weeks after treatment initiation at which time their pancreas tissues were assessed by histology. Only in the successfully treated animals, residual beta-cell function (i.e. assessed as area under glucose tolerance curve (AUCglucose)) was preserved and smaller proportions of islets had severe insulitis (FIG. 1B). Of interest, at the end of the combination therapy no difference in the severity of insulitis was observed between responders and non-responders (FIG. 1C).

Starting Glycemia and IAA Positivity Predict Therapeutic Success of *L. lactis*-Based Therapy.

Figure 2A:
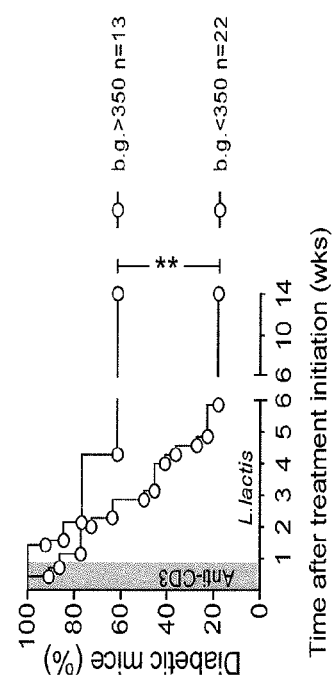
FIG. 2A is a graph showing diabetes remission rate according to starting blood glucose concentrations. New-onset diabetic NOD mice were stratified based on starting glycemia under or above 350 mg/dl at study entry. Shown is the percentage of mice that remained diabetic after combination treatment (CT) with a clinical-grade L. lactis strain of the present disclosure. In the Kaplan-Meier survival curve, statistical significance between groups was determined by Mantel-Cox log-rank test; ** P<0.01.
Figure 2B:
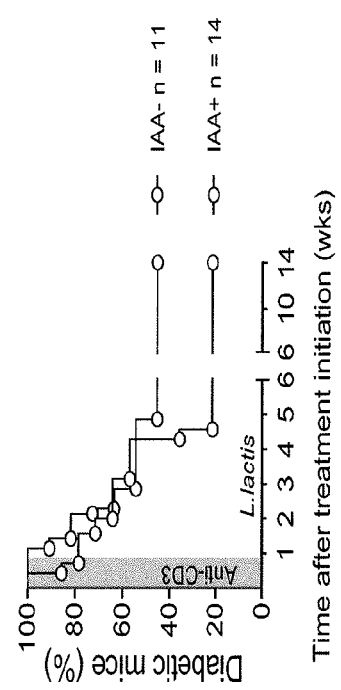
FIG. 2B is a graph showing the diabetes remission rate according to insulin autoantibody (IAA) positivity at study entry. New-onset diabetic NOD mice were stratified based on starting glycemia under or above 350 mg/dl at study entry. Shown is the percentage of mice that remained diabetic after combination treatment (CT) with a clinical-grade L. lactis strain of the present disclosure.

No influence of age or gender of mice was observed on therapeutic success of the *L. lactis*-based therapy. However, glycemic concentrations at the beginning of therapy predicted success with 82% of mice starting with a glycemia below 350 mg/dl cured (n=22), in comparison to 38% of mice with a starting glycemia above 350 mg/dl (n=13) (FIG. 2A). In addition, positivity for IAAs at entry seemed to correlate with therapeutic success (FIG. 2B). Interestingly, mice with blood glucose concentrations <350 mg/dl and IAA positivity at therapy start had a clearly superior diabetes remission rate (89%, n=8) than mice with blood glucose levels >350 mg/dl and being IAA negative (33%; n=5; P=0.07). (FIG. 2C). Moreover, the *L. lactis*-based therapy significantly decreased IAA levels, particularly in mice responsive to the therapy (FIG. 2D).

*L. lactis*-Based Therapy Induces Higher Levels of Foxp3$^+$ T Cells with Regulatory Capacity but No Changes in Teff Cells.

Figure 3A:
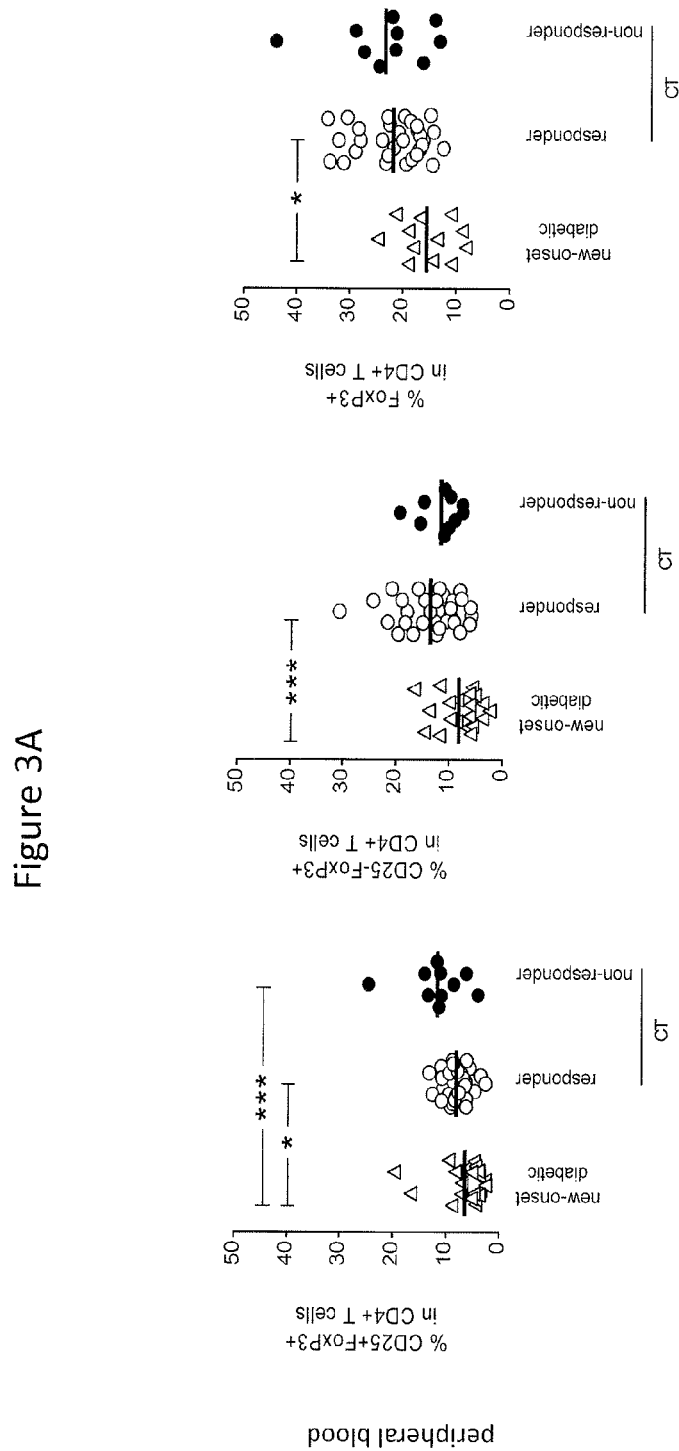
FIG. 3A depicts graphs showing that L. lactis-based combination therapy induces higher levels of Foxp3$^+$ T cells. The percentages of CD25$^+$Foxp3$^+$ cells (left panel), CD25$^-$Foxp3$^+$ cells (middle panel), and total Foxp3$^+$ cells (right panel) within the CD4$^+$ T cell population in peripheral blood of new-onset diabetic and L. lactis-based combination therapy (CT)-treated mice (both responders and non-responders). Each symbol represents one mouse, and horizontal bars indicate the median value. Statistical significance was calculated using Mann-Whitney t-test; * P<0.05,  P<0.01, *, P<0.001; ****, P<0.0001.
Figure 3B:
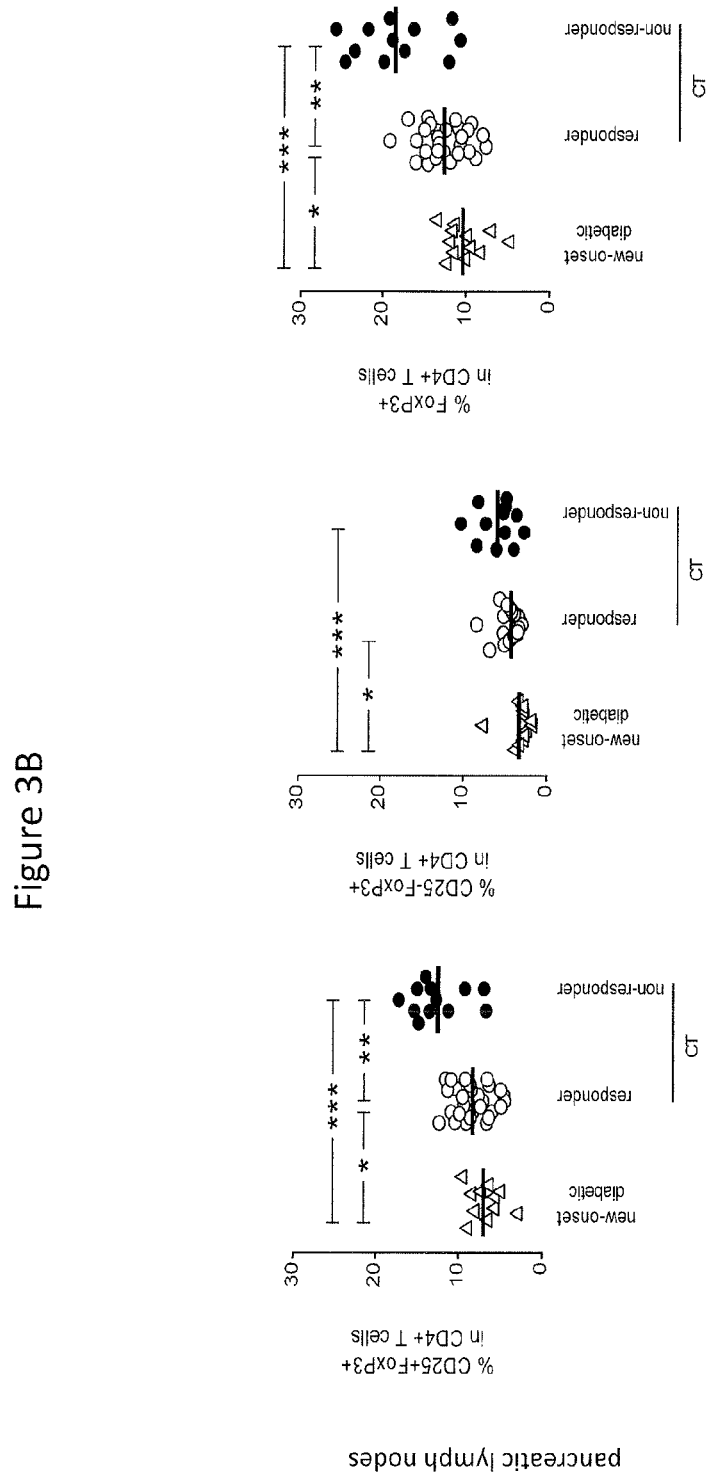
FIG. 3B depicts graphs showing L. lactis-based combination therapy induces higher levels of Foxp3$^+$ T cells. The percentages of CD25⁺Foxp3⁺ cells (left panel), CD25⁻Foxp3⁺ cells (middle panel), and total Foxp3⁺ cells (right panel) within the CD4⁺ T cell population in pancreatic draining lymph nodes of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * $P<0.05$,  $P<0.01$, *, $P<0.001$; ****, $P<0.0001$.
Figure 3C:
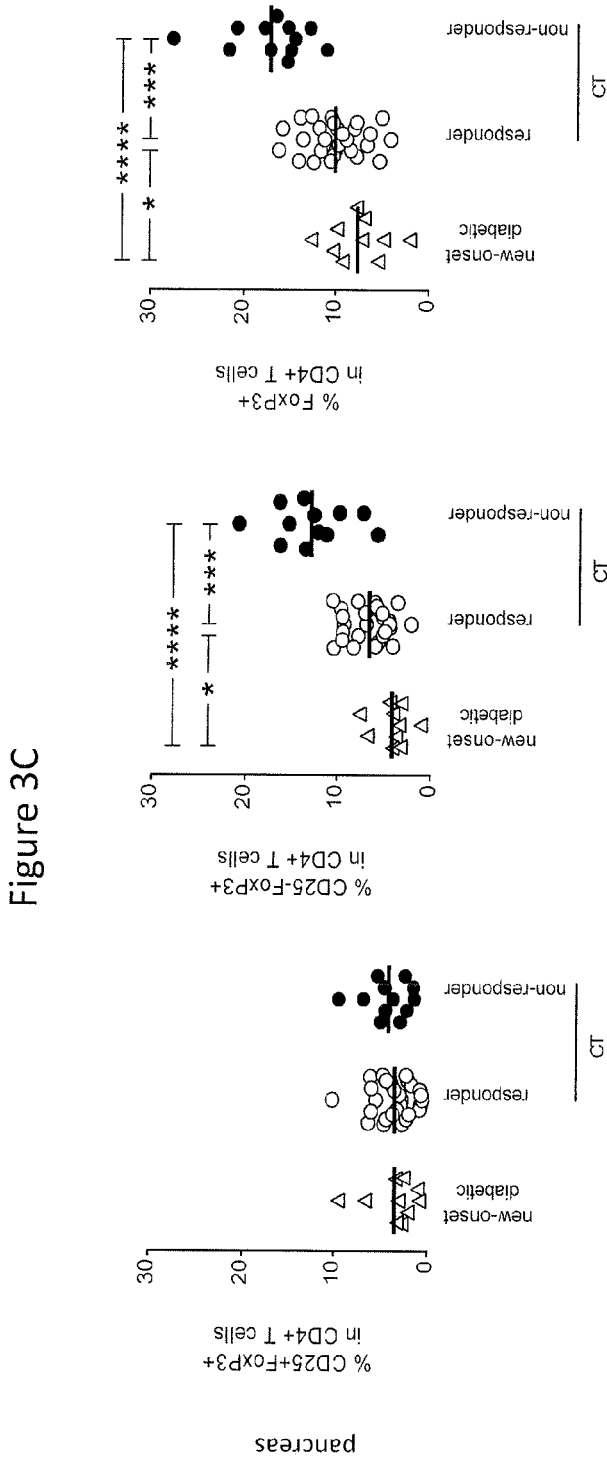
FIG. 3C depicts graphs showing *L. lactis*-based combination therapy induces higher levels of Foxp3⁺ T cells. The percentages of CD25⁺Foxp3⁺ cells (left panel), CD25⁻Foxp3⁺ cells (middle panel), and total Foxp3⁺ cells (right panel) within the CD4⁺ T cell population in pancreas of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * $P<0.05$,  $P<0.01$, *, $P<0.001$; ****, $P<0.0001$.
Figure 3D:
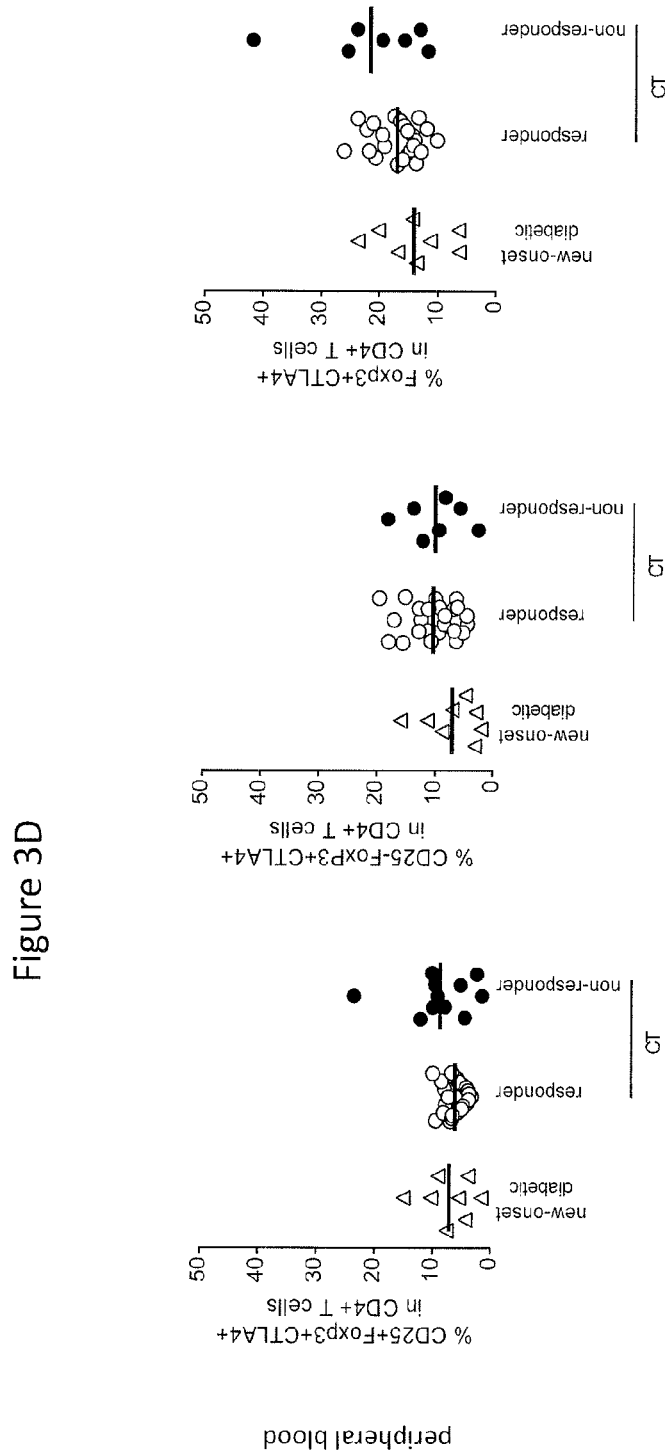
FIG. 3D depicts graphs showing *L. lactis*-based combination therapy induces higher levels of Foxp3⁺ T cells. The percentages of CD25⁺Foxp3⁺CTLA4⁺ cells (left panel), CD25⁻Foxp3⁺CTLA4⁺ cells (middle panel), and Foxp3⁺CTLA4⁺ cells (right panel) within the CD4⁺ T cell population in peripheral blood of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * $P<0.05$,  $P<0.01$, *, $P<0.001$; ****, $P<0.0001$.
Figure 3E:
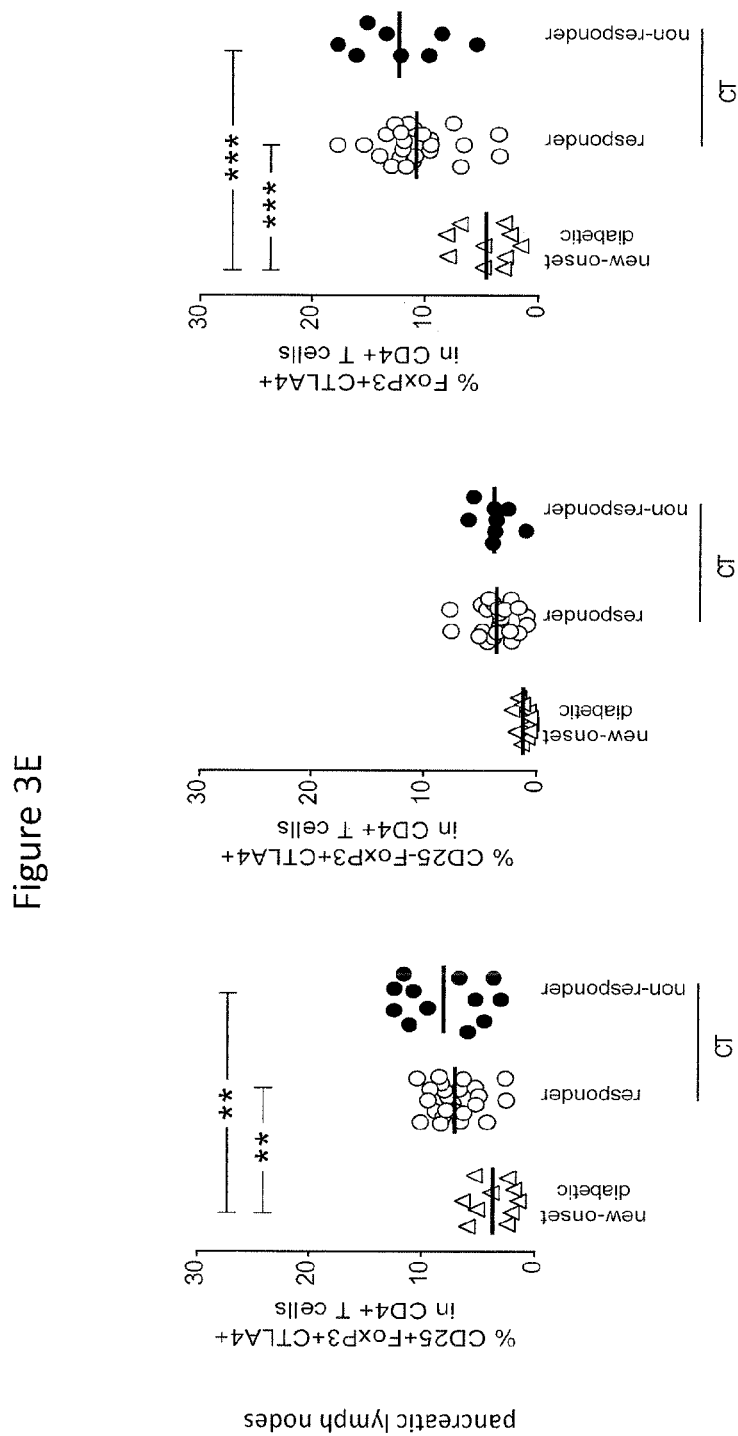
FIG. 3E depicts graphs showing *L. lactis*-based combination therapy induces higher levels of Foxp3⁺ T cells. The percentages of CD25⁺Foxp3⁺CTLA4⁺ cells (left panel), CD25⁻Foxp3⁺CTLA4⁺ cells (middle panel), and Foxp3⁺CTLA4⁺ cells (right panel) within the CD4⁺ T cell population in pancreatic draining lymph nodes of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * $P<0.05$,  $P<0.01$, *, $P<0.001$; ****, $P<0.0001$.
Figure 3F:
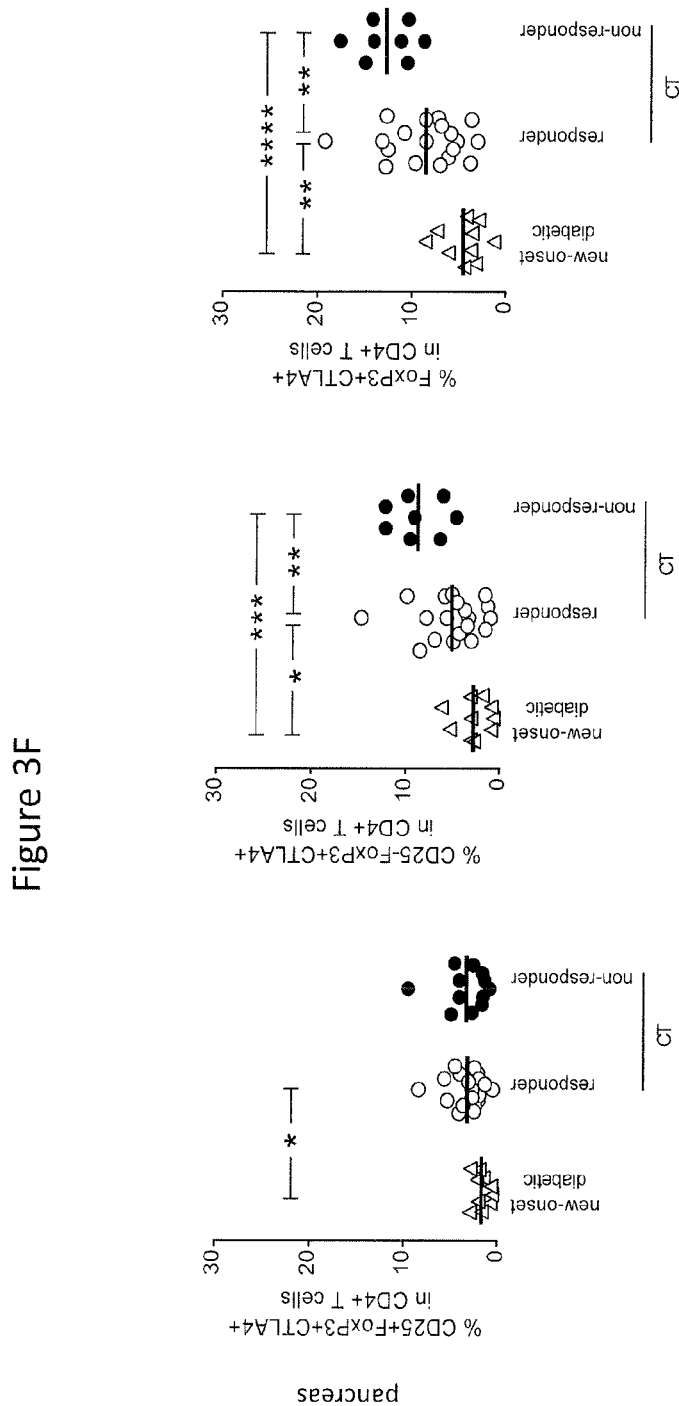
FIG. 3F depicts graphs showing *L. lactis*-based combination therapy induces higher levels of Foxp3⁺ T cells. The percentages of CD25⁺Foxp3⁺CTLA4⁺ cells (left panel), CD25⁻Foxp3⁺CTLA4⁺ cells (middle panel), and Foxp3⁺CTLA4⁺ cells (right panel) within the CD4⁺ T cell population in pancreas of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * $P<0.05$,  $P<0.01$, *, $P<0.001$; ****, $P<0.0001$.
Figure 8A:
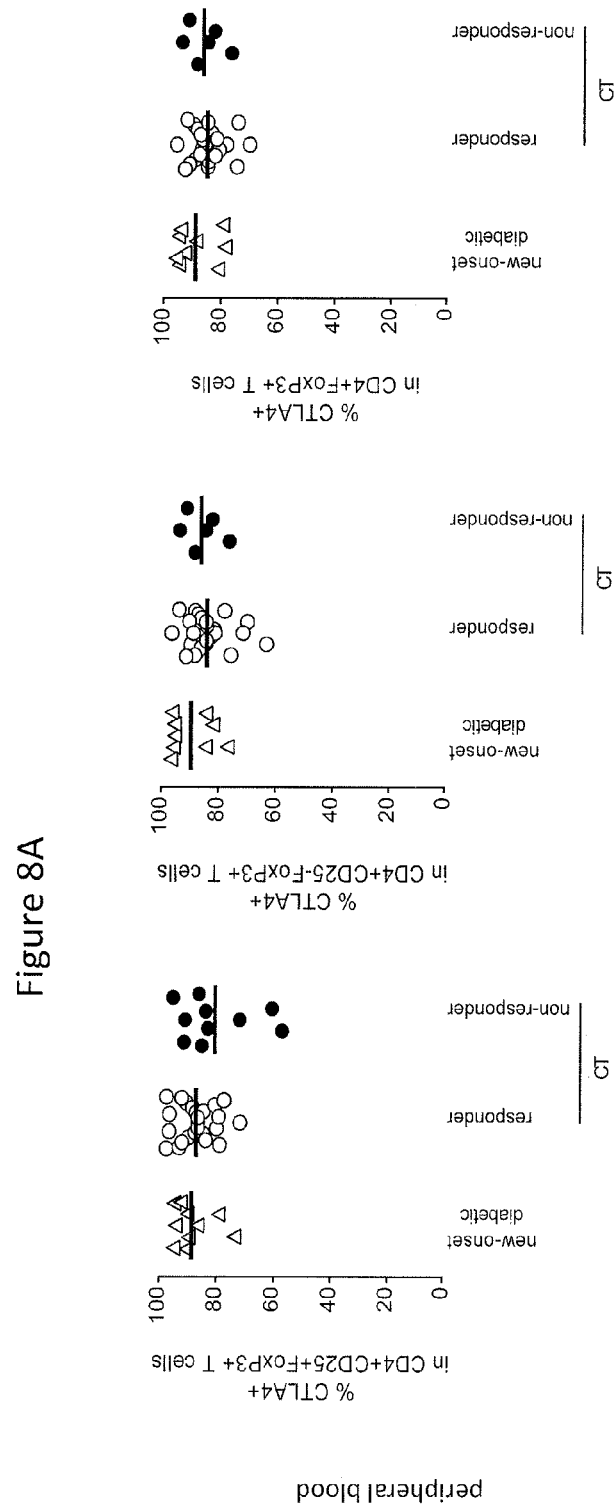
FIG. 8A depicts graphs showing the percentages of CTLA4+ cells within the CD4+CD25+Foxp3+ (left), CD4+CD25−Foxp3+ (middle), and CD4+Foxp3+ (right) T cell population in peripheral blood of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * P<0.05,  P<0.01, *, P<0.001; ****, P<0.0001.
Figure 8B:
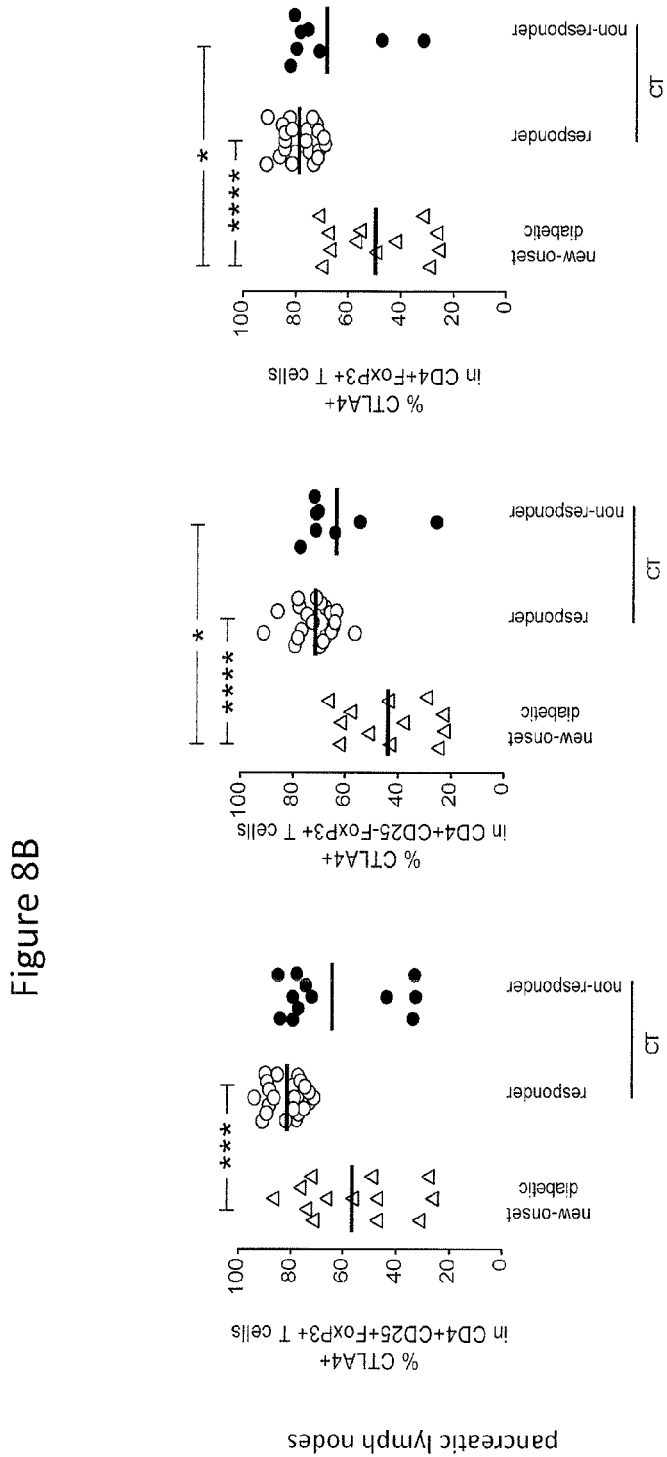
FIG. 8B depicts graphs showing the percentages of CTLA4+ cells within the CD4+CD25+Foxp3+ (left), CD4+CD25−Foxp3+ (middle), and CD4+Foxp3+ (right) T cell population in pancreatic draining lymph nodes of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * P<0.05,  P<0.01, *, P<0.001; ****, P<0.0001.
Figure 8C:
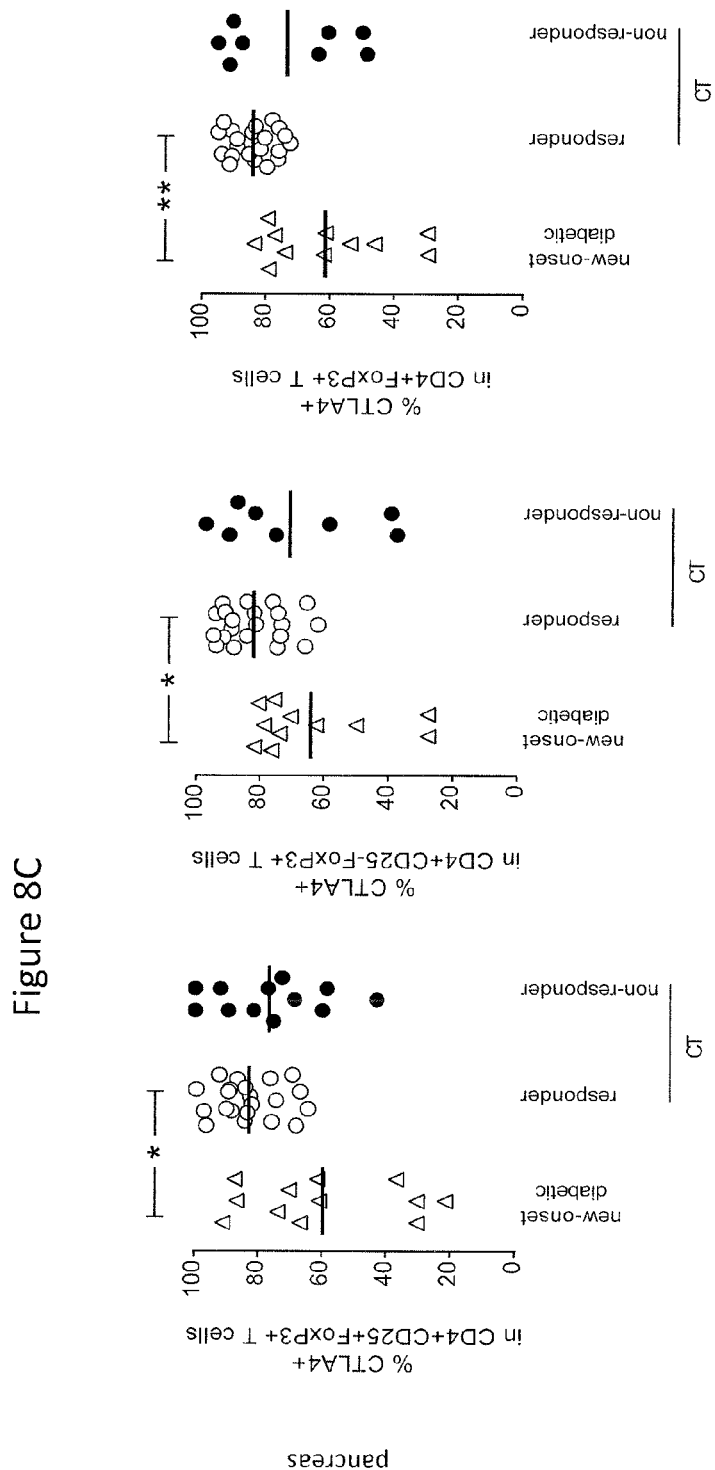
FIG. 8C depicts graphs showing the percentage of CTLA4+ cells within the CD4+CD25+Foxp3+ (left), CD4+CD25−Foxp3+ (middle), and CD4+Foxp3+ (right) T cell population in pancreas of new-onset diabetic and *L. lactis*-based combination therapy (CT)-treated mice (both responders and non-responders). Each symbol represents one mouse, and horizontal bars indicate the median value. Statistical significance was calculated using Mann-Whitney t-test; * P<0.05,  P<0.01, *, P<0.001; ****, P<0.0001.
Figure 9:
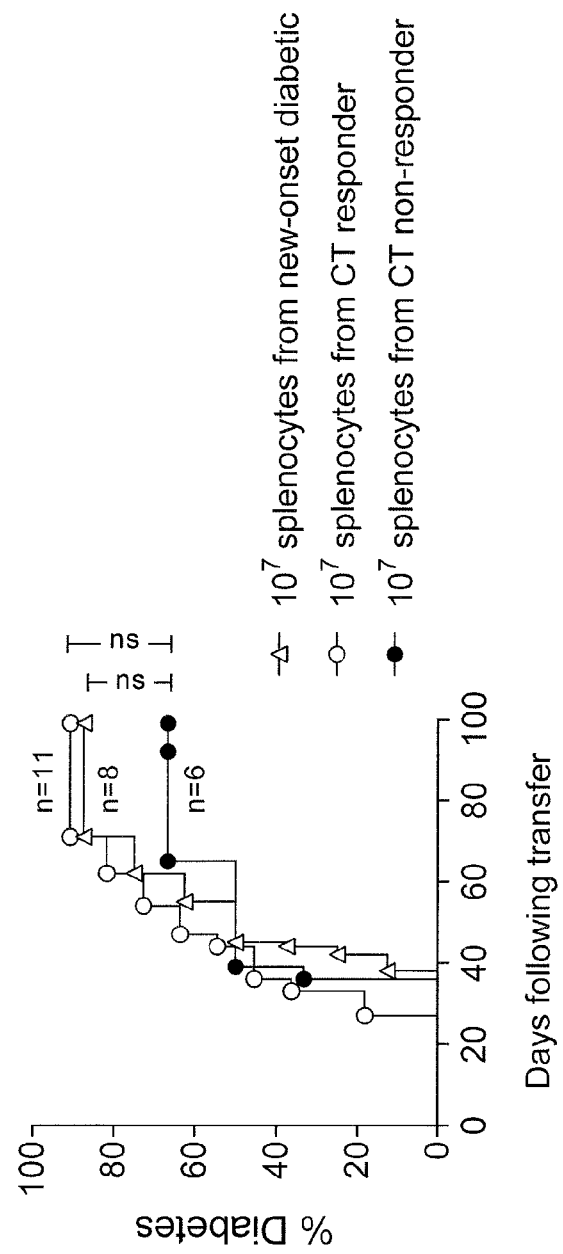
FIG. 9 is graph showing that *L. lactis*-based combination therapy-tolerized mice are not depleted in pathogenic T effector cells. Adoptive transfer of total splenocytes ($1 \times 10^7$) isolated from overtly diabetic (white diamonds), combination therapy (CT) responders (white circles) or non-responders (crossed circles). Statistical calculations were performed using Mantel-Cox log-rank test; "ns": not significant.

The mechanisms underlying disease remission induced by the *L. lactis*-based treatment were investigated by dissociating between the therapeutic immune effects in mice responsive or not to the intervention. We found that the percentages of CD4$^+$Foxp3$^+$ (both CD25$^+$ and CD25$^-$) T cells observed in the peripheral blood (FIG. 3A), the pancreatic draining lymph nodes (FIG. 3B), and the pancreas (FIG. 3C) were significantly higher in mice treated with the *L. lactis*-based therapy in comparison to untreated controls. Interestingly, in the pancreatic draining lymph nodes and pancreas, but not in peripheral blood, the increased frequency of CD4$^+$Foxp3$^+$ T cells was less pronounced in responders than non-responders. Using multicolor flow cytometry, we identified that most CD4$^+$Foxp3$^+$ Tregs were positive for CTLA4 and that the expression of this inhibitory marker was significantly higher in pancreatic draining lymph nodes (for both responders and non-responders) and pancreas (only for responders) of treated mice compared to untreated controls (FIGS. 8B and 8C). Of interest, no differences in the percentages of CD4$^+$Foxp3$^+$CTLA4$^+$ T cells were observed in the peripheral blood of treated mice compared to untreated controls (FIG. 3D). The percentages of naïve (CD44$^-$CD62L$^+$CCR7$^+$), effector memory (CD44$^+$CD62L$^-$CCR7$^-$) and central memory (CD44$^+$CD62L$^+$CCR7$^+$) CD4$^+$ T cells were not altered in any recipient group with respect to therapeutic success or failure. Transfer of splenocytes from responders and non-responders of *L. lactis*-based treatment caused diabetes in NOD-scid recipients with similar disease kinetics as transfer of splenocytes isolated from untreated new-onset diabetic controls, suggesting that circulating diabetogenic cells were not depleted from treated mice (FIG. 9).

Diabetes Reversal Induced by *L. lactis*-Based Therapy is Accompanied by and Depends on the Generation of Functional Foxp3$^+$ Tregs.

Figure 4:
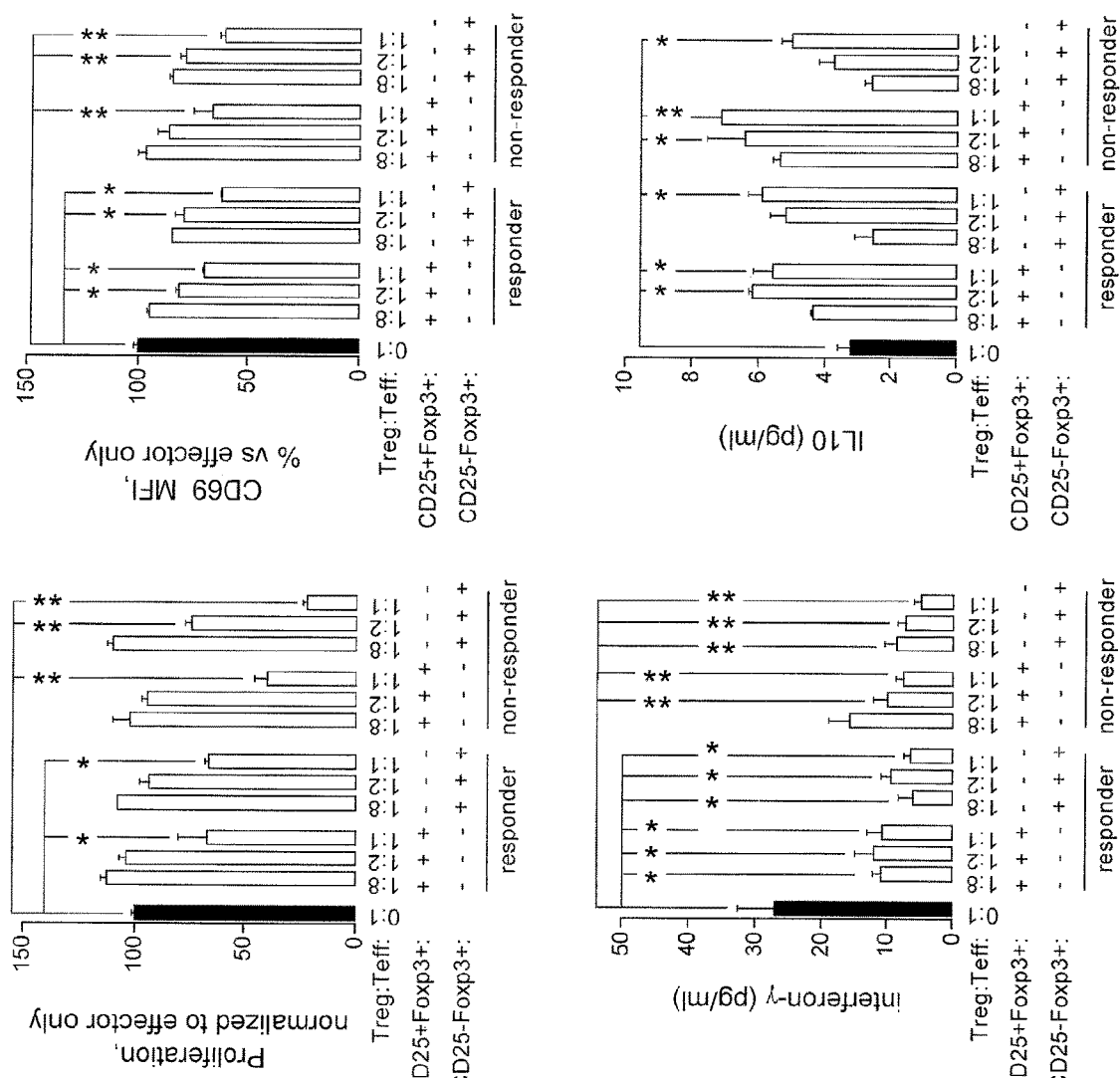
FIG. 4 depicts graphs showing that *L. lactis*-based combination therapy induces suppressive IL10-secreting Foxp3⁺ T cells in responders and non-responders. For in vitro polyclonal suppressor assay, CD4⁺CD25⁻ effector T cells (Teff) were isolated from normoglycemic NOD mice, dye-labeled, and stimulated for 72 hours using soluble anti-CD3 in the presence of accessory cells and increasing ratios of CD4⁺CD25⁺Foxp3⁺ or CD4⁺CD25⁻Foxp3⁺ T cells (Treg), isolated from *L. lactis*-based combination therapy (CT)-treated NOD.Foxp3.hCD2 mice (both responders and non-responders) at the end of the indicated 6-week treatment. Proliferation of Teff cells was measured by flow cytometric analysis of dye dilution and shown as the percentage of Teff cells undergone two or more divisions, normalized to effector only culture. Activation of Teff cells was measured by flow cytometric analysis of CD69 and shown as the MFI, normalized to effector only culture. MSD high-sensitivity multiplex assay of IFN-γ and IL10 concentrations in the Treg:Teff cultures. Statistical significance between groups was calculated using Kruskal-Wallis test followed by Dunnett's multiple testing; * $P<0.05$,  $P<0.01$, *, $P<0.001$; * $P<0.05$, ** $P<0.01$.

Using NOD.Foxp3.hCD2 mice treated by *L. lactis*-based therapy, we could isolate CD4$^+$CD25$^+$Foxp3$^+$ T cells for functional in vitro studies, in which they suppressed proliferation, CD69 activation and IFN-γ production of pathogenic CD4$^+$CD25$^-$ Teff cells. These Tregs produced IL-10 (and TGF-β) when they were co-cultured and stimulated with anti-CD3 antibody in the presence of splenic antigen-presenting cells (APCs) isolated from NOD-scid γc−/− mice (FIG. 4). No difference in regulatory capacity of CD4$^+$CD25$^-$Foxp3$^+$ T cells was seen between therapy responders and non-responders.

Figures 5A, 5B, 5C:
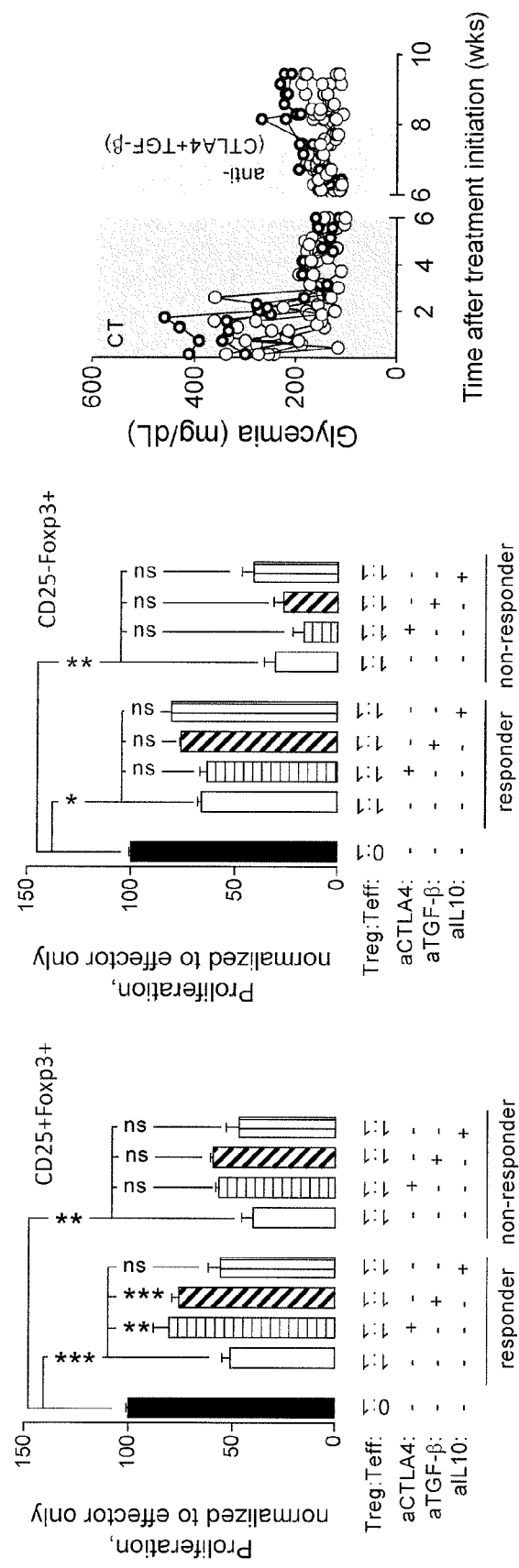
FIG. 5A is a graph showing *L. lactis*-based combination therapy-induced Tregs depend on CTLA4 and TGF-β to control T effector cell responses. T effector (Teff) proliferation—shown as the percentage of Teff cells that had undergone two or more divisions, normalized to proliferation by effector only culture. Dye-labeled CD4⁺CD25⁻ T cells (Teff) were stimulated with anti-CD3 (0.5 µg/ml) in the presence of accessory cells and CD4⁺CD25⁺Foxp3⁺, isolated from *L. lactis*-based combination therapy (CT)-treated NOD.Foxp3.hCD2 mice (both responders and non-responders), and indicated neutralizing antibodies (10 µg/ml). Statistical significance between groups was calculated using Kruskal-Wallis test followed by Dunnett's multiple testing; * $P<0.05$,  $P<0.01$, * $P<0.001$.
FIG. 5B is a graph showing *L. lactis*-based combination therapy-induced Tregs depend on CTLA4 and TGF-β to control T effector cell responses. T effector (Teff) proliferation—shown as the percentage of Teff cells that had undergone 2 or more divisions, normalized to proliferation by effector only culture. Dye-labeled CD4⁺CD25⁻ T cells (Teff) were stimulated with anti-CD3 (0.5 µg/ml) in the presence of accessory cells and CD4⁺CD25⁻Foxp3⁺ cells (Treg), isolated from *L. lactis*-based combination therapy (CT)-treated NOD.Foxp3.hCD2 mice (both responders and non-responders), and indicated neutralizing antibodies (10 µg/ml). Statistical significance between groups was calculated using Kruskal-Wallis test followed by Dunnett's multiple testing; * $P<0.05$,  $P<0.01$, * $P<0.001$.
FIG. 5C is a graph showing that *L. lactis*-based combination therapy-induced Tregs depend on CTLA4 and TGF-β to control T effector cell responses. *L. lactis*-based combination therapy-cured mice were injected with anti-CTLA4 and anti-TGF-β antibodies (n=5) and followed up for diabetes recurrence (glucosuria and blood glucose measurements >200 mg/dl and).

Addition of anti-CTLA4 Ig (clone UC10-4F10) or a TGF-β neutralizing antibody (clone 1D11.16.8) significantly reduced the suppression by the CD4$^+$CD25$^+$Foxp3$^+$ T cells (FIG. 5A), suggesting that CD4$^+$CD25$^+$Foxp3$^+$ Tregs of cured mice inhibit Teff proliferation via a CTLA4- and TGF-β-dependent fashion in vitro. Adding anti-IL10 (clone JES5-2A5) did not alter the direct suppressive effect of the Tregs. On the other hand, these regulatory mechanisms were not demonstrated with the CD4$^+$CD25$^-$Foxp3$^+$ T cell fraction from therapy responders and non-responders (FIG. 5B). Treating stably cured mice in vivo with a combination of anti-CTLA4 Ig (clone UC10-4F10) and anti-TGF-β (clone 1D11.16.8) led to diabetes recurrence in 2 out of 5 mice (FIG. 5C).

Figure 6A:
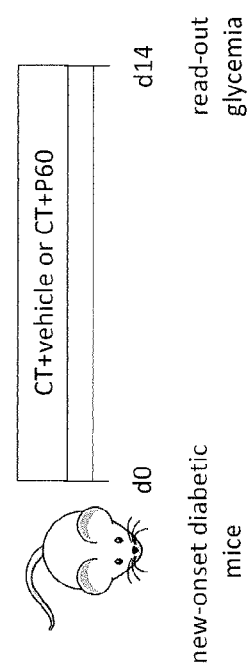
FIG. 6A is a treatment scheme for the simultaneous administration of *L. lactis*-based combination therapy (CT) and the specific FOXP3 inhibitor P60 (i.p. 50 µg/daily) in new-onset diabetic NOD mice.
Figure 6B:
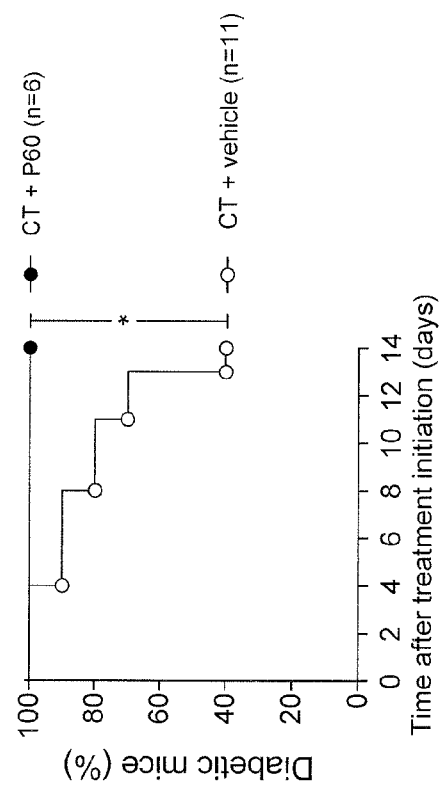
FIG. 6B is a graph showing that specific inhibition of Treg function impairs therapy-induced tolerance. Shown is the percentage of mice that remained diabetic after treatment. In the Kaplan-Meier survival curve, statistical significance between groups was determined by Mantel-Cox log-rank test; * $P<0.05$.

Finally, we investigated whether the therapeutic success of *L. lactis*-based therapy was depended on the presence and functionality of Foxp3$^+$ T cells. For this, new-onset diabetic NOD mice were simultaneously treated with the *L. lactis*-based therapy and the FOXP3-inhibitory peptide P60 for a period of 14 days (FIG. 6A). Interestingly, none of the mice (n=6) developed normoglycemia, while mice treated with the *L. lactis*-based therapy and vehicle (n=11) had a 60% diabetes remission rate, indicating that Tregs are crucial for induction of therapy-induced tolerance (FIG. 6B).

Figure 7A:
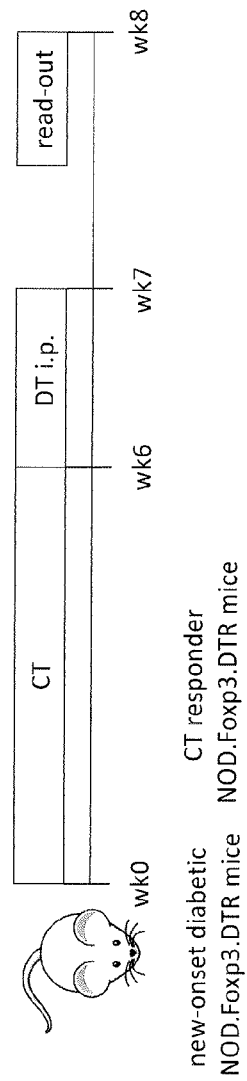
FIG. 7A is a treatment scheme for Foxp3⁺ T cell depletion by diphtheria toxin (DT) in *L. lactis*-based combination therapy (CT)-cured NOD.Foxp3.DTR mice.
Figure 7B:
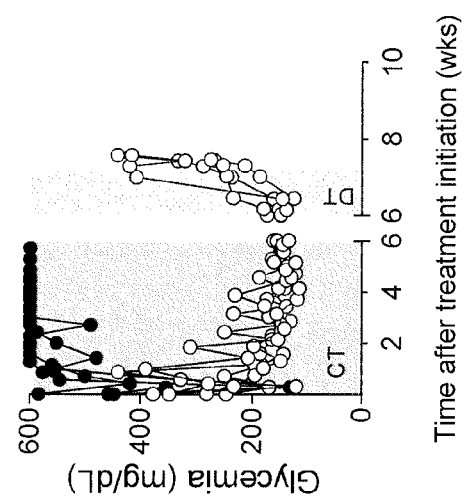
FIG. 7B is a graph showing that Foxp3⁺ T cell depletion breaches *L. lactis*-based combination therapy-induced tolerance in NOD.Foxp3.DTR mice. Blood glucose measurements in new-onset diabetic NOD.Foxp3.DTR mice during *L. lactis*-based combination therapy (n=7) and after DT treatment (n=4). Mice were considered cured (white symbols) when random blood glucose concentrations recovered to beneath 200 mg/dl or non-cured (black symbols) when mice sustained blood glucose concentrations above 200 mg/dl.
Figure 7D:
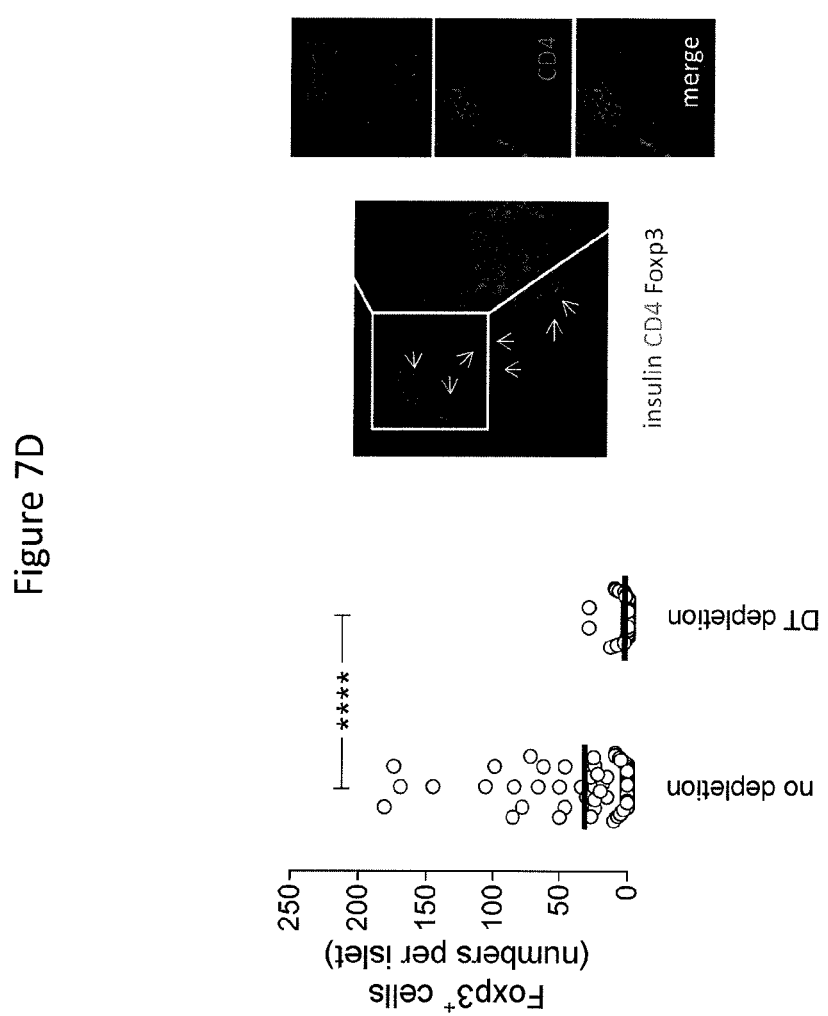
FIG. 7D is a graph showing the quantification of islet-resident Foxp3+ T cells in the pancreas of therapy-cured NOD.Foxp3.DTR mice before and after DT treatment Staining of pancreas sections from combination therapy-tolerized mice for insulin (red), CD4 (purple) and Foxp3 (green) in which the white arrow heads indicate the presence of Foxp3+ T cells within an islet of Langerhans with some insulin positivity. Higher magnification of the boxed area clearly indicates that Foxp3+ cells are CD4+ T-cells. Statistical significance was calculated using Mann-Whitney t-test; ****, P<0.0001.
Figure 10A:
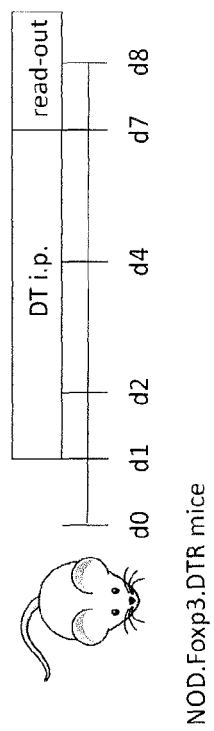
FIG. 10A is schematic scheme to deplete Foxp3+ cells with DT in NOD.Foxp3.DTR mice. Four consecutive i.p. (intraperitoneal) DT injections (on day (d) 1, 2, 5 and 7) (40 µg/kg body weight/d) are indicated in the scheme.
Figure 10B:
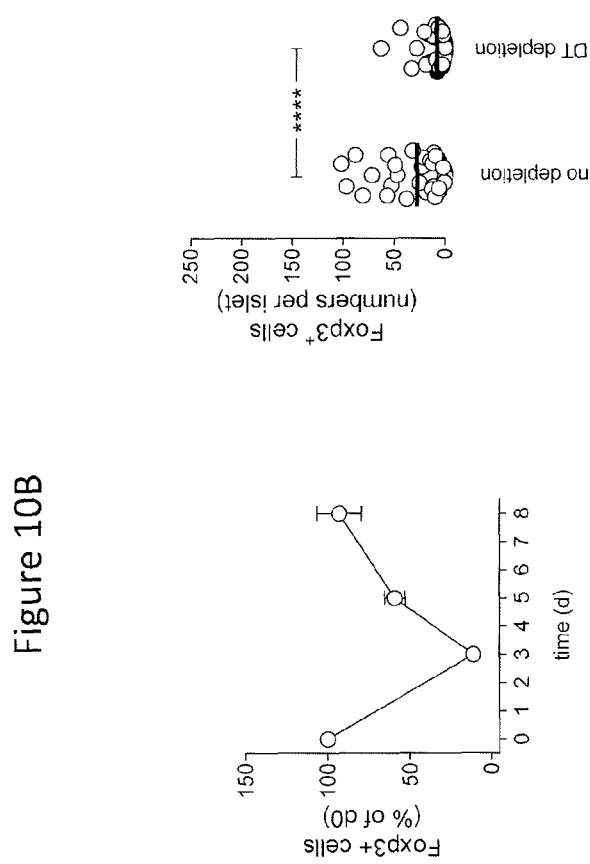
FIG. 10B depicts graphs showing depletion of Foxp3+ cells with DT in NOD.Foxp3.DTR mice. Flow cytometric analysis of peripheral blood demonstrated efficient depletion of Foxp3+ cells in DT-treated NOD.Foxp3.DTR mice. Foxp3 staining of pancreas sections showed effective depletion of islet-resident Foxp3 cells in DT-treated NOD.Foxp3.DTR mice.
Figure 10C:
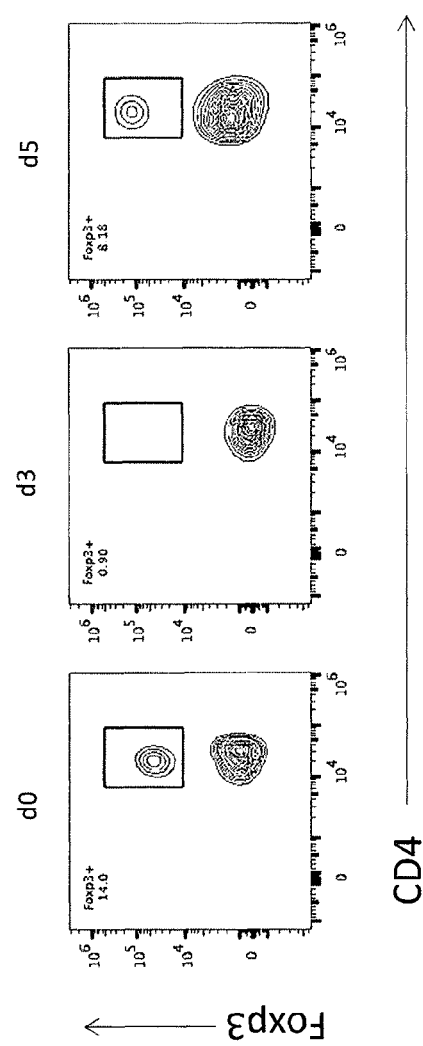
FIG. 10C depicts representative flow cytometric profiles showing the percentage of CD4+ T cells positive for Foxp3 and the DTR-GFP fusion protein before (d0) and after two consecutive DT injections (d3 and 5) of NOD.Foxp3.DTR mice (left panel).
Figure 10D:
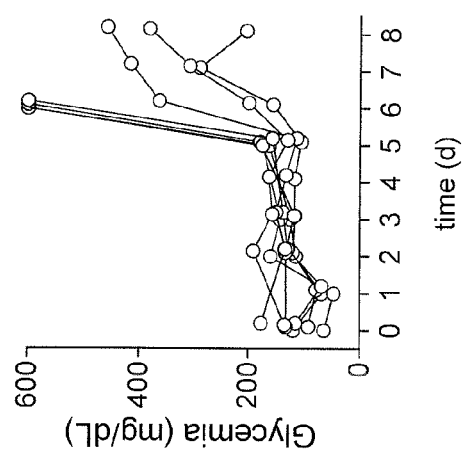
FIG. 10D is a graph demonstrating rapid diabetes onset upon acute Foxp3+ Treg depletion in NOD.Foxp3.DTR mice.

New-onset (spontaneously) diabetic NOD.Foxp3.DTR mice were treated with the *L. lactis*-based therapy and after stable diabetes reversal was observed, Foxp3$^+$ T cells were eliminated using DT as described in the scheme depicted in FIG. 7A. First, we established in unmanipulated NOD.Foxp3.DTR mice that the selected DT regimen eliminated over 90% of CD4$^+$Foxp3$^+$ T cells, with the remaining Tregs expressing low or no CD25, in the peripheral blood within 3 days after first DT injection (FIGS. 10A-C). A progressive repopulation of these cells started from day 5 after first DT injection as has been reported for several Foxp3.DTR strains. See, e.g., Kim J. M. et al., *Nat. Immunol.* 2007, 8:191-197; Suffner J. et al., *J. Immunol.* 2010, 184:1810-1820; and Mayer C. T. et al., *Immun. Inflamm. Dis.* 2014, 2:162-165. This DT regimen also dramatically decreased the amount of Foxp3$^+$ T cells residing in the pancreas, consequently leading to the development of autoimmune diabetes (FIGS. 10B and 10D). Next, comparable to wild-type NOD mice, the *L. lactis*-based treatment induced autoimmune diabetes remission in 57% of NOD.Foxp3.DTR mice (4 out of 7 mice) (FIGS. 7A and 7B). Transient Foxp3$^+$ T cell depletion resulted in a complete reversal to the diabetic state in all mice (n=4) that were initially cured by the therapy, as evidenced by the reappearance of glucosuria along with severe hyperglycemia starting from day 2 after first DT injection (FIG. 7B). This breach of immune tolerance to insulin-producing beta-cells was also accompanied by the induction of severe insulitis (FIG. 7C) and the ablation of the islet-resident Foxp3+ Treg pool (FIG. 7D). Collectively, these data demonstrated that the therapeutic effect from the *L. lactis*-based intervention depended on the presence and functionality of Foxp3+ Tregs.

DISCUSSION

Oral tolerance as a means of intervention to arrest disease has been explored in animal models of autoimmune disease including T1D. See, e.g., Commins SP, *Pediatr. Clin. North. Am.* 2015; 62:1523-1529.

In this example, an oral clinical-grade self-containing *L. lactis* strain secreting chromosomally-integrated human PINS and human IL-10 was prepared. When combined with a short course of sub-therapeutic doses of anti-CD3, the intervention was safe and effective in inducing long-term normoglycemia in new-onset diabetic mice. Initial blood glucose concentrations (<350 mg/dl) in addition to IAA positivity at disease onset were predictors of therapeutic outcome, while preservation of residual beta-cell function and decline in IAA positivity were markers of therapeutic success.

Thus, some degree of residual beta-cell mass will be necessary for therapeutic success when intervening at the moment of diabetes diagnosis, namely when dysglycemia is present.

By dissociating between the immune effects of the *L. lactis*-based intervention in mice responsive or not to the therapy, the nature and role of the immune processes accompanying the treatment was further characterized. The *L. lactis*-based therapy induced suppressive IL-10-secreting CD4+Foxp3+ (both CD25+ and CD25−) T cells in the pancreatic draining lymph nodes and pancreas of responders and even more so of non-responders, suggesting enhanced recruitment of Tregs to the inflamed target tissues. In the periphery, the frequency of CD4+Foxp3+ T cells was also increased in treated mice compared to untreated controls, pointing towards a possible use this cell population as immune marker. Interestingly, the frequency of CTLA4+ T-cells among various Treg subsets was significantly higher in the pancreas of combination therapy-treated responder mice compared to new-onset diabetic mice and in contrast to combination therapy-treated non-responder mice. No difference was seen in the degree of insulitis between responder and non-responder mice, suggesting alterations in lymphocyte subsets other than Tregs.

Peripheral Tregs can use different regulatory mechanisms according to their environmental milieu and stimulatory conditions. See, e.g., Liston A. et al., *Nature Reviews Immunology* 2014; 14:154-165. In these experiments, CTLA4 and TGF-β were important for the regulatory activity of therapy-expanded CD4+CD25+Foxp3+ T cells in vitro and partially in vivo, while IL-10 was not.

Although IL-10 seemed to be a good marker for the identification of our *L. lactis*-based therapy-induced Tregs, others have demonstrated that anti-IL-10 antibodies did not abrogate established tolerance in vivo. See, e.g., Fowler S. and Powrie F, *European Journal of Immunology* 2002, 32:2997-3006.

As in mice, human Tregs are defined by having a suppressive phenotype endowed by high and sustained expression of the transcription factor Foxp3 (see, e.g., Hori S. et al., *Science* 2003; 299:1057-1061) and loss of function/mutation in the Foxp3 gene leads to severe fatal autoimmune disorders (see, e.g., Kim J. M., et al., *Nature Immunology* 2007; 8:191-197; and Mayer C. T. et al., *European Journal of Immunology* 2014, 44:2990-3002).

Specific inhibition of Treg functionality by the P60 peptide (see, e.g., Casares N. et al., *Journal of Immunology* 2010; 185:5150-5159) at the start of *L. lactis*-based therapy impaired the induction of therapy-induced tolerance. Moreover, transient depletion of Foxp3+ Tregs from therapy-tolerized NOD.Foxp3. DTR mice was sufficient to induce complete disease relapse in all animals, demonstrating that the presence of Foxp3+ T cells was important to maintain therapeutic tolerance and control pathogenic Teff cells which were still present in mice responsive to *L. lactis*-based therapy.

The current data demonstrate that combining a clinical-grade self-containing *L. lactis* secreting human PINS and human IL-10 with low-dose anti-CD3 increased the frequency of diabetes reversal compared to anti-CD3 monotherapy. Both therapy responders and non-responders had increased frequencies of CD4+Foxp3+ T cells, suggesting that immune effects induced by the *L. lactis*-based therapy occurred in each individual recipient, but that therapeutic success (defined as return to stable normoglycemia) depended on other parameters, such as functional beta-cell mass still present at disease onset. Therapeutic success was further correlated with starting glycemia. Next to initial blood glucose concentrations at entry, also IAA levels predicted outcome of this *L. lactis*-based therapy using PINS as antigen. The current data demonstrates that Foxp3+ Tregs were essential to induce and maintain active tolerance and control diabetogenic immune responses in tolerized mice. These findings provide tools for testing interventions in humans: a clinical-grade self-containing *L. lactis* secreting islet antigen(s), biomarkers for predicting therapeutic success, and the demonstration that the induction of Foxp3+ T cells is the basis of the *L. lactis*-based therapy.

While some embodiments have been shown and described herein, such embodiments are provided by way of example only. Numerous variations, changes, and substitutions will occur to those skilled in the art without departing from the invention. It should be understood that various alternatives to the embodiments of the invention described herein will be employed in practicing the invention.

EXEMPLARY EMBODIMENTS

1. A lactic acid bacterium (LAB) comprising an exogenous nucleic acid encoding interleukin-10 (IL-10), and an exogenous nucleic acid encoding proinsulin (PINS), wherein said exogenous nucleic acid encoding IL-10 and said exogenous nucleic acid encoding PINS are chromosomally integrated.
2. The LAB of embodiment 1, wherein said LAB is a *Lactococcus* species bacterium.
3. The LAB of embodiment 2, wherein said LAB is *Lactococcus lactis*.
4. The LAB of embodiment 3, wherein said LAB is *Lactococcus lactis* subspecies *cremoris*.
5. The LAB of embodiment 4, wherein said LAB is *Lactococcus lactis* strain MG1363.
6. The LAB of any one of embodiments 1 to 5, wherein said IL-10 is human IL-10 (hIL-10).
7. The LAB of embodiment 6, wherein said hIL-10 when secreted as a mature hIL-10 without a signal peptide comprises alanine (Ala) instead of proline (Pro) at position 2.

8. The LAB of any one of embodiments 1 to 7, wherein said IL-10 has an amino acid sequence at least 95% identical to SEQ ID NO: 1.
9. The LAB of any one of embodiments 1 to 8, wherein said exogenous nucleic acid encoding IL-10 has a nucleotide sequence at least 95% identical to SEQ ID NO: 2.
10. The LAB of any one of the preceding embodiments, wherein said PINS is human PINS (hPINS).
11. The LAB of any one of the preceding embodiments, wherein said PINS has an amino acid sequence at least 95% identical to SEQ ID NO: 3.
12. The LAB of any one of the preceding embodiments, wherein said exogenous nucleic acid encoding PINS has a nucleotide sequence at least 95% identical to SEQ ID NO: 4.
13. The LAB of any one of the preceding embodiments, wherein said LAB constitutively expresses said IL-10.
14. The LAB of embodiment 13, wherein said LAB secretes said IL-10.
15. The LAB of any one of the preceding embodiments, wherein said LAB constitutively expresses said PINS.
16. The LAB of embodiment 15, wherein said LAB secretes said PINS.
17. The LAB of any one of the preceding embodiments, wherein said LAB constitutively expresses and secretes said IL-10 and said PINS.
18. The LAB of any one of the preceding embodiments, wherein said exogenous nucleic acid encoding IL-10 is positioned 3' of an hllA promoter (PhllA).
19. The LAB of embodiment 18, wherein said PhllA is a Lacto coccus lactis PhllA.
20. The LAB of embodiment 18, wherein said exogenous nucleic acid encoding IL-10 is transcriptionally regulated by said PhllA.
21. The LAB of any one of the preceding embodiments, wherein said LAB comprises an expression cassette comprising an hllA promoter, an IL-10 secretion sequence, and said exogenous nucleic acid encoding IL-10.
22. The LAB of embodiment 21, wherein said expression cassette is chromosomally integrated.
23. The LAB of embodiment 22, wherein said expression cassette is chromosomally integrated at a thyA locus.
24. The LAB of any one of embodiments 21 to 23, wherein said IL-10 secretion sequence is a nucleotide sequence encoding a secretion leader of unidentified secreted 45-kDa protein (Usp45) (SSusp45).
25. The LAB of any one of the preceding embodiments, wherein said exogenous nucleic acid encoding PINS is positioned 3' of a gapB promoter.
26. The LAB of embodiment 25, wherein said exogenous nucleic acid encoding PINS is transcriptionally regulated by said gapB promoter.
27. The LAB of embodiment 25 or 26, wherein said LAB comprises a first polycistronic expression cassette comprising a gapB promoter positioned 5' of a gapB gene, a PINS secretion sequence, and said exogenous nucleic acid encoding PINS.
28. The LAB of embodiment 27, wherein said LAB further comprises an intergenic region between said gapB gene and said PINS secretion sequence.
29. The LAB of embodiment 28, wherein said intergenic region is rpmD having SEQ ID NO: 8 or SEQ ID NO: 9.
30. The LAB of any one of embodiments 27 to 29, wherein said gapB promoter and said gapB gene are endogenous to said LAB.
31. The LAB of any one of embodiments 27 to 30, wherein said first polycistronic expression cassette is chromosomally integrated.
32. The LAB of any one of embodiments 27 to 31, wherein said PINS secretion sequence is a nucleotide sequence encoding SSusp45.
33. The LAB of embodiment 32, wherein said SSusp45 has a nucleotide sequence of SEQ ID NO: 11 or SEQ ID NO: 12.
34. The LAB of any one of the preceding embodiments, wherein said LAB further comprises an exogenous nucleic acid encoding a trehalose-6-phosphate phosphatase.
35. The LAB of embodiment 34, wherein said trehalose-6-phosphate phosphatase is *Escherichia coli* OtsB.
36. The LAB of embodiment 34 or 35, wherein said exogenous nucleic acid encoding a trehalose-6-phosphate phosphatase is chromosomally integrated.
37. The LAB of embodiment 36, wherein said exogenous nucleic acid encoding a trehalose-6-phosphate phosphatase is chromosomally integrated 3' of unidentified secreted 45-kDa protein gene (usp45).
38. The LAB of embodiment 37, wherein said LAB comprises a second polycistronic expression cassette comprising a usp45 promoter, said usp45, and said exogenous nucleic acid encoding a trehalose-6-phosphate phosphatase.
39. The LAB of embodiment 38, wherein said second polycistronic expression cassette further comprises an intergenic region between said usp45 and said exogenous nucleic acid encoding a trehalose-6-phosphate phosphatase.
40. The LAB of embodiment 39, wherein said intergenic region is rpmD having SEQ ID NO: 8 or SEQ ID NO: 9.
41. The LAB of any one of the preceding embodiments, wherein a trehalose-6-phosphate phosphorylase gene (trePP) is disrupted or inactivated in said LAB.
42. The LAB of embodiment 41, wherein said trePP is inactivated by removing said trePP or a fragment thereof.
43. The LAB of embodiment 41, wherein said trePP is disrupted by insertion of a stop codon.
44. The LAB of any one of embodiments 41-43, wherein said LAB lacks trePP activity.
45. The LAB of any one of the preceding embodiments, wherein a cellobiose-specific PTS system IIC component gene (ptcC) is disrupted or inactivated in said LAB.
46. The LAB of embodiment 45, wherein said ptcC is disrupted by inserting a stop codon.
47. The LAB of embodiment 45, wherein said ptcC is inactivated by removing said ptcC or a fragment thereof.
48. The LAB of any one of embodiments 45 to 47, wherein said LAB lacks ptcC activity.
49. The LAB of any of the preceding embodiments, wherein said LAB further comprises one or more genes encoding one or more trehalose transporter(s).
50. The LAB of embodiment 49, wherein said one or more genes encoding one or more trehalose transporter(s) is endogenous to said LAB.
51. The LAB of embodiment 49 or 50, wherein said LAB overexpresses said one or more trehalose transporter(s).
52. The LAB according to any one of embodiments 49 to 51, wherein said one or more genes encoding one or more trehalose transporter(s) is/are positioned 3' of an hllA promoter (PhllA).
53. The LAB of embodiment 52, wherein said one or more genes encoding one or more trehalose transporter(s) is/are transcriptionally regulated by said PhllA.

54. The LAB of any one of embodiments 47 to 51, wherein said one or more genes encoding one or more trehalose transporter(s) is/are selected from the group consisting of llmg_0453, llmg_0454, and any combination thereof.
55. The LAB of embodiment 54, wherein said one or more genes encoding one or more trehalose transporter(s) comprises two genes encoding two trehalose transporters, wherein an intergenic region is located between said two genes.
56. The LAB of embodiment 55, wherein said intergenic region is rpmD having SEQ ID NO: 8 or SEQ ID NO: 9.
57. A composition comprising the LAB of any one of the preceding embodiments.
58. A pharmaceutical composition comprising the LAB of any one of embodiments 1 to 56, and a pharmaceutically acceptable carrier.
59. The LAB of any one of embodiments 1 to 56, the composition of embodiment 57, or the pharmaceutical composition of embodiment 58, for use in the treatment of type-1 diabetes (T1D).
60. The LAB of any one of embodiments 1 to 56, the composition of embodiment 57, or the pharmaceutical composition of embodiment 58, for use in the preparation of a medicament for the treatment of T1D.
61. The LAB, the composition, or the pharmaceutical composition of embodiment 60, wherein said T1D is recent-onset T1D.
62. A method for the treatment of T1D in a subject in need thereof comprising administering to said subject a therapeutically effective amount of the LAB of any one of embodiments 1 to 56, the composition of embodiment 57, or the pharmaceutical composition of embodiment 58.
63. The method of embodiment 62, wherein said T1D is recent-onset T1D.
64. The method of embodiment 62 or 63, wherein said subject is a human.
65. The method of any one of embodiments 62 to 64, wherein said method further comprises administering a therapeutically effective amount of an anti-CD3 antibody to said subject.
66. The method of embodiment 65, wherein said anti-CD3 antibody is a monoclonal antibody.
67. The method of embodiment 65 or 66, wherein said anti-CD3 antibody is otelixizumab or teplizumab.
68. The method of any one of embodiments 65 to 67, wherein said antibody is administered to said subject using a co-therapeutic regimen.
69. The method of any one of embodiments 65 to 68, wherein said administering said LAB and said administering said anti-CD3 antibody:
 (i) reduces an amount of insulin the subject needs to maintain a normal blood glucose level, when compared to a corresponding subject treated with anti-CD3 antibody alone, or compared to a corresponding subject not being administered said LAB and said anti-CD3 antibody;
 (ii) preserves initial beta-cell function in said subject for at least about 2 months as measured by C-peptide level;
 (iii) maintains normal glycemia in the subject for at least about 2 months;
 (iv) maintains a normal hemoglobinA1c (HbA1c) level in said subject for at least about 2 months; or
 (v) any combination thereof.
70. The method of any one of embodiments 62 to 69, wherein the method further comprises measuring insulin autoantibody (IAA) in said subject.
71. A method for preparing a genetically modified LAB comprising (i) contacting an LAB with an exogenous nucleic acid encoding IL-10; and (ii) contacting said LAB with an exogenous nucleic acid encoding PINS, wherein said exogenous nucleic acid encoding IL-10, and said exogenous nucleic acid encoding PINS are chromosomally integrated.
72. The method of embodiment 71, wherein said exogenous nucleic acid encoding IL-10 and said exogenous nucleic acid encoding PINS are chromosomally integrated using homologous recombination.
73. The method of embodiment 71 or 72, wherein said contacting said LAB with an exogenous nucleic acid encoding IL-10 occurs prior to said contacting said LAB with an exogenous nucleic acid encoding PINS.
74. The method of embodiment 71 or 72, wherein said contacting said LAB with an exogenous nucleic acid encoding IL-10 occurs subsequent to said contacting said LAB with an exogenous nucleic acid encoding PINS.
75. The method of any one of embodiments 71 to 74, further comprising combining a culture of said genetically modified LAB with at least one stabilizing agent to form a bacterial mixture.
76. The method of embodiment 75, further comprising removing water from said bacterial mixture forming a dried composition.
77. The method of embodiment 76, comprising freeze-drying said bacterial mixture to form a freeze-dried composition.
78. The method of embodiment 77, wherein said at least one stabilizing agent comprises at least one cryopreserving agent.
79. The method of any one of embodiments 71 to 78, further comprising combining said genetically modified LAB, said dried composition, or said freeze-dried composition with a pharmaceutically acceptable carrier to form a pharmaceutical composition.
80. The method of any one of embodiments 76 to 79, further comprising formulating said dry composition, said freeze-dried composition or said pharmaceutical composition into a pharmaceutical dosage form.
81. A genetically modified bacterium prepared by the method of any one of embodiments 71 to 80.
82. A method for preparing a pharmaceutical composition comprising contacting a culture of the LAB of any one of embodiments 1 to 56 with at least one stabilizing agent forming a bacterial mixture.
83. The method of embodiment 82, further comprising removing water from said bacterial mixture, thereby forming a dried composition.
84. The method of embodiment 82 or 83, comprising freeze-drying said bacterial mixture thereby forming a freeze-dried composition.
85. The method of any one of embodiments 82 to 84, wherein said at least one stabilizing agent comprises at least one cryopreserving agent.
86. The method of embodiment 84 or 85, further comprising contacting said freeze-dried composition with a pharmaceutically acceptable carrier forming a pharmaceutical composition.
87. The method of any one of embodiments 84 to 86, further comprising formulating said freeze-dried composition into a pharmaceutical dosage form.
88. The method of embodiment 87, wherein said pharmaceutical dosage form is selected from the group consisting of a tablet, a capsule, a granule, and a sachet.

89. A unit dosage form comprising the LAB of any one of embodiments 1 to 56, the composition of embodiment 57, or the pharmaceutical composition of embodiment 58.
90. The unit dosage form of embodiment 89, wherein said unit dosage form is an oral dosage form.
91. The unit dosage form of embodiment 90, wherein said oral dosage form is selected from the group consisting of a tablet, a capsule, a granule, and a sachet.
92. The unit dosage form of any one of embodiments 89 to 91, wherein said unit dosage form comprises from about $1\times10^6$ to about $1\times10^{12}$ colony forming units (cfu) of said LAB.
93. The unit dosage form of embodiment 92 comprising from about $1\times10^8$ to about $1\times10^{11}$ cfu.
94. A kit comprising (1) an LAB according to any one of embodiments 1 to 56, a composition according to embodiment 57, a pharmaceutical composition of embodiment 58, or a unit dosage form of any one of embodiments 89 to 93, and (2) instructions for administering said LAB, said composition, said pharmaceutical composition, or said unit dosage form to a mammal.
95. The kit of embodiment 94, wherein said mammal is a human.
96. A bacterial suspension comprising the LAB of any one of embodiments 1 to 56, a solvent, and a stabilizing agent.
97. The bacterial suspension of embodiment 96, wherein said solvent is selected from water, oil, and any combination thereof.

SEQUENCE LISTING

```
<160> NUMBER OF SEQ ID NOS: 25

<210> SEQ ID NO 1
<211> LENGTH: 160
<212> TYPE: PRT
<213> ORGANISM: Homo sapiens
<220> FEATURE:
<221> NAME/KEY: MISC
<222> LOCATION: (1)..(160)
<223> OTHER INFORMATION: human IL-10 sequence without signal peptide

<400> SEQUENCE: 1

Ser Ala Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 480
<212> TYPE: DNA
<213> ORGANISM: Homo sapiens
<220> FEATURE:
<221> NAME/KEY: MISC
<222> LOCATION: (1)..(480)
<223> OTHER INFORMATION: human IL-10 coding sequence without signal
      peptide

<400> SEQUENCE: 2
tcagctggtc aaggtactca atcagaaaac tcatgtactc actttccagg taacttgcca      60
aacatgcttc gtgatttgcg tgatgctttt tcacgtgtta aaactttttt tcaaatgaaa     120
```

```
gatcaacttg ataacttgct tttgaaagaa tcacttttgg aagattttaa aggttacctt        180
ggttgtcaag ctttgtcaga aatgatccaa tttaccttg aagaagttat gccacaagct        240
gaaaaccaag atccagatat caaagctcac gttaactcat gggtgaaaa ccttaaaact        300 ttgcgtcttc gtttgcgtcg ttgtcaccgt tttcttccat gtgaaaacaa atcaaaagct        360
gttgaacaag ttaaaaacgc ttttaacaaa ttgcaagaaa aaggtatcta caaagctatg        420
tcagaatttg atatctttat caactacatc gaagcttaca tgactatgaa aatccgtaac        480
```

<210> SEQ ID NO 3
<211> LENGTH: 86
<212> TYPE: PRT
<213> ORGANISM: Homo sapiens
<220> FEATURE:
<221> NAME/KEY: MISC
<222> LOCATION: (1)..(86)
<223> OTHER INFORMATION: human proinsulin (PINS) without signal peptide

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 4
<211> LENGTH: 258
<212> TYPE: DNA
<213> ORGANISM: Homo sapiens
<220> FEATURE:
<221> NAME/KEY: MISC
<222> LOCATION: (1)..(258)
<223> OTHER INFORMATION: human proinsulin (PINS) coding sequence without
      signal peptide

<400> SEQUENCE: 4

```
tttgtgaacc aacacctgtg cggctcacac ctggtggaag ctctctacct agtgtgcggg        60
gaacgaggct tcttctacac acccaagacc cgccggagg cagaggacct gcaggtgggg        120
caggtggagc tgggcggggg ccctggtgca ggcagcctgc agcccttggc cctggagggg        180
tccctgcaga agcgtggcat tgtgaacaa tgctgtacca gcatctgctc cctctaccag        240
ctggagaact actgcaac                                                     258
```

<210> SEQ ID NO 5
<211> LENGTH: 110
<212> TYPE: PRT
<213> ORGANISM: Homo sapiens
<220> FEATURE:
<221> NAME/KEY: MISC
<222> LOCATION: (1)..(110)
<223> OTHER INFORMATION: wild-type human proinsulin (PINS) sequence

<400> SEQUENCE: 5

Met Ala Leu Trp Met Arg Leu Leu Pro Leu Leu Ala Leu Leu Ala Leu
1               5                   10                  15

```
Trp Gly Pro Asp Pro Ala Ala Ala Phe Val Asn Gln His Leu Cys Gly
         20                  25                  30

Ser His Leu Val Glu Ala Leu Tyr Leu Val Cys Gly Glu Arg Gly Phe
             35                  40                  45

Phe Tyr Thr Pro Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110

<210> SEQ ID NO 6
<211> LENGTH: 333
<212> TYPE: DNA
<213> ORGANISM: Homo sapiens
<220> FEATURE:
<221> NAME/KEY: MISC
<222> LOCATION: (1)..(333)
<223> OTHER INFORMATION: wild-type human PINS open reading frame

<400> SEQUENCE: 6
atggccctgt ggatgcgcct cctgcccctg ctggcgctgc tggccctctg gggacctgac      60
ccagccgcag cctttgtgaa ccaacacctg tgcggctcac acctggtgga agctctctac     120
ctagtgtgcg gggaacgagg cttcttctac acacccaaga cccgccggga ggcagaggac     180
ctgcaggtgg ggcaggtgga gctgggcggg ggccctggtg caggcagcct gcagcccttg     240
gccctggagg ggtccctgca gaagcgtggc attgtggaac aatgctgtac cagcatctgc     300
tccctctacc agctggagaa ctactgcaac tag                                  333

<210> SEQ ID NO 7
<211> LENGTH: 300
<212> TYPE: DNA
<213> ORGANISM: Homo sapiens
<220> FEATURE:
<221> NAME/KEY: MISC
<222> LOCATION: (1)..(300)
<223> OTHER INFORMATION: human PINS splice variant; AY899304; coding
      sequence is nt 56-388

<400> SEQUENCE: 7
gccatcaagc aggtctgttc caagggcctt tgcgtcagat cactgtcctt ctgccatggc      60
cctgtggatg cgcctcctgc ccctgctggc gctgctggcc ctctggggac ctgacccagc     120
cgcagccttt gtgaaccaac acctgtgcgg ctcacacctg gtggaagctc tctacctagt     180
gtgcggggaa cgaggcttct tctacacacc caagacccgc cgggaggcag aggacctgca     240
ggtggggcag gtggagctgg gcgggggccc tggtgcaggc agcctgcagc ccttggccct     300

<210> SEQ ID NO 8
<211> LENGTH: 16
<212> TYPE: DNA
<213> ORGANISM: Homo sapiens
<220> FEATURE:
<221> NAME/KEY: MISC
<222> LOCATION: (1)..(16)
<223> OTHER INFORMATION: 5' intergenic region of rpmD gene; nt 1-3 is
      the stop codon of preceding gene and nt 14-16 is the ATG of the
      subsequent gene

<400> SEQUENCE: 8
```
taaggaggaa aaaatg					16

<210> SEQ ID NO 9
<211> LENGTH: 10
<212> TYPE: DNA
<213> ORGANISM: Homo sapiens
<220> FEATURE:
<221> NAME/KEY: MISC
<222> LOCATION: (1)..(10)
<223> OTHER INFORMATION: 5' intergenic region rpmD gene without stop and
      start codons

<400> SEQUENCE: 9 ggaggaaaaa					10

<210> SEQ ID NO 10
<211> LENGTH: 27
<212> TYPE: PRT
<213> ORGANISM: Lactococcus lactis
<220> FEATURE:
<221> NAME/KEY: MISC
<222> LOCATION: (1)..(27)
<223> OTHER INFORMATION: Secretion leader SSusp45

<400> SEQUENCE: 10

Met Lys Lys Lys Ile Ile Ser Ala Ile Leu Met Ser Thr Val Ile Leu
1               5                   10                  15

Ser Ala Ala Ala Pro Leu Ser Gly Val Tyr Ala
            20                  25

<210> SEQ ID NO 11
<211> LENGTH: 81
<212> TYPE: DNA
<213> ORGANISM: Artificial Sequence
<220> FEATURE:
<223> OTHER INFORMATION: Chemically synthesized
<220> FEATURE:
<221> NAME/KEY: MISC
<222> LOCATION: (1)..(81)
<223> OTHER INFORMATION: Encodes SSusp45 secretion leader sequence

<400> SEQUENCE: 11
atgaaaaaaa agattatctc agctatttta atgtctacag tgatactttc tgctgcagcc		60 ccgttgtcag gtgtttacgc c							81

<210> SEQ ID NO 12
<211> LENGTH: 81
<212> TYPE: DNA
<213> ORGANISM: Artificial Sequence
<220> FEATURE:
<223> OTHER INFORMATION: Chemically synthesized
<220> FEATURE:
<221> NAME/KEY: MISC
<222> LOCATION: (1)..(81)
<223> OTHER INFORMATION: Encodes SSusp45 secretion leader sequence

<400> SEQUENCE: 12
atgaagaaga aaatcattag tgccatctta atgtctacag tgattctttc agctgcagct		60 cctttatcag gcgtttatgc a							81

<210> SEQ ID NO 13
<211> LENGTH: 720
<212> TYPE: DNA
<213> ORGANISM: Artificial Sequence
<220> FEATURE:
<223> OTHER INFORMATION: genetically engineered construct

```
<220> FEATURE:
<221> NAME/KEY: MISC
<222> LOCATION: (1)..(720)
<223> OTHER INFORMATION: IL-10 expression cassette
<220> FEATURE:
<221> NAME/KEY: CDS
<222> LOCATION: (105)..(665)
<223> OTHER INFORMATION: nt 105-185 encodes SSusp45 secretion leader; nt
      185-665 encodes hIL10aPxA; stop codon is nt 666-668

<400> SEQUENCE: 13
aaaacgcctt aaaatggcat tttgacttgc aaactgggct aagatttgct aaaatgaaaa      60
atgcctatgt ttaaggtaaa aaacaaatgg aggacatttc taaa atg aaa aaa aag     116
                                                  Met Lys Lys Lys
                                                    1 att atc tca gct att tta atg tct aca gtg ata ctt tct gct gca gcc     164
Ile Ile Ser Ala Ile Leu Met Ser Thr Val Ile Leu Ser Ala Ala Ala
 5              10                  15                  20 ccg ttg tca ggt gtt tac gcc tca gct ggt caa ggt act caa tca gaa     212
Pro Leu Ser Gly Val Tyr Ala Ser Ala Gly Gln Gly Thr Gln Ser Glu
             25                  30                  35 aac tca tgt act cac ttt cca ggt aac ttg cca aac atg ctt cgt gat     260
Asn Ser Cys Thr His Phe Pro Gly Asn Leu Pro Asn Met Leu Arg Asp
         40                  45                  50 ttg cgt gat gct ttt tca cgt gtt aaa act ttt ttt caa atg aaa gat     308
Leu Arg Asp Ala Phe Ser Arg Val Lys Thr Phe Phe Gln Met Lys Asp
     55                  60                  65 caa ctt gat aac ttg ctt ttg aaa gaa tca ctt ttg gaa gat ttt aaa     356
Gln Leu Asp Asn Leu Leu Leu Lys Glu Ser Leu Leu Glu Asp Phe Lys
 70                  75                  80 ggt tac ctt ggt tgt caa gct ttg tca gaa atg atc caa ttt tac ctt     404
Gly Tyr Leu Gly Cys Gln Ala Leu Ser Glu Met Ile Gln Phe Tyr Leu
 85              90                  95                 100 gaa gaa gtt atg cca caa gct gaa aac caa gat cca gat atc aaa gct     452
Glu Glu Val Met Pro Gln Ala Glu Asn Gln Asp Pro Asp Ile Lys Ala
            105                 110                 115 cac gtt aac tca ttg ggt gaa aac ctt aaa act ttg cgt ctt cgt ttg     500
His Val Asn Ser Leu Gly Glu Asn Leu Lys Thr Leu Arg Leu Arg Leu
        120                 125                 130 cgt cgt tgt cac cgt ttt ctt cca tgt gaa aac aaa tca aaa gct gtt     548
Arg Arg Cys His Arg Phe Leu Pro Cys Glu Asn Lys Ser Lys Ala Val
    135                 140                 145 gaa caa gtt aaa aac gct ttt aac aaa ttg caa gaa aaa ggt atc tac     596
Glu Gln Val Lys Asn Ala Phe Asn Lys Leu Gln Glu Lys Gly Ile Tyr
150                 155                 160 aaa gct atg tca gaa ttt gat atc ttt atc aac tac atc gaa gct tac     644
Lys Ala Met Ser Glu Phe Asp Ile Phe Ile Asn Tyr Ile Glu Ala Tyr
165                 170                 175                 180 atg act atg aaa atc cgt aac taactagaat taatctataa gttactgaca       695
Met Thr Met Lys Ile Arg Asn
                185 aaactgtcag taacttttttt tgtgg                                         720

<210> SEQ ID NO 14
<211> LENGTH: 187
<212> TYPE: PRT
<213> ORGANISM: Artificial Sequence
<220> FEATURE:
<223> OTHER INFORMATION: Synthetic Construct

<400> SEQUENCE: 14

Met Lys Lys Lys Ile Ile Ser Ala Ile Leu Met Ser Thr Val Ile Leu
```

```
              1               5                   10                  15
            Ser Ala Ala Pro Leu Ser Gly Val Tyr Ala Ser Ala Gly Gln Gly
                            20                  25                  30

Thr Gln Ser Glu Asn Ser Cys Thr His Phe Pro Gly Asn Leu Pro Asn
                            35                  40                  45

Met Leu Arg Asp Leu Arg Asp Ala Phe Ser Arg Val Lys Thr Phe Phe
                 50                  55                  60

Gln Met Lys Asp Gln Leu Asp Asn Leu Leu Lys Glu Ser Leu Leu
            65                  70                  75                  80

Glu Asp Phe Lys Gly Tyr Leu Gly Cys Gln Ala Leu Ser Glu Met Ile
                                85                  90                  95

Gln Phe Tyr Leu Glu Glu Val Met Pro Gln Ala Glu Asn Gln Asp Pro
                            100                 105                 110

Asp Ile Lys Ala His Val Asn Ser Leu Gly Glu Asn Leu Lys Thr Leu
                        115                 120                 125

Arg Leu Arg Leu Arg Arg Cys His Arg Phe Leu Pro Cys Glu Asn Lys
                    130                 135                 140

Ser Lys Ala Val Glu Gln Val Lys Asn Ala Phe Asn Lys Leu Gln Glu
            145                 150                 155                 160

Lys Gly Ile Tyr Lys Ala Met Ser Glu Phe Asp Ile Phe Ile Asn Tyr
                            165                 170                 175

Ile Glu Ala Tyr Met Thr Met Lys Ile Arg Asn
                        180                 185
```

<210> SEQ ID NO 15
<211> LENGTH: 1680
<212> TYPE: DNA
<213> ORGANISM: Artificial Sequence
<220> FEATURE:
<223> OTHER INFORMATION: genetically engineered construct
<220> FEATURE:
<221> NAME/KEY: MISC
<222> LOCATION: (1)..(1680)
<223> OTHER INFORMATION: PINS polycistronic expression cassette
<220> FEATURE:
<221> NAME/KEY: CDS
<222> LOCATION: (277)..(1284)
<223> OTHER INFORMATION: gapB gene coding sequence
<220> FEATURE:
<221> NAME/KEY: misc_feature
<222> LOCATION: (1285)..(1300)
<223> OTHER INFORMATION: intergenic region (rpmD); 1285-1287 is stop
      codon of preceding coding sequence and 1298-1300 is the ATG of the
      subsequent coding sequence
<220> FEATURE:
<221> NAME/KEY: CDS
<222> LOCATION: (1298)..(1636)
<223> OTHER INFORMATION: Secretion sequence SSusp45 encoded by nt.
      1298-1378; Human PINS encoded by 1379-1636

<400> SEQUENCE: 15

```
aataaaaatt actgacagcc tgctcagtaa ttttttagt cataattttt aggtggaaag      60
tcaaagatta ttgccaaaag tattagcttt tttaatgtta accgctttca gaagaagggg    120
agttcatttg cttttgtaga gcgctttcta aggtagttta tgtttgcaaa ttttaaaaaa    180
agtgttaaaa taaagagta agttaaattg ttaacttagt caatttaaaa ggtttgcctt     240
ttataaaatc taatccctat aaggaggaaa ctacta atg gta gtt aaa gtt ggt      294
                                          Met Val Val Lys Val Gly
                                           1               5 att aac ggt ttc ggt cgt atc ggt cgt ctt gct ttc cgt cgt att caa     342
Ile Asn Gly Phe Gly Arg Ile Gly Arg Leu Ala Phe Arg Arg Ile Gln
            10                  15                  20
```

```
aat gtt gaa ggt gtt gaa gtt gtt gca atc aac gac ttg aca gat cca      390
Asn Val Glu Gly Val Glu Val Val Ala Ile Asn Asp Leu Thr Asp Pro
            25                  30                  35 gca atg ctt gct cac ttg ctt aaa tac gat aca act caa ggt cgt ttt      438
Ala Met Leu Ala His Leu Leu Lys Tyr Asp Thr Thr Gln Gly Arg Phe
        40                  45                  50 gat ggt aaa gtt gaa gtt aaa gat ggt ggt ttt gaa gtt aac ggt aaa      486
Asp Gly Lys Val Glu Val Lys Asp Gly Gly Phe Glu Val Asn Gly Lys
55                  60                  65                  70 ttc gtt aaa gtt act gct gaa tct aac cca gct aac atc aac tgg gct      534
Phe Val Lys Val Thr Ala Glu Ser Asn Pro Ala Asn Ile Asn Trp Ala
                75                  80                  85 gaa gtt ggt gca gaa atc gtt ctt gaa gca act ggt ttc ttc gca act      582
Glu Val Gly Ala Glu Ile Val Leu Glu Ala Thr Gly Phe Phe Ala Thr
            90                  95                 100 aaa gaa aaa gct gaa caa cac ttg cac gct aat ggt gct aag aaa gtt      630
Lys Glu Lys Ala Glu Gln His Leu His Ala Asn Gly Ala Lys Lys Val
        105                 110                 115 gtt atc act gca cct ggt gga tca gat gtt aaa aca atc gtt ttc aac      678
Val Ile Thr Ala Pro Gly Gly Ser Asp Val Lys Thr Ile Val Phe Asn
120                 125                 130 act aac cac gaa gta ctt gat gga act gaa aca gta att tca gct ggt      726
Thr Asn His Glu Val Leu Asp Gly Thr Glu Thr Val Ile Ser Ala Gly
135                 140                 145                 150 tca tgt aca acc aac tgt ctt gct cca atg gct gat act ttg aac aaa      774
Ser Cys Thr Thr Asn Cys Leu Ala Pro Met Ala Asp Thr Leu Asn Lys
                155                 160                 165 caa ttc ggt atc aaa gtt ggt aca atg act aca gtt cac ggt tac act      822
Gln Phe Gly Ile Lys Val Gly Thr Met Thr Thr Val His Gly Tyr Thr
            170                 175                 180 ggt gac caa atg act ctt gat ggc cca cac cgt ggt gga gat ttc cgt      870
Gly Asp Gln Met Thr Leu Asp Gly Pro His Arg Gly Gly Asp Phe Arg
        185                 190                 195 cgc gca cgt gct gca gct gaa aac atc gta cct aac tca aca ggt gct      918
Arg Ala Arg Ala Ala Ala Glu Asn Ile Val Pro Asn Ser Thr Gly Ala
200                 205                 210 gct aaa gcc atc ggt ctt gta ttg cca gaa ctt caa ggt aaa ctt caa      966
Ala Lys Ala Ile Gly Leu Val Leu Pro Glu Leu Gln Gly Lys Leu Gln
215                 220                 225                 230 gga cat gct caa cgt gta cca gtt cca act ggt tca ttg act gaa ctt     1014
Gly His Ala Gln Arg Val Pro Val Pro Thr Gly Ser Leu Thr Glu Leu
                235                 240                 245 gtt act atc ctt gat aaa gaa gtt aca gtt gac gaa atc aac gca gct     1062
Val Thr Ile Leu Asp Lys Glu Val Thr Val Asp Glu Ile Asn Ala Ala
            250                 255                 260 atg aaa gct gct tca aat gaa tca ttt ggt tac aac gaa gac caa atc     1110
Met Lys Ala Ala Ser Asn Glu Ser Phe Gly Tyr Asn Glu Asp Gln Ile
        265                 270                 275 gtt tca tct gat atc gtt ggt atc tca aac tct tca ctc ttt gat gct     1158
Val Ser Ser Asp Ile Val Gly Ile Ser Asn Ser Ser Leu Phe Asp Ala
280                 285                 290 act caa act gaa gtt act tca gct aac gga gct caa ctt gtt aaa act     1206
Thr Gln Thr Glu Val Thr Ser Ala Asn Gly Ala Gln Leu Val Lys Thr
295                 300                 305                 310 gta tct tgg tac gat aac gaa atg tca tac act tca aac ctt gtt cgt     1254
Val Ser Trp Tyr Asp Asn Glu Met Ser Tyr Thr Ser Asn Leu Val Arg
                315                 320                 325 aca ctt gca tac ttc gct aaa atc gct aaa taaggaggaa aaa atg aag     1303
Thr Leu Ala Tyr Phe Ala Lys Ile Ala Lys                Met Lys
```

```
aag aaa atc att agt gcc atc tta atg tct aca gtg att ctt tca gct    1351
Lys Lys Ile Ile Ser Ala Ile Leu Met Ser Thr Val Ile Leu Ser Ala
        340                 345                 350 gca gct cct tta tca ggc gtt tat gca ttt gtg aac caa cac ctg tgc    1399
Ala Ala Pro Leu Ser Gly Val Tyr Ala Phe Val Asn Gln His Leu Cys
355                 360                 365                 370 ggc tca cac ctg gtg gaa gct ctc tac cta gtg tgc ggg gaa cga ggc    1447
Gly Ser His Leu Val Glu Ala Leu Tyr Leu Val Cys Gly Glu Arg Gly
                375                 380                 385 ttc ttc tac aca ccc aag acc cgc cgg gag gca gag gac ctg cag gtg    1495
Phe Phe Tyr Thr Pro Lys Thr Arg Arg Glu Ala Glu Asp Leu Gln Val
            390                 395                 400 ggg cag gtg gag ctg ggc ggg ggc cct ggt gca ggc agc ctg cag ccc    1543
Gly Gln Val Glu Leu Gly Gly Gly Pro Gly Ala Gly Ser Leu Gln Pro
        405                 410                 415 ttg gcc ctg gag ggg tcc ctg cag aag cgt ggc att gtg gaa caa tgc    1591
Leu Ala Leu Glu Gly Ser Leu Gln Lys Arg Gly Ile Val Glu Gln Cys
420                 425                 430 tgt acc agc atc tgc tcc ctc tac cag ctg gag aac tac tgc aac        1636
Cys Thr Ser Ile Cys Ser Leu Tyr Gln Leu Glu Asn Tyr Cys Asn
435                 440                 445 taatttccg attttaacgg tataaaaacc agtcttcggg ctgg                    1680
```

<210> SEQ ID NO 16
<211> LENGTH: 336
<212> TYPE: PRT
<213> ORGANISM: Artificial Sequence
<220> FEATURE:
<223> OTHER INFORMATION: Synthetic Construct

<400> SEQUENCE: 16

```
Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Val Ala Ile
            20                  25                  30

Asn Asp Leu Thr Asp Pro Ala Met Leu Ala His Leu Leu Lys Tyr Asp
        35                  40                  45

Thr Thr Gln Gly Arg Phe Asp Gly Lys Val Glu Val Lys Asp Gly Gly
    50                  55                  60

Phe Glu Val Asn Gly Lys Phe Val Lys Val Thr Ala Glu Ser Asn Pro
65                  70                  75                  80

Ala Asn Ile Asn Trp Ala Glu Val Gly Ala Glu Ile Val Leu Glu Ala
                85                  90                  95

Thr Gly Phe Phe Ala Thr Lys Glu Lys Ala Glu Gln His Leu His Ala
            100                 105                 110

Asn Gly Ala Lys Lys Val Val Ile Thr Ala Pro Gly Gly Ser Asp Val
        115                 120                 125

Lys Thr Ile Val Phe Asn Thr Asn His Glu Val Leu Asp Gly Thr Glu
    130                 135                 140

Thr Val Ile Ser Ala Gly Ser Cys Thr Thr Asn Cys Leu Ala Pro Met
145                 150                 155                 160

Ala Asp Thr Leu Asn Lys Gln Phe Gly Ile Lys Val Gly Thr Met Thr
                165                 170                 175

Thr Val His Gly Tyr Thr Gly Asp Gln Met Thr Leu Asp Gly Pro His
            180                 185                 190

Arg Gly Gly Asp Phe Arg Arg Ala Arg Ala Ala Ala Glu Asn Ile Val
```

195                 200                 205
Pro Asn Ser Thr Gly Ala Ala Lys Ala Ile Gly Leu Val Leu Pro Glu
            210                 215                 220
Leu Gln Gly Lys Leu Gln Gly His Ala Gln Arg Val Pro Val Pro Thr
225                 230                 235                 240
Gly Ser Leu Thr Glu Leu Val Thr Ile Leu Asp Lys Glu Val Thr Val
                    245                 250                 255
Asp Glu Ile Asn Ala Ala Met Lys Ala Ala Ser Asn Glu Ser Phe Gly
            260                 265                 270
Tyr Asn Glu Asp Gln Ile Val Ser Ser Asp Ile Val Gly Ile Ser Asn
        275                 280                 285
Ser Ser Leu Phe Asp Ala Thr Gln Thr Glu Val Thr Ser Ala Asn Gly
    290                 295                 300
Ala Gln Leu Val Lys Thr Val Ser Trp Tyr Asp Asn Glu Met Ser Tyr
305                 310                 315                 320
Thr Ser Asn Leu Val Arg Thr Leu Ala Tyr Phe Ala Lys Ile Ala Lys
                325                 330                 335

<210> SEQ ID NO 17
<211> LENGTH: 113
<212> TYPE: PRT
<213> ORGANISM: Artificial Sequence
<220> FEATURE:
<223> OTHER INFORMATION: Synthetic Construct

<400> SEQUENCE: 17

Met Lys Lys Lys Ile Ile Ser Ala Ile Leu Met Ser Thr Val Ile Leu
1               5                   10                  15
Ser Ala Ala Ala Pro Leu Ser Gly Val Tyr Ala Phe Val Asn Gln His
            20                  25                  30
Leu Cys Gly Ser His Leu Val Glu Ala Leu Tyr Leu Val Cys Gly Glu
        35                  40                  45
Arg Gly Phe Phe Tyr Thr Pro Lys Thr Arg Arg Glu Ala Glu Asp Leu
    50                  55                  60
Gln Val Gly Gln Val Glu Leu Gly Gly Gly Pro Gly Ala Gly Ser Leu
65                  70                  75                  80
Gln Pro Leu Ala Leu Glu Gly Ser Leu Gln Lys Arg Gly Ile Val Glu
                85                  90                  95
Gln Cys Cys Thr Ser Ile Cys Ser Leu Tyr Gln Leu Glu Asn Tyr Cys
            100                 105                 110
Asn

<210> SEQ ID NO 18
<211> LENGTH: 3289
<212> TYPE: DNA
<213> ORGANISM: Artificial Sequence
<220> FEATURE:
<223> OTHER INFORMATION: Genetically engineered construct

<400> SEQUENCE: 18
gatggctgaa gctccaactc atgaacaagt tgaccatgtt gtggatacaa ttgttgaagt      60
tgttgaagag gaaattggtg tgaaataaag aaaagacaag gagaatattc ttcttgtctt     120
ttttcatatc ctaaaactct acctactgtg gtagagtttt tttatctttt tggcgtcta     180 gcaaactctg taaaacgaaa acggtcaacc tgatgtcgtg attcagtata ctggaaaagt     240
gtattatcgg caagatagac atgagatttc acggaaacaa catgatggtc cttcggattt     300

```
aaatcaagat atgtaaaatc atcttcacaa gcaaaatcaa tggtaacttc ttttgggca      360 taggcaatat caagtcccaa agccccttct aaataatcgt aagtagaatt ttgggcatgt     420 gcggggtca aaccatcagc gtattttct aaaaataaat cccaatccaa aatggaaaat       480
ttaccatcta cttttcttct tctaagaata ctaagggctt ggtcgccgat ggcgaatcca    540
gtagtttctg aaagagctgg ggtaattttt atactttcaa attttattac ttcagtttca    600
ctgtgaaaac ccattgaagt ttgcaattct ttatatgaag ttaagccgga atagggaaa     660 aggagccgat cgtgagcgag gacaatgctg ccatagccat gtcttctttg gatgagccct    720
ttttcttcta aaattttaa agcttgtctg acggttgaac ggctactttc ataactaata    780
gaaagttcat tctcgcttgg aagaatatcg ttcgttttat agatatcatt aaaaatcttt    840
ttttctaaat cttgcaaaat cacttcatat ttcttcatac tttatatttt atcataaaaa    900
taattgttaa cgcttgctga aaacgttttt atgaaaacgc cttaaaatgg cattttgact   960
tgcaaactgg gctaagattt gctaaaatga aaaatgccta tgtttaaggt aaaaaacaaa   1020
tggaggacat ttctaaaatg tttggaatag gaaaaaagaa agaattgaga gatgataaaa  1080
gcctttatgc tccagtttct ggggaagtta tcaaccttc aacagtcaac gaccccgtat   1140
tttcaaaaaa gataatggga gacgggttcg cggttgagcc aaaagaaaat aaaatttttg   1200
ccccagtttc tgcaaaagta actttggttc aaggacatgc aattggtttt aaacgtgctg  1260
atggcttaga tgtacttta catcttggaa ttgatacagt agctcttaaa ggtcttcatt   1320
ttaaaatcaa ggtcaaagtt gatgatattg tcaatggtgg tgatgagctt ggaagcgttg  1380
attgggcaca gattgaagct gcaggtttag ataaaacgac aatggttatc tttacaaata   1440
caaaagataa actctctgag ttcaatgtca attatggacc agctacttct ggaagtgaac   1500
ttggtaaggc aagtgttaaa taaggaggaa aaaatggcaa attattcaca acttgcgaca   1560
gaaattatcg caaatgtagg tggcgctgag aatgtcacaa aagttattca ctgtatcact   1620
cgtcttcgtt ttaccttgaa agacaaagat aaagcagata cggcggcgat tgaagcctta  1680
cctggtgtcg ctggagctgt ttataactca aacttgaatc aatatcaagt agttattgga   1740
caagctgtag aagatgttta tgacgaggtt gttgaacagc ttggagattc agttgttgat   1800
gaagatgcaa cggcgcaagc acttactgca acagcaccgg ctagtggtaa aaaacaaaat   1860
ccaattgttc atgctttcca agtggttatt gggacaatta caggttcgat gattccaatt   1920
attggtttac ttgcggctgg tgggatgatt aatggattat taagtatctt tgttaaagga   1980
aatcgtttaa ttgaagtgat tgaccctgca agttcaactt acgtcattat ctcaactcta   2040
gcaatgacac cattttattt cttacctgtt ttagtaggat tttcagcagc aaaacaatta   2100
gcacctaaag atactgtttt acaatttatt ggtgctgctg ttggtggttt catgattaat   2160
ccagggatta ctaacttggt aaatgctcat gttggaacaa atgcggccgg taaaaatgtt   2220
gttgttgaag cagcagctcc agtagcaaat ttccttggag tcactttaa tacaagttat    2280 tttggaattc cggttgcttt gccaagttat gcttatacaa ttttcccaat cattgtggcg   2340
gtagcaatcg ctaaaccttt gaatgcttgg ttgaaaaagg ttttaccact tgccttgcgt   2400
ccaatttccc aaccgatgat tactttcttc atcactgctt caatcatttt actcttggtc    2460
ggtcctgtta tttcaacaat ttcatctggt ttgtcattcg ttattgacca tatccttgtca  2520 ttaaacttag ggattgcaag tattatcgtc ggtggtttgt atcaatgttt ggttatattt   2580
ggtttgcact ggttggttgt accacttatt tcacaagagt tggcagcaac aggagcaagc   2640
tcacttaata tgattgttag cttcacaatg cttgcgcaag gagttggtgc cttgactgtc   2700
```

```
ttctttaaat ctaaaaaagc tgaccttaaa ggactttctg ctccagctgc catttcggct    2760
ttttgtggag taactgaacc tgccatgtac ggaattaact tgaaatatgt tcgcgtcttc    2820
atcatgtctt caattggtgc agcaattggt gctgggattg ccggatttgg tggcttacaa    2880
atgtttggat tttcagggtc attgattagt tttcctaact ttatctctaa tccattgacg    2940
catcatgcac ctgcgggtaa cttaatgctc ttctggattg ccactgcggt atgtgctgtt    3000
gccactttct tattagtttg gttctttggt tacaaggata ctgatgtcat gggacaagga    3060
gttgaacaaa aaatgcatt taaggatgct gtaaaataaa tagttttgct cttaataaag    3120
ttttgataca aggatttaca attatttttt gataaaaaaa ttactgatag aaatgaaaaa    3180
aattctgtca gtaattttgg aaagtcattc taaaaaattc attttaaaat gacgagaaag    3240
aaggtaaaaa gatgtttaaa gcagtattgt ttgatttaga tggcgtaat              3289

<210> SEQ ID NO 19
<211> LENGTH: 1700
<212> TYPE: DNA
<213> ORGANISM: Artificial Sequence
<220> FEATURE:
<223> OTHER INFORMATION: Genetically engineered construct

<400> SEQUENCE: 19
gtaattctaa tgctggtggg aatacaaatt caggcactag tactggaaat actggaggaa      60
caactactgg tggtagcggt ataaatagtt caccaattgg aaatccttat gctggtggtg     120
gatgtactga ctatgtatgg caatactttg ctgcacaagg aatttatatc agaaatatca     180
tgcctggtaa tggtggacaa tgggcttcta atggacctgc ccaaggcgtg ctccatgttg     240
taggagctgc tcctggtgtt atcgcatcaa gcttctcagc tgattttgtt ggatatgcaa     300
actcacctta cggtcacgta gctattgtaa atcagttaa ttcagatggt acaattacta     360
tcaaagaagg cggatatggt acaacttggt ggggacatga acgtactgta agtgcgtctg     420
gtgttacttt cttgatgcca aactaaggag gaaaaaatga cagaaccgtt aaccgaaacc     480
cctgaactat ccgcgaaata tgcctggttt tttgatcttg atggaacgct ggcggaaatc     540
aaaccgcatc ccgatcaggt cgtcgtgcct gacaatattc tgcaaggact acagctactg     600
gcaaccgcaa gtgatggtgc attggcattg atatcagggc gctcaatggt ggagcttgac     660
gcactggcaa aaccttatcg cttcccgtta gcgggcgtgc atgggcgga gcgccgtgac     720 atcaatggta aaacacatat cgttcatctg ccggatgcga ttgcgcgtga tattagcgtg     780
caactgcata cagtcatcgc tcagtatccc ggcgcggagc tggaggcgaa agggatggct     840
tttgcgctgc attatcgtca ggctccgcag catgaagacg cattaatgac attagcgcaa     900
cgtattactc agatctggcc acaaatgcg ttacagcagg gaaagtgtgt tgtcgagatc     960
aaaccgagag gtaccagtaa aggtgaggca attgcagctt ttatgcagga agctcccttt    1020
atcgggcgaa cgcccgtatt tctgggcgat gatttaaccg atgaatctgg cttcgcagtc    1080
gttaaccgac tgggcggaat gtcagtaaaa attggcacag gtgcaactca ggcatcatgg    1140
cgactggcgg gtgtgccgga tgtctggagc tggcttgaaa tgataaccac cgcattacaa    1200
caaaaaagag aaaataacag gagtgatgac tatgagtcgt ttagtcgtag tatctaaaaa    1260
aaagtcttaa taaataaaaa atagtggttt gatagtgggg ataaattttc cttctgtcaa    1320
atcatttttt attattgtgg tataataata aggaaaaatg ataaggggat agatacaaat    1380
gtgtggaatt gtcggcttta ttgaccggat cgatcaaaat gataaatcaa aaactttaga    1440
```

```
agaaatgatg gatacaatcg ctcaccgagg tccaagtagt tcaggtgaat ttattgacga    1500
aggagcagca attggttttc gtcgcctgag tattattgac cttgagggtg gagatcaacc    1560
tatctttaat gaagataaaa ctaaactttat aacctttaat ggcgaaattt ataatttccg    1620
tgaattgcgt gaagacctta tctctaaagg tcatgatttt actactcatg ctgatacaga    1680
agtgctttta catggttacg                                                1700
```

```
<210> SEQ ID NO 20
<211> LENGTH: 1029
<212> TYPE: DNA
<213> ORGANISM: Artificial Sequence
<220> FEATURE:
<223> OTHER INFORMATION: Genetically engineered construct
<220> FEATURE:
<221> NAME/KEY: MISC
<222> LOCATION: (389)..(1029)
<223> OTHER INFORMATION: Partial coding sequence of ptcC with insertion
      of tga at codon position 30 (tga30) of 446 along with an EcoRI
      site to disrupt ptcC gene

<400> SEQUENCE: 20
```

```
caccgaatta acacgcatta tgacttaacg aggcaattac ctacggtcta tttgacagaa     60
cgtttaacag atctcgttta tcaacgttcc aactaaaaaa gccaatctgg cttttttcta    120
tgctctgtcg ttcctaatgg tttgatatct aaaagtaaaa aagttaaatt gagataacaa    180
atataattat caaggctgaa cctcgcaagc ttaaaggaaa cttatatgac aattttggta    240
caggagtctt caaaagtggc acagaaccaa agtgatggaa aaataagaaa ctgctttctt    300
tactttgcct attaatgcta taatgaaaat gtagaaaaga tggacgtgaa accagttcat    360
caaaaaaagt aaaggagact gttcaaccat gaacaatttt attcaaaaca aaatcatgcc    420
tccaatgatg aaatttttga atacccgtgc agtcacggca atcaaaaatg gtatgtgaat    480
tcctatccca tttatcatta ttggttcagt attcttgatt cttggtcaac tgccattcca    540
agcaggacaa gacttcatga acaaaatcaa attgggccca ctctttttac aaattaataa    600
tgcttcattt ggtattatgg ctttgcttgc cgtgttcggt attgcttacg cttgggttcg    660
agatgcaggt tatgaaggag tacccgctgg tttaacaggt gtcattgttc acatcttgtt    720
gcaaccagac acaatccatc aagtaacaag tgttactgac ccaactaaaa catcaacagc    780
atttcaagta ggtggtgtca ttgaccgagc ttggttaggt gggaaaggga tggttctctc    840
aatcatcgtt ggactcttag taggttggat ttacactggc tttatgcgtc ggaacatcac    900
aatcaaaatg ccagaacaag ttccagaaaa cgttgccgca tcatttactt cacttgtacc    960
tgcaggagca atcattacaa tggctggtgt ggttcatgga atcacaacga ttggcttcaa   1020
cacaacttt                                                           1029
```

```
<210> SEQ ID NO 21
<211> LENGTH: 29
<212> TYPE: PRT
<213> ORGANISM: Artificial Sequence
<220> FEATURE:
<223> OTHER INFORMATION: Genetically engineered
<220> FEATURE:
<221> NAME/KEY: MISC_FEATURE
<222> LOCATION: (1)..(29)
<223> OTHER INFORMATION: Sequence encoded by codon 1 through codon 29 of
      ptcC gene disrupted by tga30 codon and EcoRI site

<400> SEQUENCE: 21
```

```
Met Asn Asn Phe Ile Gln Asn Lys Ile Met Pro Pro Met Met Lys Phe
1               5                   10                  15
```

```
Leu Asn Thr Arg Ala Val Thr Ala Ile Lys Asn Gly Met
        20                  25
```

<210> SEQ ID NO 22
<211> LENGTH: 500
<212> TYPE: DNA
<213> ORGANISM: Artificial Sequence
<220> FEATURE:
<223> OTHER INFORMATION: Genetically engineered construct

<400> SEQUENCE: 22

```
tcagctaacg gagctcaact tgttaaaact gtatcttggt acgataacga aatgtcatac      60
acttcaaacc ttgttcgtac acttgcatac ttcgctaaaa tcgctaaata aggaggaaaa     120
aatgaagaag aaaatcatta gtgccatctt aatgtctaca gtgattcttt cagctgcagc     180
tcctttatca ggcgtttatg catttgtgaa ccaacacctg tgcggctcac acctggtgga     240
agctctctac ctagtgtgcg gggaacgagg cttcttctac acacccaaga cccgccggga     300
ggcagaggac ctgcaggtgg ggcaggtgga gctgggcggg ggccctggtg caggcagcct     360
gcagcccttg gccctggagg ggtccctgca gaagcgtggc attgtggaac aatgctgtac     420
cagcatctgc tccctctacc agctggagaa ctactgcaac taattttccg attttaacgg     480
tataaaaacc agtcttcggg                                                 500
```

<210> SEQ ID NO 23
<211> LENGTH: 1000
<212> TYPE: DNA
<213> ORGANISM: Artificial Sequence
<220> FEATURE:
<223> OTHER INFORMATION: Genetically engineered construct
<220> FEATURE:
<221> NAME/KEY: CDS
<222> LOCATION: (312)..(872)
<223> OTHER INFORMATION: Gene encoding fusion of SSusp45 (nt 312-392)
      and hIL-10 (nt. 393-876)

<400> SEQUENCE: 23

```
aatccaatga cggcacttct tccttggacg acaccagcac ctgtgagaat ggccatttca      60
ggtggacttc cattttttgat tatttttgca atctgtttag tcttgaatgt tcttatttac    120
tacccattct ttaaggtggc gtataataaa gctttagaag aagaaaaagc agctgttgaa     180
ttagagggtt cagaaactgc ctgatggaaa acgccttaaa atggcatttt gacttgcaaa     240
ctgggctaag atttgctaaa atgaaaaatg cctatgttta aggtaaaaaa caaatggagg     300
acatttctaa a atg aaa aaa aag att atc tca gct att tta atg tct aca      350
            Met Lys Lys Lys Ile Ile Ser Ala Ile Leu Met Ser Thr
              1               5                  10 gtg ata ctt tct gct gca gcc ccg ttg tca ggt gtt tac gcc tca gct       398
Val Ile Leu Ser Ala Ala Ala Pro Leu Ser Gly Val Tyr Ala Ser Ala
        15                  20                  25 ggt caa ggt act caa tca gaa aac tca tgt act cac ttt cca ggt aac       446
Gly Gln Gly Thr Gln Ser Glu Asn Ser Cys Thr His Phe Pro Gly Asn
 30                  35                  40                  45 ttg cca aac atg ctt cgt gat ttg cgt gat gct ttt tca cgt gtt aaa       494
Leu Pro Asn Met Leu Arg Asp Leu Arg Asp Ala Phe Ser Arg Val Lys
                 50                  55                  60 act ttt ttt caa atg aaa gat caa ctt gat aac ttg ctt ttg aaa gaa       542
Thr Phe Phe Gln Met Lys Asp Gln Leu Asp Asn Leu Leu Leu Lys Glu
             65                  70                  75 tca ctt ttg gaa gat ttt aaa ggt tac ctt ggt tgt caa gct ttg tca       590
Ser Leu Leu Glu Asp Phe Lys Gly Tyr Leu Gly Cys Gln Ala Leu Ser
```

```
                80                  85                  90
gaa atg atc caa ttt tac ctt gaa gaa gtt atg cca caa gct gaa aac     638
Glu Met Ile Gln Phe Tyr Leu Glu Glu Val Met Pro Gln Ala Glu Asn
 95                 100                 105 caa gat cca gat atc aaa gct cac gtt aac tca ttg ggt gaa aac ctt     686
Gln Asp Pro Asp Ile Lys Ala His Val Asn Ser Leu Gly Glu Asn Leu
110                 115                 120                 125 aaa act ttg cgt ctt cgt ttg cgt cgt tgt cac cgt ttt ctt cca tgt     734
Lys Thr Leu Arg Leu Arg Leu Arg Arg Cys His Arg Phe Leu Pro Cys
                130                 135                 140 gaa aac aaa tca aaa gct gtt gaa caa gtt aaa aac gct ttt aac aaa     782
Glu Asn Lys Ser Lys Ala Val Glu Gln Val Lys Asn Ala Phe Asn Lys
            145                 150                 155 ttg caa gaa aaa ggt atc tac aaa gct atg tca gaa ttt gat atc ttt     830
Leu Gln Glu Lys Gly Ile Tyr Lys Ala Met Ser Glu Phe Asp Ile Phe
        160                 165                 170 atc aac tac atc gaa gct tac atg act atg aaa atc cgt aac             872
Ile Asn Tyr Ile Glu Ala Tyr Met Thr Met Lys Ile Arg Asn
    175                 180                 185 taactagaat taatctataa gttactgaca aaactgtcag taactttttt tgtgggaaaa   932
atgtattttt atgaccgtaa agaatctgtc agtagaagtc tgaaattcgt ttaaaaatcg   992
actagaat                                                           1000

<210> SEQ ID NO 24
<211> LENGTH: 187
<212> TYPE: PRT
<213> ORGANISM: Artificial Sequence
<220> FEATURE:
<223> OTHER INFORMATION: Synthetic Construct

<400> SEQUENCE: 24

Met Lys Lys Lys Ile Ile Ser Ala Ile Leu Met Ser Thr Val Ile Leu
 1               5                   10                  15

Ser Ala Ala Ala Pro Leu Ser Gly Val Tyr Ala Ser Ala Gly Gln Gly
            20                  25                  30

Thr Gln Ser Glu Asn Ser Cys Thr His Phe Pro Gly Asn Leu Pro Asn
        35                  40                  45

Met Leu Arg Asp Leu Arg Asp Ala Phe Ser Arg Val Lys Thr Phe Phe
    50                  55                  60

Gln Met Lys Asp Gln Leu Asp Asn Leu Leu Leu Lys Glu Ser Leu Leu
65                  70                  75                  80

Glu Asp Phe Lys Gly Tyr Leu Gly Cys Gln Ala Leu Ser Glu Met Ile
                85                  90                  95

Gln Phe Tyr Leu Glu Glu Val Met Pro Gln Ala Glu Asn Gln Asp Pro
            100                 105                 110

Asp Ile Lys Ala His Val Asn Ser Leu Gly Glu Asn Leu Lys Thr Leu
        115                 120                 125

Arg Leu Arg Leu Arg Arg Cys His Arg Phe Leu Pro Cys Glu Asn Lys
    130                 135                 140

Ser Lys Ala Val Glu Gln Val Lys Asn Ala Phe Asn Lys Leu Gln Glu
145                 150                 155                 160

Lys Gly Ile Tyr Lys Ala Met Ser Glu Phe Asp Ile Phe Ile Asn Tyr
                165                 170                 175

Ile Glu Ala Tyr Met Thr Met Lys Ile Arg Asn
            180                 185
```

```
<210> SEQ ID NO 25
<211> LENGTH: 183
<212> TYPE: PRT
<213> ORGANISM: Artificial Sequence
<220> FEATURE:
<223> OTHER INFORMATION: Genetically engineered
<220> FEATURE:
<221> NAME/KEY: MISC_FEATURE
<222> LOCATION: (1)..(183)
<223> OTHER INFORMATION: Sequence encoded after tga30 codon and EcoRI
      site of disrupted ptcC gene to amino acid 213 of ptcC

<400> SEQUENCE: 25

Ile Pro Ile Pro Phe Ile Ile Ile Gly Ser Val Phe Leu Ile Leu Gly
1               5                   10                  15

Gln Leu Pro Phe Gln Ala Gly Gln Asp Phe Met Asn Lys Ile Lys Leu
            20                  25                  30

Gly Pro Leu Phe Leu Gln Ile Asn Asn Ala Ser Phe Gly Ile Met Ala
        35                  40                  45

Leu Leu Ala Val Phe Gly Ile Ala Tyr Ala Trp Val Arg Asp Ala Gly
    50                  55                  60

Tyr Glu Gly Val Pro Ala Gly Leu Thr Gly Val Ile Val His Ile Leu
65                  70                  75                  80

Leu Gln Pro Asp Thr Ile His Gln Val Thr Ser Val Thr Asp Pro Thr
                85                  90                  95

Lys Thr Ser Thr Ala Phe Gln Val Gly Gly Val Ile Asp Arg Ala Trp
            100                 105                 110

Leu Gly Gly Lys Gly Met Val Leu Ser Ile Ile Val Gly Leu Leu Val
        115                 120                 125

Gly Trp Ile Tyr Thr Gly Phe Met Arg Arg Asn Ile Thr Ile Lys Met
    130                 135                 140

Pro Glu Gln Val Pro Glu Asn Val Ala Ala Ser Phe Thr Ser Leu Val
145                 150                 155                 160

Pro Ala Gly Ala Ile Ile Thr Met Ala Gly Val Val His Gly Ile Thr
                165                 170                 175

Thr Ile Gly Phe Asn Thr Thr
            180
```

What is claimed is:

1. A method for treating type-1 diabetes (T1D) in a human in need thereof comprising administering to said human a therapeutically effective amount of:
   (i) a recombinant lactic acid bacterium (LAB), or
   (ii) a pharmaceutical composition comprising said recombinant LAB and a pharmaceutically acceptable carrier,
   wherein said recombinant LAB comprises two chromosomally integrated exogenous nucleic acids,
   wherein a first exogenous nucleic acid encodes a human interleukin-10 (hIL-10) comprising an amino acid sequence at least 95% identical to SEQ ID NO: 1,
   wherein a second exogenous nucleic acid encodes a human proinsulin (hPINS) comprising an amino acid sequence at least 95% identical to SEQ ID NO: 3,
   wherein said LAB:
   a) constitutively expresses and secretes said hIL-10 and said hPINS;
   b) lacks trehalose-6-phosphate phosphorylase (TrePP) activity; and
   c) lacks cellobiose-specific PTS system IIC component (PtcC) activity;
   wherein said first exogenous nucleic acid has at least one feature selected from:
   a) is transcriptionally regulated by an hllA promoter (PhllA); and
   b) is chromosomally integrated at an thyA locus of said LAB, and
   wherein said hIL-10 comprises a proline (Pro) to alanine (Ala) substitution at position 2 of a mature hIL-10.

2. The method of claim 1, wherein said recombinant LAB is a recombinant *Lactococcus lactis*.

3. The method of claim 1, wherein said hIL-10 is expressed as a fusion protein comprising a Usp45 secretion leader (SSusp45) or comprises an amino acid sequence at least 97% identical to SEQ ID NO: 1.

4. The method of claim 1, wherein said second exogenous nucleic acid comprises a nucleotide sequence at least 95% identical to SEQ ID NO: 4, or is inserted in a first polycistronic expression cassette comprising, in 5' to 3' order, a gapB promoter, a gapB gene, a nucleic acid sequence encoding a Usp45 secretion leader (SSusp45), and said second exogenous nucleic acid, wherein said first polycistronic expression cassette expresses a hPINS fusion protein comprising said Usp45 secretion leader (SSusp45).

5. The method of claim 4, wherein said first polycistronic expression cassette further comprises, between said gapB gene and said second exogenous nucleic acid, an intergenic region that is immediately 5' to an rpmD gene.

6. The method of claim 1, wherein said hPINS
comprises an amino acid sequence at least 97% identical to SEQ ID NO: 3 or is
expressed as a fusion protein comprising a Usp45 secretion leader (SSusp45).

7. The method of claim 1, wherein said recombinant LAB comprises an exogenous trehalose 6-phosphate phosphatase, or constitutively overexpresses a gene encoding at least one trehalose transporter.

8. The method of claim 7,
wherein said trehalose 6-phosphate phosphatase is an OtsB from *Escherichia coli*;
wherein said at least one trehalose transporter is encoded by a ptsI gene and a ptsII gene;
wherein said recombinant LAB comprises an inactivated endogenous trePP, so that said recombinant LAB lacks TrePP activity; and
wherein said recombinant LAB comprises an inactivated endogenous ptcC, so that said recombinant LAB lacks PtcC activity.

9. The method of claim 2, where said recombinant LAB comprises:
a) an expression cassette chromosomally integrated at said thyA locus of said recombinant LAB, wherein said expression cassette comprises an hllA promoter (PhllA) that transcribes a nucleic acid sequence encoding a Usp45 secretion leader (SSusp45) and said first exogenous nucleic acid, and wherein said hIL-10 is expressed as a fusion protein comprising said SSusp45;
b) a first chromosomally integrated polycistronic expression cassette comprising, in 5' to 3' order, a gapB promoter, a gapB gene, a nucleic acid sequence encoding a Usp45 secretion leader, and said second exogenous nucleic acid, wherein said hPINS is expressed as a fusion protein comprising said SSusp45;
c) a second chromosomally integrated polycistronic expression cassette comprising, in 5' to 3' order, a usp45 promoter, a usp45 gene, an intergenic region that is immediately 5' to an rpmD gene, and a third exogenous nucleic acid encoding an OtsB from *Escherichia coli*;
d) a third polycistronic expression cassette comprising, in 5' to 3' order, an hllA promoter (PhllA) and a nucleic acid comprising a ptsI gene and a ptsII gene;
e) an inactivated endogenous trePP gene, wherein said trePP gene is inactivated by gene deletion so that said recombinant LAB lacks TrePP activity; and
f) an inactivated endogenous ptcC gene, wherein said ptcC gene is inactivated by insertion of a premature stop codon, so that said recombinant LAB lacks PtcC activity.

10. The method of claim 1, wherein said human has recent-onset T1D.

11. The method of claim 1, wherein a blood sample of said human is positive for an insulin autoantibody (IAA), an islet-cell auto-antibody, a glutamic acid decarboxylase (GAD65) auto-antibody, or an ICA512 antibody.

12. The method of claim 11, wherein said blood sample of said human is positive for said IAA.

13. The method of claim 1, further comprising measuring an amount of an insulin autoantibody (IAA) in a blood sample of said human.

14. The method of claim 13, wherein the amount of said IAA in said blood sample of said human is indicative of T1D progression or an outcome of said treatment of T1D.

15. The method of claim 13, wherein measuring the amount of said IAA occurs:
a) before administering said recombinant LAB or said pharmaceutical composition to predict an outcome of said treatment of T1D; or
b) after administering said recombinant LAB or said pharmaceutical composition to monitor and measure an outcome of said treatment of T1D.

16. The method of claim 1, further comprising administering an immunomodulatory agent to said human.

17. The method of claim 16, wherein said immunomodulatory agent is an anti-CD3 antibody.

* * * * *